United States Patent
Lowery, Jr. et al.

(10) Patent No.: US 9,797,914 B2
(45) Date of Patent: *Oct. 24, 2017

(54) NMR METHODS FOR MONITORING BLOOD CLOT FORMATION

(71) Applicant: T2 Biosystems, Inc., Lexington, MA (US)

(72) Inventors: Thomas Jay Lowery, Jr., Belmont, MA (US); Vyacheslav Papkov, Waltham, MA (US); Walter W. Massefski, Jr., Sharon, MA (US); Rahul K. Dhanda, Needham, MA (US); Edward Chris Thayer, Woodinville, WA (US)

(73) Assignee: T2 Biosystems, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/803,577

(22) Filed: Jul. 20, 2015

(65) Prior Publication Data

US 2016/0018421 A1   Jan. 21, 2016

Related U.S. Application Data

(63) Continuation of application No. 14/131,898, filed as application No. PCT/US2012/046669 on Jul. 13, 2012.

(Continued)

(51) Int. Cl.
*G01N 24/00* (2006.01)
*G01N 33/86* (2006.01)
(Continued)

(52) U.S. Cl.
CPC .......... *G01N 33/86* (2013.01); *A61M 1/1086* (2013.01); *G01N 24/08* (2013.01); *G01N 24/088* (2013.01);
(Continued)

(58) Field of Classification Search
None
See application file for complete search history.

(56) References Cited

U.S. PATENT DOCUMENTS 4,101,435 A   7/1978   Hasegawa et al.
4,374,360 A   2/1983   Sepponen
(Continued)

FOREIGN PATENT DOCUMENTS

JP   2000-166897 A   6/2000
JP   2006-162623 A   6/2006
(Continued)

OTHER PUBLICATIONS

Li, Y., Determining NMR relaxation times for porous media: Theory, measurement and the inverse problem, 2007, A thesis presented to the University of Waterloo in fulfillment of the thesis requirement for the degree of Master of Mathematics in Applied Mathematics. Waterloo, Ontario, Canada.*

(Continued)

*Primary Examiner* — Robert Xu
(74) *Attorney, Agent, or Firm* — Clark & Elbing LLP

(57) ABSTRACT

The invention features a method of monitoring a clotting process by measuring a signal characteristic of the NMR relaxation of water in a sample undergoing clotting to produce NMR relaxation data and determining from the NMR relaxation data a magnetic resonance parameter of water in the sample characteristic of the clots being formed.

23 Claims, 31 Drawing Sheets

Related U.S. Application Data

(60) Provisional application No. 61/625,945, filed on Apr. 18, 2012, provisional application No. 61/596,445, filed on Feb. 8, 2012, provisional application No. 61/560,920, filed on Nov. 17, 2011, provisional application No. 61/538,257, filed on Sep. 23, 2011, provisional application No. 61/537,396, filed on Sep. 21, 2011, provisional application No. 61/507,307, filed on Jul. 13, 2011.

(51) Int. Cl.
  *G01N 24/08* (2006.01)
  *G01R 33/44* (2006.01)
  *A61M 1/10* (2006.01)

(52) U.S. Cl.
  CPC ..... *G01R 33/448* (2013.01); *G01N 2800/226* (2013.01); *G01N 2800/52* (2013.01)

(56) References Cited

U.S. PATENT DOCUMENTS

| | | |
|---|---|---|
| 4,452,773 A | 6/1984 | Molday |
| 4,875,486 A | 10/1989 | Rapoport et al. |
| 4,920,061 A | 4/1990 | Poynton et al. |
| 5,042,488 A | 8/1991 | Ackerman |
| 5,049,819 A | 9/1991 | Dechene et al. |
| 5,136,095 A | 8/1992 | Tarnowski et al. |
| 5,164,297 A | 11/1992 | Josephson et al. |
| 5,204,457 A | 4/1993 | Maruno et al. |
| 5,254,460 A | 10/1993 | Josephson et al. |
| 5,262,176 A | 11/1993 | Palmacci et al. |
| 5,424,419 A | 6/1995 | Hasegawa et al. |
| 5,445,970 A | 8/1995 | Rohr |
| 5,445,971 A | 8/1995 | Rohr |
| 5,492,814 A | 2/1996 | Weissleder |
| 5,637,469 A | 6/1997 | Wilding et al. |
| 5,801,003 A | 9/1998 | Shimamura et al. |
| 6,013,188 A | 1/2000 | Terstappen et al. |
| 6,165,378 A | 12/2000 | Maruno et al. |
| 6,294,342 B1 | 9/2001 | Rohr et al. |
| 6,297,062 B1 | 10/2001 | Gombinski |
| 6,307,372 B1 | 10/2001 | Sugarman et al. |
| 6,342,396 B1 | 1/2002 | Perrin et al. |
| 6,361,944 B1 | 3/2002 | Mirkin et al. |
| 6,500,343 B2 | 12/2002 | Siddiqi |
| 6,548,311 B1 | 4/2003 | Knoll |
| 6,599,498 B1 | 7/2003 | Groman et al. |
| 6,630,355 B1 | 10/2003 | Pivarnik et al. |
| 6,767,635 B1 | 7/2004 | Bahr et al. |
| 6,866,838 B1 | 3/2005 | Mondain-Monval et al. |
| 6,884,357 B2 | 4/2005 | Siddiqi |
| 6,940,378 B2 | 9/2005 | Miller et al. |
| 7,001,589 B2 | 2/2006 | Mondain-Monval et al. |
| 7,018,849 B2 | 3/2006 | Piasio et al. |
| 7,179,652 B2 | 2/2007 | Cohen et al. |
| 7,217,457 B2 | 5/2007 | Elaissari et al. |
| 7,217,542 B2 | 5/2007 | Tyvoll et al. |
| 7,274,191 B2 | 9/2007 | Park et al. |
| 7,332,353 B2 | 2/2008 | Baudry et al. |
| 7,517,457 B2 | 4/2009 | Siddiqi |
| 7,553,542 B2 | 6/2009 | Ou et al. |
| 7,564,245 B2 | 7/2009 | Lee |
| 7,781,228 B2 | 8/2010 | Menon et al. |
| 7,829,350 B2 | 11/2010 | Josephson et al. |
| 8,339,135 B2 | 12/2012 | Sillerud et al. |
| 9,157,974 B2 | 10/2015 | Taktak et al. |
| 2002/0102214 A1 | 8/2002 | Briley-Saebo et al. |
| 2003/0054432 A1 | 3/2003 | Chen et al. |
| 2003/0216638 A1 | 11/2003 | Dharmakumar et al. |
| 2003/0219904 A1 | 11/2003 | Cohen et al. |
| 2003/0222648 A1 | 12/2003 | Fan |
| 2004/0175388 A1 | 9/2004 | Ding et al. |
| 2004/0214348 A1 | 10/2004 | Nicholson et al. |
| 2006/0121617 A1 | 6/2006 | Henckel et al. |
| 2006/0269965 A1 | 11/2006 | Josephson et al. |
| 2007/0038121 A1 | 2/2007 | Feldman et al. |
| 2007/0116602 A1 | 5/2007 | Lee |
| 2007/0166730 A1 | 7/2007 | Menon et al. |
| 2008/0199539 A1 | 8/2008 | Baker et al. |
| 2008/0204022 A1 | 8/2008 | Sillerud et al. |
| 2008/0261261 A1 | 10/2008 | Grimes et al. |
| 2008/0305048 A1 | 12/2008 | Josephson et al. |
| 2009/0099342 A1 | 4/2009 | Braconnot et al. |
| 2010/0039109 A1 | 2/2010 | Cheng et al. |
| 2010/0072994 A1 | 3/2010 | Lee et al. |
| 2010/0120174 A1 | 5/2010 | Josephson et al. |
| 2011/0312002 A1 | 12/2011 | Taktak et al. |
| 2012/0100546 A1 | 4/2012 | Lowery, Jr. et al. |
| 2013/0260367 A1 | 10/2013 | Lowery, Jr. et al. |
| 2014/0212901 A1 | 7/2014 | Lowery, Jr. et al. |

FOREIGN PATENT DOCUMENTS

| | | |
|---|---|---|
| JP | 3876022 B2 | 1/2007 |
| JP | 3917239 B2 | 5/2007 |
| JP | 2008128883 A | 6/2008 |
| JP | 2008209350 A | 9/2008 |
| WO | WO-90/06045 A2 | 6/1990 |
| WO | WO-91/17428 A1 | 11/1991 |
| WO | WO-97/40181 A1 | 10/1997 |
| WO | WO-98/04740 A1 | 2/1998 |
| WO | WO-01/00876 A1 | 1/2001 |
| WO | WO-01/11360 A2 | 2/2001 |
| WO | WO-01/19405 A2 | 3/2001 |
| WO | WO-02/098364 A2 | 12/2002 |
| WO | WO-2005/099419 A2 | 10/2005 |
| WO | WO-2005/111596 A1 | 11/2005 |
| WO | WO-2008/007270 A2 | 1/2008 |
| WO | WO-2008/010111 A2 | 1/2008 |
| WO | WO-2008/072156 A2 | 6/2008 |
| WO | WO-2008/119054 A1 | 10/2008 |
| WO | WO-2008/137721 A2 | 11/2008 |
| WO | WO-2009/017697 A2 | 2/2009 |
| WO | WO-2009/026251 A1 | 2/2009 |
| WO | WO-2009/045354 A1 | 4/2009 |
| WO | WO-2009/045551 A1 | 4/2009 |
| WO | WO-2009/055587 A1 | 4/2009 |
| WO | WO-2009/061481 A1 | 5/2009 |
| WO | WO-2009/085214 A1 | 7/2009 |
| WO | WO-2010/002479 A1 | 1/2010 |
| WO | WO-2010/051362 A1 | 5/2010 |
| WO | WO-2013/010080 A1 | 1/2013 |
| WO | WO-2013/043858 A1 | 3/2013 |
| WO | WO-2013/190071 A2 | 12/2013 |
| WO | WO-2014/004573 A1 | 1/2014 |

OTHER PUBLICATIONS

Atanasijevic et al., "Calcium-sensitive MRI contrast agents based on superparamagnetic iron oxide nanoparticles and calmodulin." Proc Natl Acad Sci USA. 103(40):14707-12 (2006).

Author Manuscript of Hong et al., "Magnetic microparticle aggregation for viscosity determination by magnetic resonance." available in PMC Septmeber 10, 2009, published in final edited form as, Magn Reson Med. 59(3):515-20 (2008).

Author Manuscript of Koh et al., "Sensitive NMR sensors detect antibodies to influenza." available in PMC Apr. 13, 2009, published in final edited form as Angew Chem. 47(22):4119-21 (2008).

Azoury et al., "Structural changes in fibrin clot associated with the proteolytic activity induced by tissue type plasminogen activator. An NMR study," Biochim Biophys Acta. 295(3):295-300 (1989).

Baudry et al., "Acceleration of the recognition rate between grafted ligands and receptors with magnetic forces." Proc Natl Acad Sci U.S.A. 103(44):16076-8 (2006).

Blackmore et al., "Magnetic resonance imaging of blood and clots in vitro." Invest Radiol. 25(12):1316-24 (1990).

Blinc et al., "Proton NMR study of the state of water in fibrin gels, plasma, and blood clots," Magn Reson Med. 14(1):105-22 (1990).

Brooks et al., "Nuclear magnetic relaxation in blood." IEEE Trans Biomed Eng. 22(1):12-18 (1975).

(56) References Cited

OTHER PUBLICATIONS

Bryant et al., "Magnetic relaxation in blood and blood clots." Magn Reson Med. 13(1):133-44 (1990).
Carr, "Development of platelet contractile force as a research and clinical measure of platelet function." Cell Biochem Biophys. 38(1):55-78 (2003).
Cazenave et al., "Preparation of washed platelet suspensions from human and rodent blood," Methods Mol Biol. 272(1):13-28 (2004).
Chan et al., "Reference values for kaolin-activated thromboelastography in healthy children." Anesth Analg. 105(6):1610-3 (2007).
Clark et al., "Acute hematomas: Effects of deoxygenation, hematocrit, and fibrin-clot formation and retraction on T2 shortening," Radiology. 175(1):201-6 (1990).
Cohen-Tannoudji et al., "Measuring the kinetics of biomolecular recognition with magnetic colloids." Phys Rev Lett. 100(10):108301-1-4 (2008).
Colombo et al., "Femtomolar detection of autoantibodies by magnetic relaxation nanosensors." Anal Biochem. 392(1):96-102 (2009).
Costanzo et al., "Protein-ligand mediated aggregation of nanoparticles: a study of synthesis and assembly mechanism." Chem Mater. 16(9):1775-85 (2004).
Cover, "A robust and reliable method for detecting signals of interest in multiexponential decays," Rev Sci Instrum. 79(5):055106 1-11 (2008).
Craft et al., "A novel modification of the thrombelastograph assay, isolating platelet function, correlates with optical platelet aggregation." J Lab Clin Med. 143(5):301-9 (2004).
De Gaetano et al., "Effect of platelets on clot structuration, a thrombelastographic study." Thromb Res. 3:425-35 (1973).
de Gaetano et al., "Retraction of reptilase-clots in the presence of agents inducing or inhibiting the platelet adhesion-aggregation reaction." Thromb Resear. 2(1):71-84 (1973).
Demas et al., "Portable, low-cost NMR with laser-lathe lithography produced microcoils." J Magn Reson. 189(1):1-20 (2007).
Downey et al., "Novel and diagnostically applicable information from optical waveform analysis of bood coagulation in disseminated intravascular coagulation." Br J Haematol. 98(1):67-73 (1997).
Dreyfus et al., "Microscopic artificial swimmers." Nature. 437(7060):862-5 (2005).
Edzes, "An analysis of the use of pulse multiplets in the single scan determination of spin-lattice relaxation rates." J Magne Reson. 17:301-13 (1975).
Enriquez et al., "Point-of-care coagulation testing and transfusion algorithms." Br J Anaesthe. 103:i14-i22 (2009).
Examination Report for Australian Application No. 2009308841, issued Jun. 24, 2013 (3 pages).
Extended European Search Report for European Application No. 12812054.0, mailed Feb. 23, 2015 (10 pages).
Extended European Search Report for European Patent Application No. 12833431.5, dated May 4, 2015 (5 pages).
Extended European Search Report for European Patent Application No. 09824124.3, dated Dec. 4, 2013 (13 pages).
Fry et al., "A new approach to template purification for sequencing applications using paramagnetic particles." Biotechniques. 13(1):124-31 (1992).
Gijs, "Magnetic bead handling on-chip: new opportunities for analytical applications." Microfluid Nanofluid. 1:22-40 (2004).
Gillis et al., "Transverse relaxation of solvent protons induced by magnetized spheres: application to ferritin, erythrocytes, and magnetite." Magn Reson Med. 5(4):323-45 (1987).
Gomori et al., "NMR relaxation times of blood: dependence on field strength, oxidation state, and cell integrity." J Comp Assist Tomog. 11(4):684-90 (1987).
Grimm et al., "Novel nanosensors for rapid analysis of telomerase activity." Cancer Res. 64(2):639-43 (2004).

Hansen et al., "Effect of gel firmness at cutting time, pH, and temperature on rennet coagulation and syneresis: An in situ 1H NMR relaxation study." J Agric Food Chem. 58:513-9 (2010).
Herbst et al., "A review of water diffusion measurement by NMR in human red blood cells." Am J Physiol. 256:C1097-104 (1989).
Hiltbrand et al., "Variations in proton relaxation in the weak field during coagulation." C. R. Acad Sci. II:1465-7 (1981).
International Preliminary Report on Patentability and Written Opinion for International Patent Application No. PCT/US2012/046669, mailed Jan. 23, 2014 (10 pages).
International Preliminary Report on Patentability for International Application No. PCT/US2009/062537, dated Jul. 20, 2011 (16 pages).
International Preliminary Report on Patentability for International Patent Application No. PCT/US2012/056312, dated Mar. 25, 2014 (7 pages).
International Search Report for International Application No. PCT/US2009/062537, mailed Dec. 23, 2009 (3 pages).
International Search Report for International Application No. PCT/US2012/046669 mailed Oct. 26, 2012 (2 pages).
Istratov et al., "Exponential analysis in physical phenomena." Rev Sci Instrum. 70(2):1233-57 (1999).
Josephson et al., "High-efficiency intracellular magnetic labeling with novel superparamagnetic-Tat peptide conjugates." Bioconjug Chem. 10(2):186-191 (1999).
Josephson et al., "Magnetic nanosensors for the detection of oligonucleotide sequences." Angew Chem. 40(17):3204-6 (2001).
Kim et al., "Magnetic relaxation switch detection of human chorionic gonadotrophin." Bioconjug Chem. 18(6):2024-8 (2007).
Koenig et al., "Theory of $1/T_1$ and $1/T_2$ NMRD profiles of solutions of magnetic nanoparticles." Magn Reson Med. 34(2):227-33 (1995).
Koh et al., "Magnetic nanoparticle sensors." Sensors. 9(10):8130-45 (2009).
Koh et al., "Nanoparticle-target interactions parallel antibody-protein interactions." Anal Chem. 81(9):3618-22 (2009).
Kriz et al., "Advancements toward magneto immunoassays." Biosens Bioelectron. 13(7-8):817-23 (1998).
Kriz et al., "Magnetic permeability measurements in bioanalysis and biosensors." Anal Chem. 68(11):1966-70 (1996).
Kroll, "Thromboelastography: theory and practice in measuring hemostasis." Clin Lab News. 8-10 (2010).
Kötitz et al., "Determination of the binding reaction between avidin and biotin by relaxation measurements of magnetic nanoparticles." J Magn Magn Mater. 194:62-8 (1999).
Landler et al., "In vitro T1- and T2-relaxation times of coagulating blood and thromboses." Z Naturforsch C. 42(9-10):1135-9 (1987) (English Abstract Only).
Lee et al., "Ligand-receptor interactions in chains of colloids: when reactions are limited by rotational diffusion." Langmuir. 24(4):1296-307 (2008).
Lee et al., "Microelectromagnets for the control of magnetic nanoparticles." Appl Phys Letters. 79(20):3308-10 (2001).
Lewin et al., "Tat peptide-derivatized magnetic nanoparticles allow in vivo tracking and recovery of progenitor cells." Nat Biotechnol. 18(4):410-4 (2000).
Liu, "CMOS Magnetic Cell Manipulator and CMOS NMR Biomolecular Sensor," Harvard University Ph.D. dissertation, Nov. 5, 2007 (167 pages).
Lowery, "Nanomaterials-Based Magnetic Relaxation Biosensors," in Kumar, CSSR, Ed. Nanomaterials for the Life Sciences vol. 4: Magnetic Nanomaterials. Weinheim: Wiley-VCH Verlag GmbH & Co. KgaA, (2009) (52 pages).
Makiranta et al., "Master of Science Thesis", Tampere University of Technology, Oct. 2004 (English Abstract Included) (111 pages).
Makiranta et al., "Modeling and simulation of magnetic nanoparticle sensor", Proceedings of the 2005 IEEE, Shanghai, China, Sep. 1-4, 2005, 1256-59 (2005).
Malba et al., "Laser-lathe lithography—a novel method for manufacturing nuclear magnetic resonance microcoils." Biomed Micro. 5(1):21-7 (2003).
Martin et al., "Strong intrinsic mixing in vortex magnetic fields." Phys Rev E Stat Nonlin Soft Matter Phys. 80(1):016312-1-6 (2009).

(56) References Cited

OTHER PUBLICATIONS

Martin, "Theory of strong intrinsic mixing of particle suspensions in vortex magnetic fields." Phys Rev E State Nonlin Soft Matter Phys. 79(1):011503-1-12 (2009).
Massicotte et al., "Home monitoring of warfarin therapy in children with a whole blood prothrombin time monitor," J Pediatr. 127(3):389-94 (1995).
Massin et al., "Planar microcoil-based magnetic resonance imaging of cells", Transducers, Solid-state Sensors, Actuators and Microsystems 12th Int'l conference, Boston, Jun. 8-12, 2003, 967-970.
Massin et al., "Planar microcoil-based microfluidic NMR probes." J Mag Reson. 164(2):242-55 (2003).
Molday et al., "Immunospecific ferromagnetic iron-dextran reagents for the labeling and magnetic separation of cells." J Immuno Meth. 52:353-67 (1982).
Moser et al., "On-chip immune-agglutination assay with analyte capture by dynamic manipulation of superparamagnetic beads." Lab Chip. 9(22):3261-7 (2009).
Niemeyer et al., "Self-assembly of DNA-streptavidin nanostructures and their use as reagents in immuno-PCR." Nucleic Acid Res. 27(23):4553-61 (1999).
Notice of Reasons for Rejection for Japanese Patent Application No. 2011-534756, mailed Apr. 2, 2013 (10 pages) (English Language Translation Included).
Notice of Reasons for Rejection for Japanese Patent Application No. 2011-534756, mailed Jun. 10, 2014 (3 pages) (English Language Translation Included).
Notice of Reasons for Rejection for Japanese Patent Application No. 2011-534756, mailed Oct. 29, 2013 (10 pages) (English Language Translation Included).
Nummi et al., "Effect of hemolysis and clotting on proton relaxation times of blood." Acta Radiolog Diag. 27(2): 225-30 (1986).
Office Action for Chinese Application No. 201280044411.X, mailed Jan. 6, 2015 (22 pages).
Pell et al., "Optimized clinical T2 relaxometry with a standard CPMG sequence," J Magn Reson Imaging. 23(2):248-52 (2006).
Perez et al., "Magnetic relaxation switches capable of sensing molecular interactions." Nature Biotechnol. 20(8): 816-20 (2002).
Perez et al., "DNA-based magnetic nanoparticle assembly acts as a magnetic relaxation nanoswitch allowing screening of DNA-cleaving agents." J Am Chem Soc. 124(12):2856-7 (2002).
Perez et al., "Use of magnetic nanoparticles as nanosensors to probe for molecular interactions." Chembiochem. 5(3):261-4 (2004).
Perez et al., "Viral-induced self assembly of magnetic nanoparticles allows the detection of viral particles in biological media." J Am Chem Soc. 125(34):10192-3 (2003).
Schuhmacher et al., "NMR relaxation times T1 and T2 of water in plasma from patients with lung carcinoma: correlation of T2 with blood sedimentation rate," Magn Reson Med. 5(6):537-47 (1987).
Sezginer et al., "Very rapid simultaneous measurement of nuclear magnetic resonance spin-lattice relaxation time and spin-spin relaxation time." J Magn Reson. 92:504-27 (1991).
Shapiro et al., "Dynamic imaging with MRI contrast agents: quantitative considerations." Magn Reson Imaging. 24(4):449-62 (2006).
Sillerud et al., "1 H NMR detection of superparamagnetic nanoparticles at 1 T using a microcoil and novel tuning circuit." J Magn Reson. 181(2):181-90 (2006).
Spero et al., "Nanoparticle diffusion measures bulk clot permeability." Biophysical J. 101:1-8 (2011).
Stuhlmuller et al., "Effect of varying fibrinogen and hematocrit concentrations on magnetic resonance relaxation times of thrombus." Invest Radiol. 27(5):341-5 (1992).
Stuhlmuller et al., "Magnetic resonance characterization of blood coagulation in vitro." Invest Radiol. 26(4):343-7 (1991).
Sun et al., "Experimental study on $T_2$ relaxation time or protons in water suspensions of iron-oxide nanoparticles: waiting time dependence." J Magn Magn Mater. 321(18):2971-5 (2009).
Syms et al., "MEMS Helmholtz coils for magnetic resonance imaging. "J Micromec Microeng. 15(7):S1-9 (2005).
Tellier et al., "Evolution of water proton nuclear magnetic relaxation during milk coagulation and syneresis: structural implications." J Agric Food Chem. 41:2259-66 (1993).
Teyssier et al., "Résonance magnétique—dynamique de la coagulation du sang humain étudiée par dispersion des temps de la relaxation protonique/Magentic resonance—coagulation process for human blood studied by protonic relaxation time dispersion," Comptes Rendus de l'Acad. des Sciences. 299(8):395-8 (1984).
Thulborn et al., "Oxygenation dependence of the transverse relaxation time of water protons in whole blood at high field." Biochim Biophys Acta. 714:265-70 (1982).
Tong et al., "Coating optimization of superparamagnetic iron oxide nanoparticles for high T2 relaxivity." Nano Lett. 10(11):4607-13 (2010).
Tsourkas et al., "Magnetic relaxation switch immunosensors detect enantiomeric impurities." Angew Chem Int Ed Engl. 43(18):2395-9 (2004).
Vidmar et al., "A comparison of the ADC and T2 mapping in an assessment of blood-clot lysability." NMR Biomed. 23(1):34-40 (2009).
Vidmar et al., "An MRI study of the differences in the rate of thrombolysis between red blood cell-rich and platelet-rich components of venous thrombi ex vivo," J Magn Reson Imaging. 34(5):1184-91 (2011).
Vidmar et al., "Discrimination between red blood cell and platelet components of blood clots by MR microscopy." Eur Biophys J. 37(7):1235-40 (2008).
Weissleder et al., "Cell-specific targeting of nanoparticles by multivalent attachment of small molecules." Nat Biotechnol. 23(11):1418-23 (2005).
Written Opinion for International Application No. PCT/US2009/062537, mailed Dec. 23, 2009, (7 pages).
Wu et al., "1 H-NMR spectroscopy on the nanoliter scale for static and on-line measurements." Anal Chem. 66(22):3849-57 (1994).
"Anti-Clotting Agents Explained," <http://www.strokeassociation.org/STROKEORG/LifeAfterStroke/HealthyLivingAfterStroke/ManagingMedicines/Anti-Clotting-Agents-Explained_UCM_310452_Article.jsp#.Vo6FzmfSmig>, retrieved on Jan. 7, 2016 (2 pages).
International Search Report and Written Opinion for International Application No. PCT/US2015/027784, mailed on Jul. 27, 2015 (12 pages).
International Search Report and Written Opinion for International Patent Application No. PCT/US13/73395, mailed Mar. 27, 2014 (16 pages).
Li, Yijia, Thesis: "Determining NMR relaxation times for porous media: Theory, measurement and the inverse problem," Master of Mathematics in Applied Mathematics, University of Waterloo, 2007 (147 pages).
Cines et al., "Clot contraction: compression of erythrocytes into tightly packed polyhedra and redistribution of platelets and fibrin," Blood. 123(10):1596-603 (2014).
Examination Report for Australian Application No. 2012281017, mailed Jul. 7, 2016 (3 pages).
Extended European Search Report for European Application No. 13860819.5, mailed Jun. 30, 2016 (8 pages).
Skewis et al., "T2 magnetic resonance: a diagnostic platform for studying integrated hemostasis in whole blood—proof of concept," Clin Chem. 60(9):1174-82 (2014).

\* cited by examiner

27790 TEG LY30% = 0, 51.4

27846 TEG LY30% = 1.6, 47.9

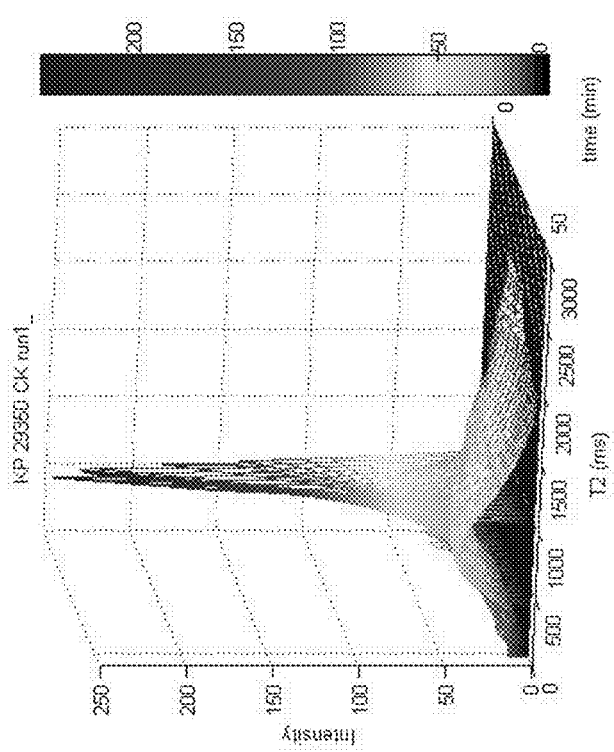
Sample 29350
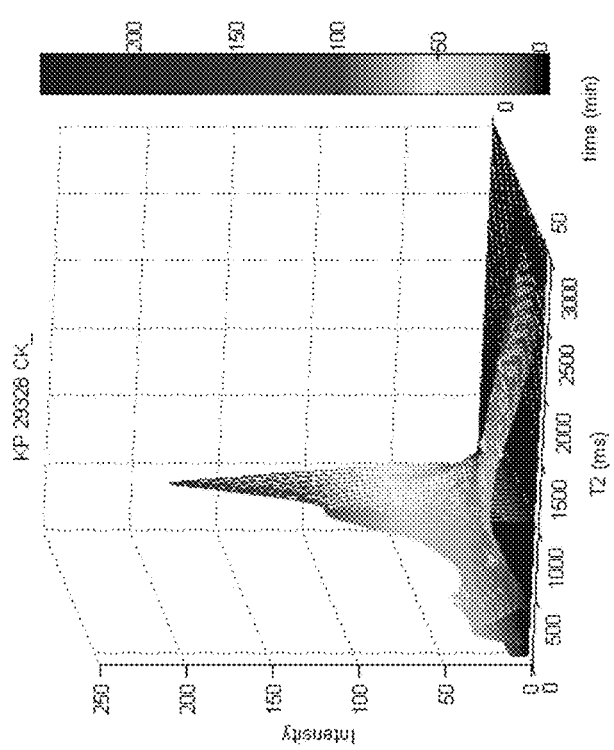
Sample 29328
Fig. 20

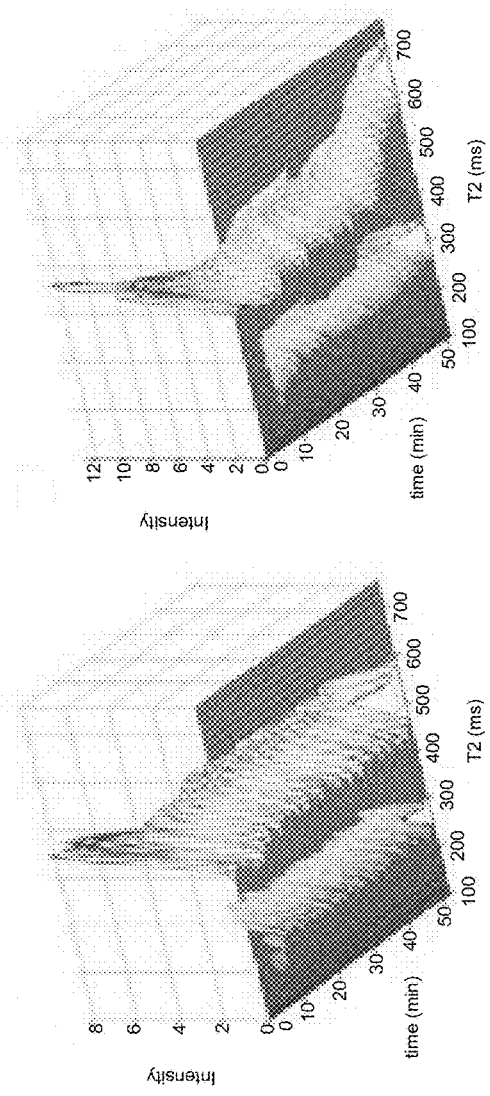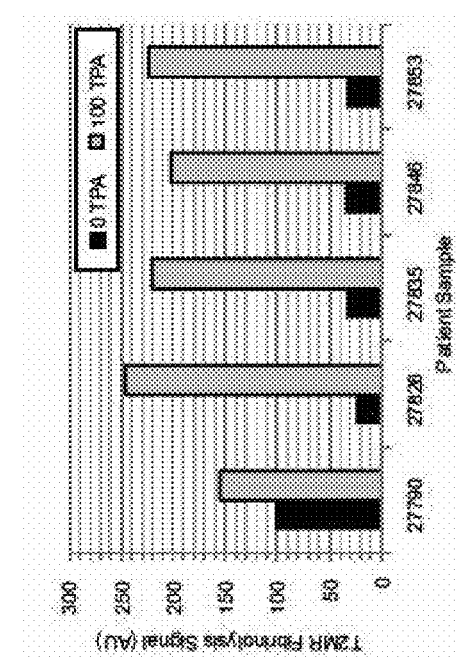

NMR METHODS FOR MONITORING BLOOD CLOT FORMATION

CROSS-REFERENCE TO RELATED APPLICATIONS

This application claims benefit of U.S. Provisional Application No. 61/507,307, filed Jul. 13, 2011; U.S. Provisional Application No. 61/537,396, filed Sep. 21, 2011; U.S. Provisional Application No. 61/538,257, filed Sep. 23, 2011; U.S. Provisional Application No. 61/560,920, filed Nov. 17, 2011; U.S. Provisional Application No. 61/596,445, filed Feb. 8, 2012; and U.S. Provisional Application No. 61/625,945, filed Apr. 18, 2012, all of which are hereby incorporated by reference.

BACKGROUND OF THE INVENTION

The invention features methods for monitoring rheological changes in an aqueous sample.

Blood is the circulating tissue of an organism that carries oxygen and nutritive materials to the tissues and removes carbon dioxide and various metabolic products for excretion. Whole blood consists of a pale yellow or gray yellow fluid, plasma, in which are suspended red blood cells, white blood cells, and platelets.

An accurate measurement of hemostasis, i.e., the ability of a patient's blood to coagulate and dissolve, in a timely and effective fashion is crucial to certain surgical and medical procedures. Accelerated (rapid) and accurate detection of abnormal hemostasis is also of particular importance in respect of appropriate treatment to be given to patients suffering from hemostasis disorders and to whom it may be necessary to administer anti-coagulants, antifibrinolytic agents, thrombolytic agents, anti-platelet agents, or blood components in a quantity which must clearly be determined after taking into account the abnormal components, cells or "factors" of the patient's blood which may be contributing to the hemostasis disorder.

Hemostasis is a dynamic, extremely complex process involving many interacting factors, which include coagulation and fibrinolytic proteins, activators, inhibitors and cellular elements, such as platelet cytoskeleton, platelet cytoplasmic granules and platelet cell surfaces. As a result, during activation, no factor remains static or works in isolation. Thus, to be complete, it is necessary to measure continuously all phases of patient hemostasis as a net product of whole blood components in a non-isolated, or static fashion. To give an example of the consequences of the measuring of an isolated part of hemostasis, assume that a patient developed fibrinolysis, which is caused by the activation of plasminogen into plasmin, an enzyme that breaks down the clot. In this scenario, a byproduct of this process of fibrinogen degrading product behaves as an anticoagulant. If the patient is tested only for anticoagulation and is treated accordingly, this patient may remain at risk due to not being treated with antifibrinolytic agents.

The end result of the hemostasis process is a three-dimensional network of polymerized fibrinogen fibers (i.e., fibrin), which together with platelet glycoprotein IIb/IIIc (GPIIb/IIIa) receptor bonding forms the final clot. A unique property of this network structure is that it behaves as a rigid elastic solid, capable of resisting deforming shear stress of the circulating blood. The strength of the final clot to resist deforming shear stress is determined, in part, by the forces exerted by the participating platelets.

Platelets have been shown to affect the mechanical strength of fibrin in at least two ways. First, by acting as node branching points, they significantly enhance fibrin structure rigidity. Secondly, by exerting a "tugging" force on fibers, by the contractility of platelet actomyosin, a muscle protein that is a part of a cytoskeleton-mediated contractibility apparatus. The force of this contractility further enhances the strength of the fibrin structure. The platelet receptor GPIIb/IIIa appears crucial in anchoring polymerizing fibers to the underlying cytoskeleton contractile apparatus in activated platelets, thereby mediating the transfer of mechanical force.

Thus, the clot that develops and adheres to the damaged vascular system as a result of activated hemostasis and resists the deforming shear stress of the circulating blood is, in essence a mechanical device, formed to provide a "temporary stopper," that resists the shear force of circulating blood during vascular recovery. The kinetics, strength, and stability of the clot, that is its physical property to resist the deforming shear force of the circulating blood, determine its capacity to do the work of hemostasis, which is to stop hemorrhage without permitting inappropriate thrombosis.

Platelets play a critical role in mediating ischemic complications in prothrombotic (thrombophilic) patients. The use of GPIIb/IIIa inhibitor agents in thrombophilic patients or as an adjunct to percutaneous coronary angioplasty (PTCA) is rapidly becoming the standard of care Inhibition of the GPIIb/IIIa receptor is an extremely potent form of antiplatelet therapy that can result in reduction of risk of death and myocardial infarction, but can also result in a dramatic risk of hemorrhage. The reason for the potential of bleeding or non-attainment of adequate therapeutic level of platelet inhibition is the weight-adjusted platelet blocker treatment algorithm that is used in spite of the fact that there is considerable person-to-person variability. This is an issue in part due to differences in platelet count and variability in the number of GPIIb/IIIa receptors per platelet and their ligand binding functions. To be clinically useful, an assay of platelet inhibition must provide rapid and reliable information regarding receptor blockade at the bedside thereby permitting dose modification to achieve the desired anti-platelet effect.

There is a need for a method and apparatus for rapid, reliable, quantitative, point-of-care test for monitoring therapeutic platelet blockade, and for measuring the efficacy of anti-platelet agents, continuously and over the entire hemostasis process from initial clot formation through lysis.

SUMMARY OF THE INVENTION

The invention features a method of monitoring a rheological change in an aqueous sample by: (i) measuring a signal characteristic of the NMR relaxation rate of water in the sample to produce NMR relaxation data; (ii) determining from the NMR relaxation data a magnetic resonance parameter value or set of values being characteristic of the rheological change in the sample; and (iii) comparing the result of step (ii) to a predetermined threshold value.

In a related aspect, the invention features a method of monitoring a rheological change in an aqueous sample including: (i) making a series of magnetic resonance relaxation rate measurements of water in the sample; (ii) transforming the measurements using an algorithm that distinguishes two or more observable water populations within the sample, wherein each observable water population has a distinct relaxation rate and a distinct signal intensity at one or more time points during the rheological change; and (iii)

on the basis of the relaxation rate or signal intensity for at least one of the two or more observable water populations, monitoring the rheological change in the sample.

The invention further features a method of monitoring a rheological change in an aqueous sample including: (i) making a series of measurements of water in the sample, wherein the measurements distinguish two or more observable water populations within the sample, and each observable water population has a distinct signal and/or signal intensity at one or more time points during the rheological change; and (ii) on the basis of the signal and/or signal intensity observed for at least one of the two or more observable water populations, monitoring the rheological change in the sample. The measurements can be nuclear magnetic resonance measurements, electron paramagnetic resonance, microwave spectroscopy measurements, or any other technique known in the art for measuring a property of water. In particular embodiments, the water in the aqueous sample is radiolabeled (e.g., labeled with deuterium or tritium).

In one aspect, the invention features a method of monitoring a clotting or dissolution process in a first blood sample including: (i) making a series of magnetic resonance relaxation rate measurements of water in the first blood sample; (ii) transforming the measurements using an algorithm that distinguishes two or more separate water populations within the first blood sample, wherein each separate water population is characterized by one or more magnetic resonance parameters having one or more values; and (iii) on the basis of the results of step (ii), monitoring the process. The blood sample can be a plasma sample, a platelet poor plasma sample, a platelet rich plasma sample, a blood sample including isolated and washed platelets, a whole blood sample, a clotted blood sample, or any other type of blood sample described herein. In certain embodiments of the method, prior to step (i), to the first blood sample is added fibrinogen (e.g., 1±0.25, 2±0.5, 3±0.75, 4±1, 6±2, or 8±2 mg/mL). In particular embodiments of the method, prior to step (i), to the first blood sample is added a clotting initiator or a clotting inhibitor. The clotting initiator/inhibitor can be selected from RF (reptilase and factor XIII), AA (arachidonic acid), ADP (adenosine diphosphate), CK (kaolin clay), TRAP (thrombin receptor activating peptide), thrombin, platelet aggregation inhibitors, or any clotting initiator or clotting inhibitor described herein. In still other embodiments of the method, prior to step (i), to the first blood sample is added tissue plasminogen activator (TPA). The method can further include the steps of: (iv) making a series of second relaxation rate measurements of water in a second blood sample from the subject; (v) transforming the second relaxation rate measurements using an algorithm that distinguishes two or more separate water populations within the second blood sample, wherein each separate water population is characterized by one or more magnetic resonance parameters, wherein each magnetic resonance parameter has one or more values; and (vi) on the basis of the results of step (ii) and step (v), monitoring the process. For example, the first blood sample can be a plasma sample and the second blood sample can be a whole blood sample; the first blood sample can be a platelet rich plasma sample and the second blood sample can be a whole blood sample; the first blood sample can be a platelet poor plasma sample and the second blood sample can be a whole blood sample; the first blood sample can include isolated and washed platelets and the second blood sample can be a whole blood sample, or any other set of comparative samples described herein. In particular embodiments, prior to step (i), to the first blood sample is added platelet inhibitor, and no platelet inhibitor is added to the second blood sample; prior to step (i), to the first blood sample is added platelet activator, and no platelet activator is added to the second blood sample; or prior to step (i), to the first blood sample is added a clotting initiator selected from RF, AA, and CK; and prior to step (iv), to the second blood sample is added a clotting initiator selected from ADP and thrombin. In certain embodiments of the method, prior to step (i), to the first blood sample is added fibrinogen (e.g., 1±0.25, 2±0.5, 3±0.75, 4±1, 6±2, or 8±2 mg/mL); and prior to step (iv), to the second blood sample is added fibrinogen (e.g., 1±0.25, 2±0.5, 3±0.75, 4±1, 6±2, or 8±2 mg/mL).

In the above method, the magnetic resonance parameter value can be characteristic of functional fibrinogen-associated water molecules in the blood sample. In particular embodiments, at least one of the two or more separate water populations is positively correlated with platelet activation, platelet inhibition, clotting time, platelet-associated clot strength, hematocrit, or fibrinogen-associated clot strength. In still other embodiments, the magnetic resonance parameter values indicate a low platelet activity, a high platelet activity, a high functional fibrinogen activity, or a low functional fibrinogen activity.

In any of the above methods, the algorithm can include an algorithm selected from the group consisting of a multi-exponential algorithm, a bi-exponential algorithm, a tri-exponential algorithm, a decaying exponential algorithm, a Laplace transform, a goodness-of-fit algorithm, an SSE algorithm, a least squares algorithm, a non-negative least squares algorithm, or any algorithm described herein. In particular embodiments, the algorithm is an inverse Laplace transform.

In any of the above methods, the relaxation rate can be selected from the group consisting of T1, T2, T1/T2 hybrid, $T_{1rho}$, $T_{2rho}$, and $T_2^*$. In one particular embodiment, the relaxation rate measurements include a T2 measurement, and the measurement provides a decay curve.

In another particular embodiment, the two or more water populations include a water population having a serum-associated T2 signal and water population having a clot-associated T2 signal. The method can include (i) calculating the T2 value for serum associated water prior to initiating clot formation in a blood sample including red blood cells, and on the basis of the T2 value, determining the hematocrit of the blood sample. The method can also include (a) calculating the difference between the serum-associated T2 signal and the clot-associated T2 signal for a blood sample undergoing a clotting process; and (b) on the basis of the difference, determining the strength of the clot formed in the blood sample. The method may include (a) calculating the difference between the serum-associated T2 signal and the clot-associated T2 signal for a blood sample including platelets and undergoing a clotting process; and (b) on the basis of the difference, determining the activity of the platelets in the blood sample. In one embodiment the method further includes (a) following initiation of a clotting process in a blood sample, measuring the period of time prior to the initial detection of the clot-associated T2 signal; and (b) on the basis of the period of time, determining the clotting time for the blood sample. In other embodiments the method further includes (a) following initiation of a clotting process in a blood sample, calculating a T2 time curve for the serum-associated T2 signal; (b) calculating the maximum value of the second derivative of the T2 time curve; and (c) on the basis of the result of step (b), calculating a value characteristic of clotting time. In still other embodiments the method includes, following initiation of a clotting process in a blood sample, on the basis of the serum-associated T2 signal and the clot-associated T2 signal, determining whether the blood sample is hypercoagulable, hypocoagulable, or normal.

In one embodiment of any of the above methods, the method further includes calculating from the decay curve a T2 relaxation spectrum at a predetermined time point following initiation of the clotting or dissolution process. The method can further include, following initiation of a clotting or dissolution process in a blood sample, (a) making a plurality of relaxation rate measurements on the blood sample during the process to produce a plurality of decay curves, and (b) calculating from the plurality of decay curves a plurality of T2 relaxation spectra. Optionally, the method further includes calculating from the plurality of T2 relaxation spectra a 3 dimensional data set depicting (a) the change in T2 relaxation times and (b) the change in T2 signal intensity for two or more water populations in the blood sample as a function of time following initiation of a clotting or dissolution process in the blood sample.

In particular embodiments, the method further includes (i) partitioning the 3 dimensional data set into stable data and transitional data and (ii) on the basis of the stable data and the transitional data, determining whether the blood sample is hypercoagulable, hypocoagulable, or normal, or determining whether the blood sample exhibits a low platelet activity, a high platelet activity, a high functional fibrinogen activity, or a low functional fibrinogen activity. In certain embodiments, the method further includes (i) calculating from a 3 dimensional data set the relative volume of signal observed for each of two or more water populations in the blood sample over a predetermined time period during the process, and (ii) on the basis of the relative volume of signal, determining whether the blood sample is hypercoagulable, hypocoagulable, or normal, or determining whether the blood sample exhibits a low platelet activity, a high platelet activity, a high functional fibrinogen activity, or a low functional fibrinogen activity.

In another particular embodiment of any of the above methods, the algorithm is an inverse Laplace transform that includes a lower bound for the T2 time constants of from 1 to 50 ms (e.g., 1 to 10, 1 to 20, 1 to 30, 5 to 50, 5 to 30, or 10 to 50 ms) and an upper bound for the T2 time constants of from 1000 to 4000 ms (e.g., 1000 to 2000, 2500 to 4000, 1000 to 3000, 1500 to 4000, 2000 to 4000, or 2000 to 4000 ms). For example, the blood sample can be plasma, platelet poor plasma, or platelet rich plasma and the upper bound for the T2 time constants is from 2500 to 4000 ms (e.g., 2500 to 3500, 2500 to 3000, 3000 to 4000, or 3500 to 4000 ms). In other embodiments, the blood sample is a whole blood sample, a sample that includes red blood cells, or a sample that includes magnetic particles and the upper bound for the T2 time constants is from 1000 to 2000 ms (e.g., 1500 to 2000, 1000 to 1500, or 1000 to 1200 ms). In still another particular embodiment of any of the above methods, the algorithm is an inverse Laplace transform that includes a regularization parameter ($\alpha$) in the range of from about 1.0e-10 to about 4.0e0.

The invention further features a method for assessing the hemostatic condition of a subject, the method including: (i) providing a blood drawn from the subject to produce a blood sample; (ii) making a series of magnetic resonance relaxation rate measurements of water in the blood sample; (iii) transforming the measurements using an algorithm that distinguishes two or more separate water populations within the blood sample to produce one or more magnetic resonance parameter values according to the methods of the invention; and (iv) on the basis of the results of step (iii), determining whether the subject is normal, has a hemorrhagic condition, or a has a prothrombotic condition.

In a related aspect, the invention features a method of assessing platelet activity including: (i) providing isolated and washed platelets; (ii) combining the isolated and washed platelets with platelet poor plasma including a predetermined minimum level of fibrinogen to form a test sample; (iii) initiating a clotting process by adding a clotting initiator to the test sample; (iv) making a series of magnetic resonance relaxation rate measurements of water in the test sample; (v) transforming the measurements using an algorithm that distinguishes two or more separate water populations within the test sample, wherein each separate water population is characterized by one or more magnetic resonance parameters having one or more values; and (vi) on the basis of the results of step (v), assessing the platelet activity. In particular embodiments the clotting initiator is a combination of RF and AA. In still other embodiments, the method further includes (a) measuring the test sample in the presence of a platelet activator and in the absence of a platelet activator.

The invention further features a method of assessing platelet activity in a whole blood sample including: (i) providing a whole blood sample; (ii) combining the isolated and washed platelets with platelet poor plasma including a predetermined minimum level of fibrinogen to form a test sample; (iii) initiating a clotting process by adding a clotting initiator to the test sample; (iv) making a series of magnetic resonance relaxation rate measurements of water in the test sample; (v) transforming the measurements using an algorithm that distinguishes two or more separate water populations within the test sample, wherein each separate water population is characterized by one or more magnetic resonance parameters having one or more values; and (vi) on the basis of the results of step (v), assessing the platelet activity. In particular embodiments the clotting initiator is a combination of RF and AA. In still other embodiments, the method further includes (a) measuring the test sample in the presence of a platelet activator and in the absence of a platelet activator.

In another aspect, the invention features a method of monitoring a clotting process or dissolution process by measuring a signal characteristic of the NMR relaxation rate of water in a sample undergoing clotting of dissolution to produce NMR relaxation data and determining from the NMR relaxation data a magnetic resonance parameter value or set of values characteristic of the clotting or dissolution process in the sample.

In a related aspect, the invention features a method of monitoring a clotting process or dissolution process by measuring a signal characteristic of the NMR relaxation of water in a blood sample having one or more populations of water to produce NMR relaxation data, and determining from the NMR relaxation data a magnetic resonance parameter value or set of values correlated to at least one population of water in the blood sample, where the magnetic resonance parameter value or set of values is characteristic of the clotting or dissolution process. The blood sample can include at least two populations of water or at least three populations of water. In particular embodiments, the magnetic resonance parameter values are characteristic of platelet-associated water molecules in the blood sample. In still other embodiments, the magnetic resonance parameter values are characteristic of functional fibrinogen-associated water molecules in the blood sample. In particular embodiments of the claimed methods, the method includes measuring the relative concentration of platelet-associated functional fibrinogen.

In certain embodiments, the method includes assessing the hemostatic condition of a subject based upon the clotting behavior of a single blood sample drawn from the subject (e.g., for coagulation management of a patients undergoing surgery, to identify a patient at risk of thrombotic complications, to identify a patient resistant to antiplatelet therapy, to monitor anticoagulation therapy in a patient, to monitor antiplatelet therapy in a patient, and/or to monitor procoagulant therapy in a patient).

In still other embodiments of the invention, the method includes assessing the hemostatic condition of a subject within 3 minutes, 5 minutes, 6 minutes, 10 minutes, 15 minutes, 20 minutes, 30 minutes, 45 minutes, or 60 minutes of collecting the initial NMR relaxation rate signal from the sample.

In a related aspect, the invention features a method of monitoring a blood clotting process or dissolution process by: (i) making a series of relaxation rate measurements of the water in a blood sample; (ii) transforming the measurements using an algorithm that distinguishes two or more separate water populations within the blood sample, where each separate water population is characterized by one or more magnetic resonance parameters having one or more values; and (iii) on the basis of the results of step (ii), monitoring the blood clotting process in the blood sample.

The invention features a method of monitoring platelet activity including: (i) making a series of relaxation rate measurements of the water in a blood sample; (ii) transforming the measurements using an algorithm that distinguishes two or more separate water populations within the blood sample, wherein each separate water population is characterized by one or more magnetic resonance parameters having one or more values; and (iii) on the basis of the results of step (ii), monitoring the platelet activity in the blood sample.

The invention further features a method of monitoring platelet inhibition including: (i) making a series of relaxation rate measurements of the water in a blood sample; (ii) transforming the measurements using an algorithm that distinguishes two or more separate water populations within the blood sample, wherein each separate water population is characterized by one or more magnetic resonance parameters having one or more values; and (iii) on the basis of the results of step (ii), monitoring the platelet inhibition in the blood sample. In particular embodiments, the method further includes: (iv) making a series of relaxation rate measurements of the water in a second blood sample in the presence of a platelet inhibitor; (v) transforming the measurements using an algorithm that distinguishes two or more separate water populations within the second blood sample, wherein each separate water population is characterized by one or more magnetic resonance parameters having one or more values; and (vi) on the basis of the results of steps (ii) and (v), monitoring the platelet inhibition in the blood sample.

The invention also features a method of assessing the hemostatic condition of a subject by: (i) making a series of relaxation rate measurements of the water in a blood sample from the subject; (ii) transforming the measurements using an algorithm that distinguishes two or more separate water populations within the blood sample, where each separate water population is characterized by one or more magnetic resonance parameters having one or more values; and (iii) on the basis of the results of step (ii), assessing the hemostatic condition of the subject.

The algorithm can be, without limitation, selected from a multi-exponential algorithm, a bi-exponential algorithm, a tri-exponential algorithm, a decaying exponential algorithm, a Laplace transform, a goodness-of-fit algorithm, an SSE algorithm, a least-squares algorithm, a non-negative least-squares algorithm, and any other algorithm described herein. In particular embodiments, the algorithm is an inverse Laplace transform or the algorithm is given by equations (1) (i.e., for a biexponential fit) or (2) (i.e., for a triexponential fit).

$$I = \text{Amp}_A \exp^{(-t/T2A)} + \text{Amp}_B \exp^{(-t/T2B)} + O \quad (1)$$

$$I = \text{Amp}_A \exp^{(-t/T2A)} + \text{Amp}_B \exp^{(-t/T2B)} + \text{Amp}_C \exp^{(-t/T2c)} + O \quad (2)$$

In equations (1) and (2), I is the intensity of a measured value T2; t is time; $\text{Amp}_A$ is an extracted coefficient that indicates the degree to which the exponential term $\exp^{(-t/T2A)}$ contributes to a measured T2 intensity; $\text{Amp}_B$ is an extracted coefficient that indicates the degree to which the exponential term $\exp^{(-t/T2B)}$ contributes to a measured T2 intensity; $\text{Amp}_C$ is an extracted coefficient that indicates the degree to which the exponential term $\exp^{(-t/T2C)}$ contributes to a measured T2 intensity; T2A is an extracted relaxation time that indicates the contribution of a water population A to a measured T2 intensity; T2B is an extracted relaxation time that indicates the contribution of a water population B to a measured T2 intensity; T2C is an extracted relaxation time that indicates the contribution of a water population C to a measured T2 intensity; and O is an offset constant. In any of the above methods, the relaxation rate measurements can include a T2 measurement. The magnetic resonance parameter values can include a T2 parameter value and/or an amplitude parameter value.

For a sample undergoing a rheological transition, populations of water can vary, depending on the components and or complexity of the sample. In a heterogeneous sample, for example whole blood, there are different populations of water, e.g. plasma water, compartmentalized water, i.e. cellular (erythrocyte, leukocyte, and thrombocyte) water, and water associated with functional features of whole blood processes such as coagulation, e.g. serum, or clot dissolution. The methods of the invention allow one to monitor changes in the various water populations in a sample, regardless of location, compartment, or the changes occurring within the sample. The methods can be used to examine changes in rheology, or to calculate one or more analytical values (aPPT, PT-INR, hematocrit, platelet activity) for a given sample.

In any of the above methods, the water in the sample can include a first water population and a second water population, and an NMR parameter associated with a given water population can be correlated with a rheological change. For example, NMR parameter values of the second water population could be positively correlated with platelet activation. Similarly, T2 parameter values for the first water population could be correlated with the coagulation time.

In any of the above methods, the magnetic resonance parameter values can include a T2 value for the first water population that is between 250 and 500 milliseconds.

In any of the above methods, the magnetic resonance parameters values can include a T2 value for the second water population that is between 100 and 300 milliseconds.

In any of the above methods, the sample can further include a third water population having a T2 value of between 1 and 10 milliseconds.

In any of the above methods, the signal arises from monitoring protons in water or monitoring hydrogen atoms in water. Alternatively, in any of the above methods, the signal arises from monitoring protons in water or monitoring oxygen atoms in water.

In some embodiments of the invention, a blood sample contains a fourth water population and a fifth water population, where the fourth water population is associated with a retracted blood clot, and the fifth water population is associated with the serum surrounding the retracted clot. The presence of the fourth and/or fifth water population does not either imply the presence or require the presence of the first, second, or third water populations, as defined herein.

In any of the above methods, the method can further include, on the basis of the magnetic resonance parameter value or set of values, assessing whether the sample is hypercoagulable, hypocoagulable, or normal.

In any of the above methods, the magnetic resonance parameter can be characteristic of a hemostatic condition in a subject (e.g., a hemorrhagic condition or a prothrombotic condition). For example, the magnetic resonance parameter can be indicative of low platelet activity; indicative of high platelet activity; indicative of a high functional fibrinogen activity; or indicative of a low functional fibrinogen activity.

In particular embodiments of the invention, a paramagnetic agent (e.g., manganese, manganese complexes, gadolinium, gadolinium complexes, or magnetic particles) is added to the blood sample prior to measuring the signal characteristic of the NMR relaxation parameters. In a preferred embodiment is a superparamagnetic particle. The paramagnetic agent can be a superparamagnetic particle having an average diameter of between 3 and 40 nanometers, between 30 and 70 nanometers, between 70 and 100 nanometers, between 100 and 500 nanometers, or between 500 and 1000 nanometers. In particular embodiments, the method of the invention is performed on a blood sample from a single patient both in the presence and absence of the paramagnetic agent.

In another embodiment of the methods of the invention, the sample being analyzed has a volume between 2 μL and 400 μL (e.g., from 2 μL to 10 μL, 10 μL to 20 μL, 15 μL to 50 μL, 50 μL to 100 μL, 100 μL to 250 μL, or from 200 μL to 500 μL). In still other embodiments, the sample being analyzed has a volume between 400 μL and 4000 μL.

In any of the above methods, the NMR relaxation data is selected from T1, T2, T1/T2 hybrid, $T_{1rho}$, $T_{2rho}$ and $T_2^*$ data. Additionally, apparent diffusion coefficient (ADC) can be determined and evaluated (see Vidmar et al. NMR in BioMedicine, 2009; and Vidmar et al., Eur J Biophys J. 2008). Additionally, the methods of the invention can utilize pulsed field gradients (i.e., with measurement of echo attenuation as a function if the square of gradient strength), Hahn echo sequence, spin echo sequence, and/or FID signal ratios.

The invention features a magnetic resonance device for monitoring a blood clotting process, wherein the device includes a microprocessor with an algorithm that distinguishes two or more separate water populations within the blood sample, wherein each separate water population is characterized by a magnetic resonance parameter value or set of values. The algorithm can be, without limitation, selected from a multi-exponential algorithm, a bi-exponential algorithm, a tri-exponential algorithm, a decaying exponential algorithm, a Laplace transform, a goodness-of-fit algorithm, an SSE algorithm, a least-squares algorithm, a non-negative least-squares algorithm, and any other algorithm described herein.

In a related aspect the invention features a method for monitoring the dissolution of a blood clot including: (i) providing a clotted blood sample; (ii) combining the clotted blood sample with tissue plasminogen factor (TPA); (iii) making a series of relaxation rate measurements of the water in the clotted blood sample; (iv) transforming the measurements using an algorithm that distinguishes two or more separate water populations within the blood sample, wherein each separate water population is characterized by one or more magnetic resonance parameters having one or more values; and (v) on the basis of the results of step (iv), monitoring the dissolution of the clotted blood.

In certain embodiments, the hemostatic condition of a subject is assessed on the basis of a blood clotting behavior of a blood sample drawn from the subject. Examples of clotting behavior include clotting time (R), clot strength (MA), platelet-associated clot strength ($MA_{PLATELET}$), functional fibrinogen-associated clot strength ($MA_{FF}$), and percent lysis 30 minutes after MA (LY30). Examples of hemostatic conditions include prothrombotic, hemorrhagic, and normal conditions. A clotting behavior or hemostatic condition may be established within a certain timeframe after collection of the initial NMR relaxation data (e.g., within 10, 6, or 3 minutes). Moreover, in establishing the clotting behavior, one more additives (e.g., fibrinogen or TPA) may be added to the sample.

In other embodiments, a blood clotting process of the blood drawn from a subject is monitored by: (i) making a series of first relaxation rate measurements of the water in a first blood sample (e.g., a sample treated with an additive) from the subject; (ii) transforming the first relaxation rate measurements using an algorithm that distinguishes two or more separate water populations within the first blood sample; (iii) making a series of second relaxation rate measurements of the water in a second blood sample (e.g., an untreated sample) from the subject; (iv) transforming the second relaxation rate measurements using an algorithm that distinguishes two or more separate water populations within the second blood sample, where each separate water population is characterized by one or more magnetic resonance parameters, where each magnetic resonance parameter has one or more values; and (v) on the basis of the results of step (iv), monitoring the clotting process of the blood from the subject. One of the samples (e.g., the first sample) may contain an additive such as fibrinogen or tissue plasminogen activator. In some embodiments, the hemostatic condition of the subject is assessed or diagnosed based on the results of the monitoring process (e.g., the hemostatic condition is assessed within 10, 6, or 3 minutes).

In other embodiments, the invention features methods of diagnosing a hemostatic condition in a subject by: (i) providing a blood sample of the subject; (ii) measuring a signal characteristic of the NMR relaxation rate of water in the blood sample to produce one or more values of a magnetic resonance parameter; and (iii) diagnosing the subject on the basis of the results of step (ii). The diagnosis may be based on the comparison of the magnetic resonance parameter value (or values) to a predetermined threshold value (or values). The predetermined threshold values may represent a certain hemostatic condition (e.g., normal, prothrombotic, or hemorrhagic). The hemostatic condition may be assessed within a certain time of collecting the initial NMR relaxation rate signal (e.g., within 10, 6, or 3 minutes).

In certain embodiments, clotting behaviors are assessed using well-defined data extraction methods. The clotting time (R) of a sample can be assessed from a set of collected NMR relaxation rate data by: (i) calculating a T2 time curve for a first water population; (ii) calculating the maximum value of the second derivative of the T2 time curve; and (iii)

on the basis of the result of step (ii), calculating a value characteristic of clotting time (R). The platelet-associated clot strength ($MA_{PLATELET}$) of a sample can be assessed by: (i) calculating a T2 time curve for a first water population; (ii) calculating the slope of a line that connects the initial value of T2 on the T2 curve and the minimum value of T2 on the T2 curve; and (iii) on the basis of the result of step (ii), calculating a value characteristic of the platelet-associated clot strength ($MA_{PLATELET}$) of the sample. The functional fibrinogen-associated clot strength ($MA_{FF}$) of a sample can be assessed by: (i) calculating a first amplitude time curve for a first water population in a first sample that has been treated with fibrinogen; (ii) calculating a second amplitude time curve for a first water population in a second, untreated, sample; (iii) calculating the difference between the first amplitude time curve and the second amplitude time curve; and (iv) on the basis of the result of step (iii), calculating a value characteristic of the functional fibrinogen-associated clot strength ($MA_{FF}$) of the sample. The percent lysis 30 minutes after MA (LY30) of a sample can be assessed by: (i) calculating a first T2 time curve for a second water population in a first sample that has been treated with TPA; (ii) calculating a second T2 time curve for a second water population in a second, untreated, sample; (iii) calculating the difference between the first T2 time curve and the second T2 time curve; and (iv) on the basis of the result of step (iii), calculating a value characteristic of the percent lysis 30 minutes after MA (LY30) of the sample.

In other embodiments, a T2 signature curve is used to assess or diagnose the hemostatic condition of a subject by: (i) measuring a signal characteristic of the NMR relaxation of water in a blood sample drawn from the subject to produce NMR relaxation data; and (ii) determining from the NMR relaxation data a T2 signature that is characteristic of the hemostatic condition of the subject. The T2 signature can be compared with a standard or set of standard curves to establish the hemostatic condition of the subject.

In other embodiments, the invention features a method of monitoring a water-containing material, by: (i) providing a water-containing material that capable of transitioning from a liquid fluid state to a gel state; (ii) measuring a series of signals characteristic of the NMR relaxation of water in the material to produce NMR relaxation data; and (iii) determining from the NMR relaxation data a time curve that is characteristic of the water-containing material. In some embodiment, the time curve is a relaxation curve other than a T2 relaxation curve, such as a T1 time curve, a T2 time curve, or a hybrid T1/T2 time curve. In related embodiment, the water-containing material is whole blood, a polyacrylamide hydrogel, a polyvinylpyrrolidone hydrogel, a polyethylene glycol hydrogel, a polyvinylalcohol hydrogel, a polyacrylic acid hydrogel, carrageenan gel, alginate gel, or gelatin. In a preferred embodiment, the water-containing material is an acrylamide hydrogel.

In another aspect, the invention features a method of assessing the calibration state of a blood-monitoring device by: (i) providing a water-containing material that capable of transitioning from a liquid fluid state to a gel state; (ii) using the blood-monitoring device to measure a characteristic of the water-containing material; and (iii) assessing the calibration state of the blood-monitoring device by comparing the characteristic produced in step (ii) to a predetermined threshold value. In preferred embodiments, the water-containing material is an acrylamide gel and the blood-monitoring device is a T2reader or thromboelastography (TEG) analyzer. In specific embodiments, a paramagnetic agent (e.g., manganese, manganese complexes, gadolinium, gadolinium complexes, or superparamagnetic particles) is added to the sample prior to analysis. The paramagnetic agent can be a superparamagnetic particle having an average diameter of between 3 and 40 nanometers, between 30 and 70 nanometers, between 70 and 100 nanometers, between 100 and 500 nanometers, or between 500 and 1000 nanometers.

In certain embodiments, a series of NMR relaxation rate measurements from a blood sample is used to generate a series of magnetic resonance parameter values (e.g., T2 or amplitude values) that is characteristic of a certain water population in the blood sample. The series of magnetic resonance parameters values can be plotted as a function of time to generate a time curve that is also characteristic of the water population. For example, a T2 time curve (or an amplitude curve) for a certain water population in a blood sample can be plotted as the sample undergoes clotting. These time curves may be further used to generate additional curves. For example, a first or a second time derivative of a T2 time curve can be plotted. Time curves can be used as the basis for assessing a clotting behavior of a blood sample or the hemostatic condition of the subject from whom the blood sample was drawn. Similarly, curves generated from two different samples obtained from the same subject (e.g., a treated sample and an untreated sample) can be used as the basis for assessing a clotting behavior of the subject's blood or the hemostatic condition of the subject.

In other embodiments, a clotting behavior of a sample or the hemostatic condition of a subject can be assessed on the basis of comparing the value of a magnetic resonance parameter or time curve associated with the sample or subject to a predetermined threshold value. The predetermined threshold value can be established in a number of different ways. For example, the predetermined threshold can be characteristic of a hemostatic condition (e.g., a normal, prothrombotic, or hemorrhagic condition). The threshold value can be determined from mean values, or the range of values observed for blood drawn from normal and abnormal subjects. Alternatively, the threshold value can be determined from a standard sample that consistently provides the same parameter or curve when used in the NMR-based methods of the invention (e.g., a blood sample treated to clot in a particular manner or an acrylamide gel).

In another aspect, the invention features a method of assessing the hemostatic condition of a subject by: (i) making a series of relaxation rate measurements (e.g., T2 relaxation rate measurements) of the water in a blood sample drawn from the subject, where the blood sample is undergoing a clotting process or a dissolution process, and where the measurements provide two or more decay curves, where each decay curve is characteristic of a time point in the process; (ii) applying a mathematical transform (e.g., an inverse Laplace transform) to the two or more decay curves to identify two or more water populations (e.g., a water population having a serum-associated T2 signal and a water population having a clot-associated T2 signal) in the blood sample at two or more time points in the process to produce two or more magnetic resonance parameter values having two or more signal intensities, where each water population has a characteristic magnetic resonance parameter value and a concentration characteristic of the signal intensity of the magnetic resonance parameter value; (iii) producing a 3D data set from (a) the two or more time points; (b) the two or more magnetic resonance parameter values; and (c) the two or more signal intensities; (iv) extracting from the 3D data set one or more clotting behaviors (e.g., clotting time (R), fibrinolytic behavior, clot strength (MA), kinetic behavior of the clot, platelet-associated clot strength ($MA_{PLATELET}$), functional fibrinogen-associated clot strength ($MA_{FF}$), percent lysis 30 minutes after MA (LY30), or hematocrit) that is characteristic of the hemostatic condition of the subject; and (v) assessing the hemostatic condition of the subject on the basis of the one or more clotting behaviors.

In certain embodiments, the invention features adding an anti-platelet antibody or Fab fragment (e.g., abciximab) to a sample (e.g., a whole blood sample) undergoing a clotting process or a dissolution process. In other embodiments, the invention features adding a clotting activator or a platelet inhibitor to a sample (e.g., a whole blood sample) undergoing a clotting process or a dissolution process.

In another aspect, the invention features a method of assessing the strength of a blood clot or the platelet activity of a blood clot by: (i) making a T2 relaxation rate measurement of the water in a blood clot, where the measurement provides a decay curve; (ii) applying a mathematical transform (e.g., an inverse Laplace transform) to the decay curve to identify the signal intensity of a water population in the blood clot, wherein the water population corresponds to a retracted blood clot water environment or a serum water environment; and (iii) on the basis of the signal intensity of the water population, assessing the strength of the blood clot or the platelet activity of the blood clot.

In another aspect, the invention features a method of assessing the hemostatic condition of a subject by: (i) providing a blood sample from the subject; (ii) making a T2 relaxation rate measurement of the water in the sample, where the measurement provides a decay curve; (iii) applying a mathematical transform (e.g., an inverse Laplace transform) to the decay curve to identify a serum-associated T2 signal and a clot-associated T2 signal; and (iv) on the basis of the difference between the serum-associated T2 signal and the clot-associated T2 signal or the appearance of the clot-associated T2 signal assessing the hemostatic condition of the subject.

In another aspect, the invention features a method of diagnosing a hemostatic condition in a subject by: (i) making a series of NMR relaxation rate measurements of the water in a blood sample drawn from the subject; (ii) transmitting the NMR relaxation rate measurements or data that is characteristic of the NMR relaxation rate measurements for processing, the processing including any of the methods described herein; and (iii) receiving the results of step (ii) and, on the basis of the results, diagnosing the subject.

The invention further features a method for reducing the risk of bleeding or clotting in a subject fitted with a heart assist device, the method including: (i) evaluating the hemostatic condition of the subject using a method described herein; and (ii) on the basis of step (i), adjusting an operational parameter (e.g., speed, intensity, pressure, flow, pump volume, or filling volume) of the heart assist device to reduce the risk of bleeding or clotting in the subject. In particular embodiment, the heart assist device is selected from an extracorporeal cardiac bypass machines and implantable blood pumps, such as left ventricular assist devices.

The invention further features a method for reducing the risk of bleeding or clotting in a subject fitted with a heart assist device, the method including: (i) evaluating the hemostatic condition of the subject using a method described herein; and (ii) on the basis of step (i), administering an anticoagulation therapy, antiplatelet therapy, and/or procoagulant therapy to the subject to reduce the risk of bleeding or clotting in the subject. In particular embodiment, the heart assist device is selected from an extracorporeal cardiac bypass machines and implantable blood pumps, such as left ventricular assist devices.

In another aspect, the invention features a method of comparing a clotting or dissolution behavior of a sample measured using the NMR-based techniques of the invention with rheological change or clotting or dissolution measured in an equivalent sample using a system known in the art.

The methods of the invention can be used to make simultaneous measures of multiple parameters in a sample (e.g., simultaneously measure parameters associated with the clotting of a sample or the hemostatic condition of a subject).

In any of the above methods, the method can include the steps of (i) adding whole blood, or a component thereof, to a tube containing one or more additives (e.g., heparin, citrate, a nanoparticle formulation, paramagnetic agents, fibrinogen, tissue plasminogen activator (TPA), antithrombotic agents such as abciximab, or any other additive described herein), and (ii) mixing the contents to initiate a clotting process. In particular embodiments, the one or more additives are dried additives reconstitutable in whole blood, or a component thereof. For example, whole blood, or a component thereof, can be caused to clot in situ with a small pellet of collagen on the bottom of the sample tube. In particular embodiments, at least a portion of the sample tube is coated with collagen to initiate clotting. In still other embodiments, a localized region of the sample tube is coated with a clot initiator (e.g., collagen, or another clot initiator described herein) to permit spatial control of the clot formation.

In any of the above methods, the method can include the step of measuring the T2 signal of a sample using a T2reader. For example, quantitative T2 measures in blood (whole blood, diluted blood, PRP, etc.) can be made using a CPMG pulse sequence utilizing long total echo times, with total echo time of about 5×T2 (e.g., tau is typically more than 62.5 µs and less than 1000 µs). In particular embodiments, the T2reader is used to pre-incubate the sample to the desired temperature prior to initiating the clotting process.

For samples containing unclotted blood, it is understood that the unclotted blood can settle to produce a sample with more than one T2 value, but the timescale of this settling is typically longer than that of clot formation.

The methods of the invention are directed to the analysis of raw NMR data to produce information about two or more water populations in a sample undergoing a clotting or dissolution process. Exemplified are inverse Laplace transformations of the data to identify the signal intensities arising from the different water populations observed simultaneously within a sample. Alternatively, information about the two or more water populations in a sample may be obtained using data acquisition and data manipulation techniques known in the art, such as (i) relaxation measurement using a Hahn Echo pulse sequence; (ii) difference measurement based on the difference between the FID signal amplitude at a fixed time delay after the initial 90-degree pulse and the amplitude at a fixed delay after a subsequent 180-degree pulse; (iii) measurement of T2 values and echo attenuations in the presence of a pulsed field gradient configured to attenuate specific populations of water based on their relaxation properties thereby highlighting other populations of water; and (iv) difference measurements (i.e., the difference between the signal intensity at two or more different points in time for (a) an FID after a single 90-degree pulse, (b) a CPMG relaxation curve, (c) a relaxation curve obtained by a series of Hahn echoes or spin echoes, or (d) a CP relaxation curve). The alternative approaches can be used in any of the methods described herein.

As used herein, the term "3D data set" refers to a collection of measured and/or derived data points that can be assembled into a 3D plot that is characteristic of the changes in a sample undergoing a clotting process or dissolution process over a period of time. A 3D plot derived from a 3D data set can depict the emergence and/or disappearance of different water populations within the sample and quantifies the intensities and relaxation times (e.g., T2 relaxation times) of these water populations at specific points in time or over ranges of time.

As used herein, the term "a first water population" refers to a water population of a whole blood sample that is characterized by an initial amplitude in unclotted blood that decreases with clotting. A first water population may also refer to a water population referred to elsewhere in the application as population A. The amplitude and T2 data extracted from a first water population are referred to as $Amp_A$ and T2A, respectively.

As used herein, the term "a second water population" refers to a water population of a whole blood sample that is characterized by an initial amplitude in unclotted blood that increases with clotting. The second water population may be associated with the platelet concentration of a blood clot. A second water population may also refer to a water population referred to elsewhere in the application as population B. The amplitude and T2 data extracted from a second water population are referred to as $Amp_B$ and T2B, respectively.

As used herein, the term "a third water population" refers to a water population of a whole blood sample that is characterized by an approximately constant amplitude during the clotting process. The third water population may be associated with the water bound to biomolecules within red blood cells. A third water population may also refer to a water population referred to elsewhere in the application as population C. The amplitude and T2 data extracted from a third water population are referred to as $Amp_s$ and T2C, respectively.

As used herein, the term "a fourth water population" refers to a water population of a whole blood sample that is characterized by a broad distribution of T2 values, ranging from about 400 milliseconds to about 2,200 milliseconds. The range of T2 values associated with the fourth water population may depend on the hardware and materials (e.g., sample tubes) used in the collection of the data. The fourth water population may be associated with the serum surrounding a retracted blood clot and merge with a fifth water population upon the inclusion of an anti-platelet aggregation agent (e.g., abciximab) in the blood sample. The features of the fourth water population may correspond with platelet activity and/or clot strength.

As used herein, the terms "serum water environment" refers to the water environment found in an unclotted blood sample, or that portion of a blood sample that remains unclotted. The "serum-associated T2 signal" refers to the signal arising from the serum water environment (e.g., a corresponding T2 signal within a clotting blood sample associated with the serum surrounding a retracted blood clot). The serum-associated T2 signal is typically present in both a sample containing a retracted blood clot and a clotted sample from which the retracted blood clot has been removed. The serum-associated T2 signal contains a resolved peak with higher T2 values than the T2 values of the clot-associated T2 signal. The serum water environment can be associated with the fourth water population described above.

As used herein, the term "a fifth water population" refers to a water population of a whole blood sample that is characterized by a distribution of T2 values ranging from about 80 milliseconds to about 500 milliseconds. The range of T2 values associated with the fifth water population may depend on the hardware and materials (e.g., sample tubes) used in the collection of the data. The fifth water population may be associated with a retracted blood clot. The features of the fifth water population may correspond with clotting time and/or fibrinolytic activity.

As used herein, the terms "retracted blood clot water environment" refers to the water environment found in a retracted blood clot and characteristic of clot formation. The "clot-associated T2 signal" refers to the signal arising from the retracted blood clot water environment (whether or not the clot is retracted at the time of measurement). The clot-associated T2 signal is present both in a clotted whole blood sample containing a retracted blood clot and a sample containing a retracted blood clot from which the surrounding serum has been removed. The clot-associated T2 signal contains a resolved peak with lower T2 values than the T2 values of the serum-associated T2 signal. The retracted blood clot water environment can be associated with the fifth water population described above.

As used herein, the term "algorithm" refers to a mathematical routine used to process or transform data.

As used herein, the term "assay" refers to a method of monitoring a blood clotting behavior.

As used herein, the term "clotting behavior" refers to a parameter associated with a blood clot, a forming blood clot, or a clot undergoing dissolution (e.g., clotting time (R), fibrinolytic behavior, clot strength (MA), kinetic behavior of the clot, platelet-associated clot strength ($MA_{PLATELET}$), functional fibrinogen-associated clot strength ($MA_{FF}$), percent lysis 30 minutes after MA (LY30), etc.).

As used herein, the term "clotting process" refers to a process in a liquid resulting in localized spatial change of the solvent water molecules within a sample and characterized by changes in the NMR relaxation rate of solvent water molecules within the aqueous liquid. The aqueous liquid may have more than one population of solvent water molecules, each population characterized by an NMR relaxation parameter that varies as the aqueous sample undergoes the clotting process. The methods of the invention can be used to monitor a clotting process in an aqueous solution containing gel-forming components including, without limitation, proteinaceous solutions (e.g., blood, plasma, or gelatin, among others) and non-proteinaceous hydrogels.

As used herein, the term "dissolution process" refers to a process in a liquid resulting in localized spatial change of the solvent water molecules within a sample and characterized by changes in the NMR relaxation rate of solvent water molecules within the aqueous liquid. The aqueous liquid may have more than one population of solvent water molecules, each population characterized by an NMR relaxation parameter that varies as the aqueous sample undergoes the dissolution process. The methods of the invention can be used to monitor a dissolution process in an aqueous solution containing gel-forming components including, without limitation, proteinaceous solutions (e.g., blood, plasma, or gelatin, among others) and non-proteinaceous hydrogels.

As used herein, the term "functional fibrinogen" refers to fibrinogen in a clot that contributes to the clot strength.

As used herein, the term "gel state" refers to a dispersion including water and a solid in which the mobility of water molecules is reduced in comparison to the mobility of water molecules in a liquid fluid state. The gel state can be formed from polymers and/or proteins (e.g., from clotted blood, from gelatin, or from any gel-forming material described herein).

As used herein, the term "given time after the commencement of the assay" refers to the time within which a clotting behavior may be determined after the start of an assay directed to monitoring blood clotting behavior. Examples of a given time after the commencement of the assay include 60 minutes, 35 minutes, 45 minutes, 10 minutes, 5 minutes, 2 minutes, and 1 minute.

As used herein, the term "heart assist device" includes, but is not limited to, extracorporeal cardiac bypass machines and implantable blood pumps, such as left ventricular assist devices.

As used herein, the term "hematocrit" refers to the percentage, by volume, of red blood cells in a whole blood sample.

As used herein, the term "hemostatic condition" refers to the condition of a subject characterized by the clotting behaviors of the subject's blood. A hemostatic condition may be prothrombotic (an increased risk of blood clot formation), hemorrhagic (an increased risk of spontaneous bleeding), or normal (neither prothrombotic nor hemorrhagic). A hemostatic condition may also refer to a specific thrombotic disorder (e.g., protein C deficiency, protein S deficiency, protein Z deficiency, antithrombin deficiency, antiphospholipid antibody syndrome, resistance to anticoagulation therapy, or hyperhomocysteinuria). In other instances, a hemostatic condition may be induced by an anticoagulant administered to the subject in response to a physiological condition of the subject or to prevent the onset of a physiological condition in the subject. Such physiological conditions include atrial fibrillation, myocardial infarction, unstable angina, deep vein thrombosis, pulmonary embolism, and acute ischemic stroke. Likewise, the hemostatic condition may be induced by administering an anticoagulant to a subject having an invasive surgical procedure, such as joint replacement, surgically-replaced mechanical heart valve or other device implanted in the body. The hemostatic condition of a subject may be assessed by determining one or more clotting behaviors of one or more blood samples drawn from the subject.

As used herein, the term "magnetic resonance parameter" refers to a relaxation rate or amplitude extracted from an NMR relaxation rate measurement.

As used herein, the term "NMR relaxation rate" refers to any of the following in a sample: $T_1$, $T_2$, $T_{1rho}$, $T_{2rho}$, and $T_2^*$. NMR relaxation rates may be measured and/or represented using T1/T2 hybrid detection methods. Additionally, apparent diffusion coefficient (ADC) can be determined and evaluated (Vidmar et al. NMR in BioMedicine, 2009; and Vidmar et al., Eur J Biophys J. 2008).

As used herein, the term "platelet" refers to cellular elements that contribute to clot formation.

As used herein, the term "predetermined threshold value" refers to a standard parameter value or set of values, a standard time curve, or a standard signature curve that is derived from the methods of the invention and is characteristic of a particular rheological state or characteristic of a normal or abnormal result (e.g., characteristic of a blood from a normal subject, or characteristic of blood from a subject having an abnormal hemostatic condition). A predetermined threshold value can be obtained by measuring the NMR parameter values in, for example, blood samples drawn from populations of normal and/or abnormal subjects. The predetermined threshold value can be selected to discriminate between two or more different possible rheological states for a sample. Where the samples are blood samples, the predetermined threshold value can be used, for example, to diagnose a hemostatic condition in the subject.

As used herein, the term "reader" or "T2reader" refers to a device for detecting coagulation-related activation including clotting and fibrinolysis of samples. T2readers may be used generally to characterize the properties of a sample (e.g., a biological sample such as blood or non-biological samples such as an acrylamide gel). Such a device is described, for example, in International Publication No. WO2010/051362, which is herein incorporated by reference.

As used herein, the term "relative concentration" refers to the comparative concentration, or volume fraction, of one water population with respect to another (e.g., a second or third) water population. For example, the relative concentration of water population A may be two times (or five times, or ten times) greater than the concentration of water population B.

As used herein, the term "signal intensity of a water population" refers to the intensity from a relaxation rate measurement for a particular water population in a sample measured as either (i) a peak height characteristic of the particular water population or (ii) an integration of a peak or peaks characteristic of the particular water population.

As used herein, the term "treated sample" refers to a blood sample that contains an additive in a concentration greater than is necessary to prevent coagulation of a normal sample in the absence of a clotting initiator (e.g., calcium chloride).

As used herein, the term "untreated sample" refers to a blood sample that does not contain an additive in a concentration greater than is necessary to prevent coagulation of a normal sample in the absence of a clotting initiator (e.g., calcium chloride).

As used herein, the term "whole blood" refers to the blood of a subject that includes red blood cells. Whole blood includes blood which has been altered through a processing step or modified by the addition of an additive (e.g., heparin, citrate, a nanoparticle formulation, fibrinogen, tissue plasminogen activator (TPA), collagen, antithrombotic agents such as abciximab, or other additives).

As used herein, the term "pooled whole-blood platelets" refers to platelet-enriched blood or blood product (e.g., plasma). Pooled whole-blood platelets include samples that have been altered through a processing step or modified by the addition of an additive.

As used herein, the term "T1/T2 hybrid" refers to any detection method that combines a T1 and a T2 measurement. For example, the value of a T1/T2 hybrid can be a composite signal obtained through the combination of, ratio, or difference between two or more different T1 and T2 measurements. The T1/T2 hybrid can be obtained, for example, by using a pulse sequence in which T1 and T2 are alternatively measured or acquired in an interleaved fashion. Additionally, the T1/T2 hybrid signal can be acquired with a pulse sequence that measures a relaxation rate that is comprised of both T1 and T2 relaxation rates or mechanisms.

As used herein, the term "T2 signature" refers to a curve established by applying a mathematical transform (e.g., a Laplace transform or inverse Laplace transform) to a decay curve associated with a relaxation rate parameter at a discrete time point or over a set time duration during a rheological event. T2 signature curves provide information about the relative abundance of multiple water populations in a clot. As clotting or fibrinolysis progresses, the T2 signature curves will reflect the changes within the clot. T2 signatures may be used advantageously to assess, in real time, a discriminated hemostatic condition of a subject. Further, a T2 signature may be a two dimensional (intensity versus T2 value or T2 value versus time) or three dimensional representation (intensity versus T2 value versus time). The T2 values in the two- or three dimensional representation may be replaced with or compared to other NMR signals such as T1, T1/T2 hybrid, $T_{1rho}$, $T_{2rho}$ and $T_2^*$.

Other features and advantages of the invention will be apparent from the following Detailed Description, the drawings, and the claims.

BRIEF DESCRIPTION OF THE DRAWINGS

FIG. 1A is a graph illustrating a tri-exponential curve fitting (using equation 2) of a CK sample. FIG. 1B shows a graph illustrating a bi-exponential curve fitting (using equation 1) of a CK sample after truncation of the initial fast phase. FIG. 1C is a graphical depiction of the algorithm used to identify blood clotting behaviors from measurements of NMR relaxation rates.

As shown in FIG. 8A, distinct patient samples spanning a wide range of HCT reference values demonstrates this generally. Applying calibration methods to a single patient sample diluted across a range of HCT, a depicted in FIG. 8B shows the linear dependence on HCT.

FIG. 11A is 50% citrated whole blood with no added fibrinogen; FIG. 11B is 50% citrated whole blood with 1.25 mg/mL added fibrinogen; and FIG. 11C shows a correlation plot for the fibrinogen titration conducted on the patient sample.

FIG. 20 depicts 3D plots for patient samples 29328 and 29350. The TEG MA values measured for samples 29328 and 29350 were 68.4 and 61.9, respectively.

FIGS. 27A-27C show that the T2MR surface is sensitive to whole blood fibrinolysis. To assess this, healthy donor samples were spiked with tissue plasminogen activator (TPA). High sensitivity and rapid time to result for fibrinolysis was demonstrated. See Example 19.

DETAILED DESCRIPTION

Figure 1A:
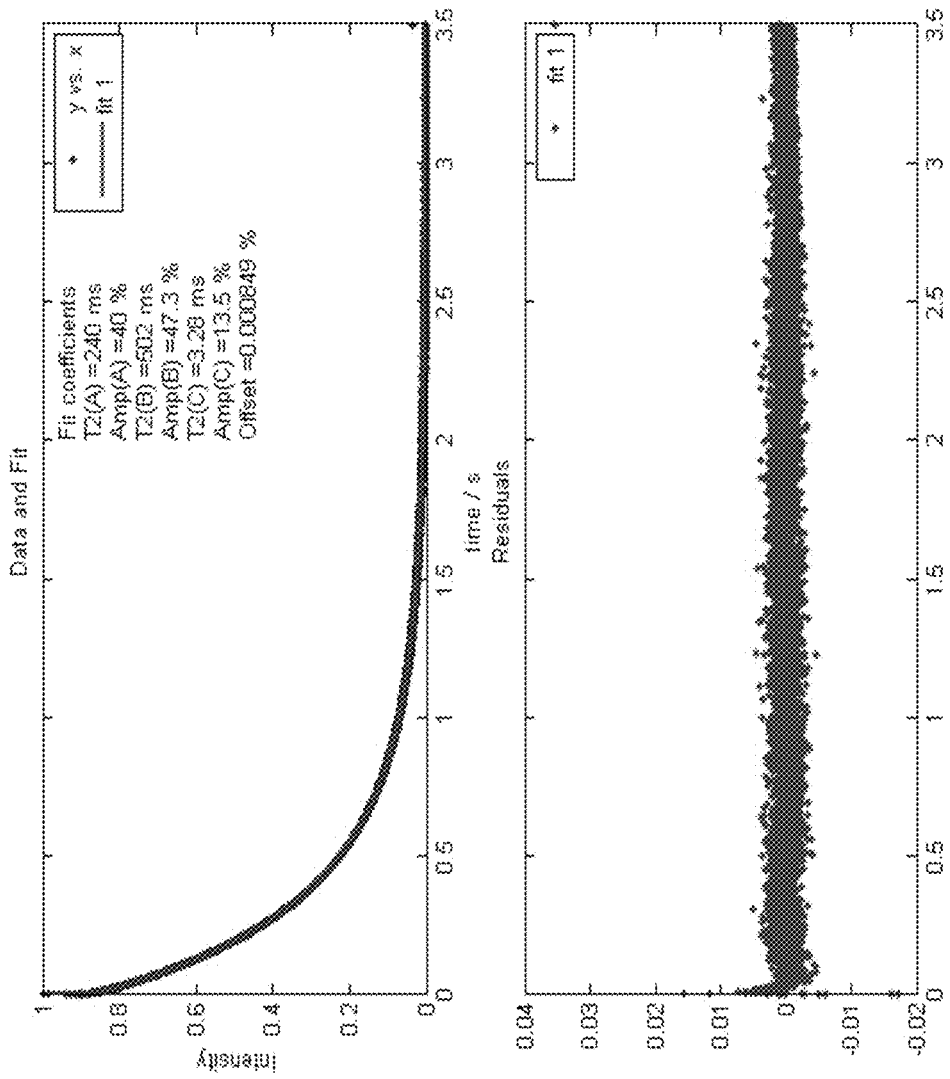
FIGS. 1A-1C depict graphs and equations for identifying NMR relaxation rates for multiple water populations within a sample from a single FID and a method for extracting features from the relaxation rates that are characteristic of the coagulation state of a sample.
Figure 1B:
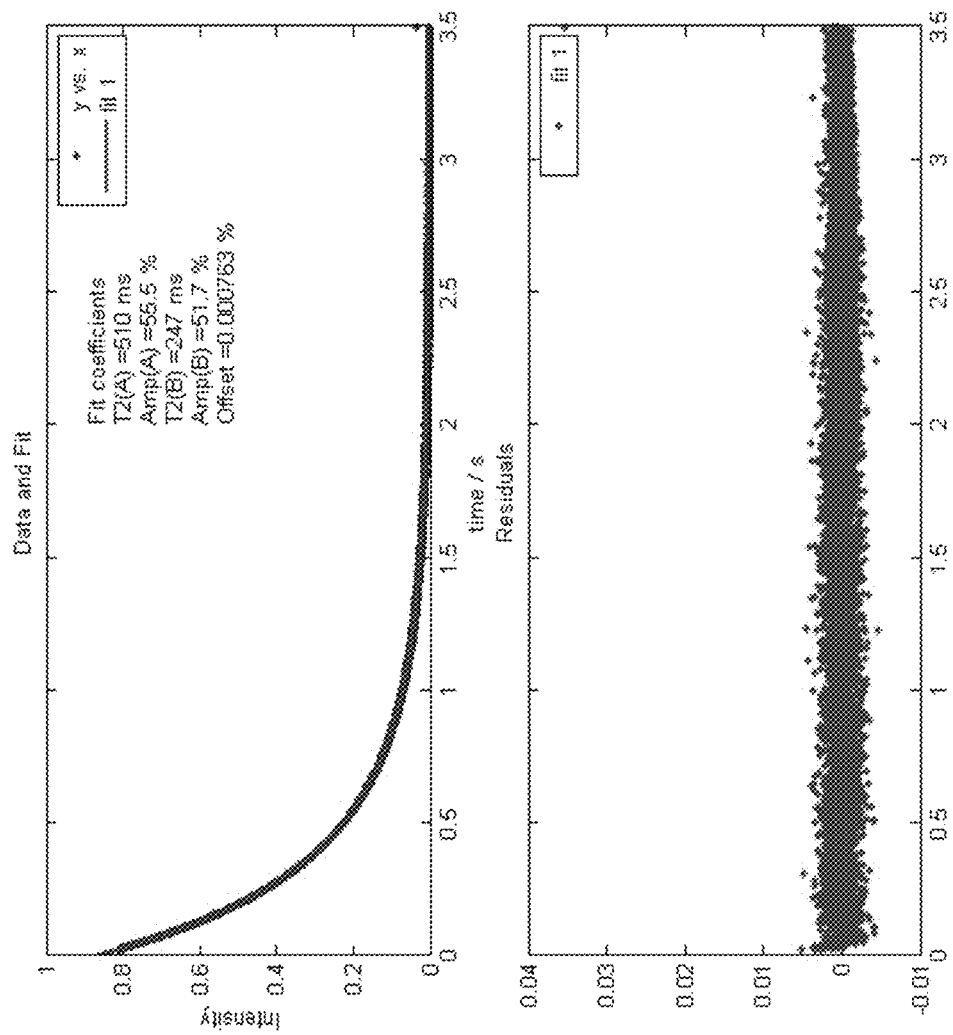

The methods and devices of the invention can be used to assess the risk and occurrence of thrombotic events, including myocardial ischemic events in a patient having or suspected of having vascular disease, particularly in patients who have undergone percutaneous intervention and may be at acute risk of, for example, stent thrombosis, vessel restenosis, myocardial infarction, or stroke. For example, the methods and devices of the invention can be used to assess platelet reactivity (i.e., relative concentration of platelet-associated water molecules in a clot), clotting kinetics, clot strength, clot stability, and time-to-fibrin generation (i.e., R), as indices for risk of a thrombotic event, such as myocardial ischemia, independent of responsiveness to drug therapy (e.g., as assessed by a change in platelet reactivity following administration of an anti-platelet drug such as clopidogrel). These indices can also be used to prevent complications arising from surgical and percutaneous vascular procedures (e.g., stent placement or balloon angioplasty) such as stent thrombosis or re-stenosis. Furthermore, the methods and devices of the invention can be used to identify a safe and effective therapy (e.g., dose, regimen, anti-platelet therapy, among others) for a patient at risk of a thrombotic event or undergoing a surgical procedure.

The methods and devices of the invention can be used to monitor complex samples having water in more than one location or compartment (i.e., samples having more than one water population). For, example, a heterogeneous sample, namely whole blood, there are various populations of water, e.g. plasma water, compartmentalized water, i.e. cellular (erythrocyte, leukocyte, and thrombocyte) water, and water associated with functional features of whole blood processes such as coagulation, e.g. serum, clots, or clot dissolution. Similarly, in a sample undergoing a rheological transition, there is generally more than one population of water; e.g.

water associated with a gel state, water not associated with a gel state, and, in some instances, water associated with a specialized compartment of the sample (i.e. cellular water). The methods of the invention permit one to monitor changes in a sample by simultaneously observing changes in the various water populations present in a sample. The changes can include the formation of new water populations or changes in the relative signal of existing water populations, both of which can be characteristic of the underlying physical properties of the sample before, during, or after a change in rheology (e.g., an ordering or disordering of structure in the sample).

Clotting Initiation

For performing the methods of the invention, clotting may be initiated using a variety of techniques. Citrated kaolin (CK) is a common global initiator for aPTT (activated partial thromboplastin time) and whole blood clotting times. To start the clotting process, calcium chloride and kaolin is mixed with a citrated blood sample. CK-activated samples are characterized by clot formations where platelets and fibrin contribute to the clot. Alternatively, an activator RF may be used to initiate clotting with or without the addition to a platelet activator such as TRAP, AA, or ADP. A-activated samples are characterized by clot formations where fibrin rather than platelets contribute primarily to the clot. Alternatively ADP may be used to activate the clot. ADP-activated samples are characterized by clot formations where fibrin contributes primarily to the clot and platelets contribute to lesser degree. The signal response observed under different activation conditions can be diagnostic of the hemostatic condition of a subject.

Other blood clotting activators that can be used in the methods of the invention include collagen, epinephrine, ristocetin, thrombin, calcium, tissue factor, thromboplastin, kaolin, serotonin, platelet activating factor (PAF), thromboxane A2 (TXA2), fibrinogen, von Willebrand factor (VFW), elastin, fibrinonectin, laminin, vitronectin, thrombospondin, and lanthanide ions (e.g., lanthanum, europium, ytterbium, etc.). Combinations of activators can be used, for example, to aid in identifying an underlying hemostatic condition that results in a subject's blood sample being hypocoagulable.

Signal Acquisition and Processing

Standard radiofrequency pulse sequences for the determination of nuclear resonance parameters are known in the art, for example, the Carr-Purcell-Meiboom-Gill (CPMG) is traditionally used if relaxation constant $T_2$ is to be determined Optimization of the radiofrequency pulse sequences, including selection of the frequency of the radiofrequency pulses in the sequence, pulse powers and pulse lengths, depends on the system under investigation and is performed using procedures known in the art.

Nuclear magnetic resonance parameters that can be obtained using the methods of the present invention include but are not limited to T1, T2, T1/T2 hybrid, $T_{1rho}$, $T_{2rho}$ and $T_2^*$. Typically, at least one of the one or more nuclear resonance parameters that are obtained using the methods of the present invention is spin-spin relaxation constant T2.

As with other diagnostics and analytical instrumentation, the goal of NMR-based diagnostics is to extract information from a sample and deliver a high-confidence result to the user. As the information flows from the sample to the user it typically undergoes several transformations to tailor the information to the specific user. The methods and devices of the invention can be used to obtain diagnostic information about the hemostatic condition of a subject. This is achieved by processing the NMR relaxation signal into one or more series of component signals representative of the different populations of water molecules present, e.g., in a blood sample that is clotting or clotted. For example, NMR relaxation data, such as T2, can be fit to a decaying exponential curve defined by the following equation:

$$f(t) = \sum_{i=1}^{n} A_i \exp(-t/T(i)), \quad (3)$$

where $f(t)$ is the signal intensity as a function of time, t, $A_i$ is the amplitude coefficient for the ith component, and $(T)_i$ the decay constant (such as T2) for the ith component. For relaxation phenomenon discussed here the detected signal is the sum of a discrete number of components (i=1, 2, 3, 4 . . . n). Such functions are called mono-, bi-, tri-, tetra- or multi-exponential, respectively. Due to the widespread need for analyzing multi-exponential processes in science and engineering, there are several established mathematical methods for rapidly obtaining estimates of $A_i$ and $(T)_i$ for each coefficient. Methods that have been successfully applied and may be applied in the processing of the raw data obtained using the methods of the invention include Laplace transforms, algebraic methods, graphical analysis, nonlinear least squares (of which there are many flavors), differentiation methods, the method of modulating functions, integration method, method of moments, rational function approximation, Padé-Laplace transform, and the maximum entropy method (see Istratov, A. A. & Vyvenko, O. F. Rev. Sci. Inst. 70:1233 (1999)). Other methods, which have been specifically demonstrated for low field NMR include singular value decomposition (Lupu, M. & Todor, D. Chemometrics and Intelligent Laboratory Systems 29:11 (1995)) and factor analysis.

There are several software programs and algorithms available that use one or more of these exponential fitting methods. One of the most widely cited sources for exponential fitting programs are those written and provided by Stephen Provencher, called "DISCRETE" and "CONTIN" (Provencher, S. W. & Vogel, R. H. Math. Biosci. 50:251 (1980); Provencher, S. W. Comp. Phys. Comm 27:213 (1982)). Discrete is an algorithm for solving for up to nine discrete components in a multi-component exponential curve. CONTIN is an algorithm that uses an inverse Laplace transform to solve for samples that have a distribution of relaxation times. Commercial applications using multiexponential analyses use these or similar algorithms. In fact, Bruker minispec uses the publicly-available CONTIN algorithm for some of their analysis. For the invention described here, the relaxation times are expected to be discrete values unique to each sample and not a continuous distribution, therefore programs like CONTIN are not needed although they could be used. The code for many other exponential fitting methods are generally available (Istratov, A. A. & Vyvenko, O. F. Rev. Sci. Inst. 70:1233 (1999)) and can be used to obtain medical diagnostic information according to the methods of the present invention. Information is available regarding how the signal to noise ratio and total sampling time relates to the maximum number of terms that can be determined, the maximum resolution that can be achieved, and the range of decay constants that can be fitted. For a signal to noise ratio of ~$10^4$ the theoretical limit as to the resolution of two decay constants measured, independent of the analytical method, is a resolution $\delta=(T_i/T_{i+1})$ of >1.2 (Istratov, A. A. & Vyvenko, O. F. Rev. Sci. Inst. 70:1233 (1999)). Thus it is believed that the difference between resolvable decay constants scales with their magnitudes, which is not entirely intuitive and is unlike resolution by means of optical detection. The understanding of the maximum resolution and the dependence on resolution on the signal-to-noise ratio will assist in assessing the performance of the fitting algorithm.

The methods of the invention can be compared to systems and devices known in the art, such TEG®, ROTEM®, or SONOCLOT®, or other device to measure a rheological change. Further the methods of the invention can be used on a benchtop NMR relaxometer, benchtop time domain system, or NMR analyzer (e.g., ACT, Bruker, CEM Corporation, Exstrom Laboratories, Quantum Magnetics, GE Security division, Halliburton, HTS-111 Magnetic Solutions, MR Resources, NanoMR, NMR Petrophysics, Oxford Instruments, Process NMR Associates, Qualion NMR Analyzers, SPINLOCK Magnetic Resonance Solutions, or Stelar, Resonance Systems).

The CPMG pulse sequence used to collect data with a T2reader is designed to detect the inherent T2 relaxation time of the sample. Typically, this is dictated by one value, but for samples containing a complex mixture of states (e.g., a sample undergoing a clotting process or dissolution process), a distribution of T2 values can be observed. In this situation, the signal obtained with a CPMG sequence is a sum of exponentials. One solution for extracting relaxation information from a T2reader output is to fit a sum of exponentials in a least-squares fashion. Practically, this requires a priori information on how many functions to fit. A second solution is to use the Inverse Laplace transform (ILT) to solve for a distribution of T2 values that make up the exponential signal observed. Again, the results of the CPMG sequence S(t), is assumed to be the sum of exponentials:

$$S(t) = \sum_i A_i e^{-t/T2_i}, \quad (4)$$

where $A_i$ is the amplitude corresponding to the relaxation time constant $T2_i$. If, instead of a discrete sum of exponentials, the signal is assumed to be a distribution of T2 values, the sum over states can be represented b:

$$S(t) = \int_0^\infty A(1/T2) e^{-t/T2} d(1/T2) \quad (5)$$

This has the same functional form as the ILT:

$$F(t) = \int_0^\infty A(s) e^{-st} ds \quad (6),$$

and can be treated as such. The ILT of an exponential function requires constraints to solve. A few methods that can be used to impose constraints are CONTIN, finite mixture modeling (FMM), and neural networks (NN). An inverse Laplace transform may also be used in the generation of a 3D data set. A 3D data set can be generated by collecting a time series of T2 decay curves and applying an inverse Laplace transform to each decay curve to form a 3D data set. Alternatively, a 2D inverse Laplace transform can be applied to a pre-assembled 3D data set to generate a transformed 3D data set describing the distribution of T2 times.

In a heterogeneous environment containing two phases, several different exchange regimes may be operative. In such an environment having two water populations (a and b), $r_a$ and $r_b$ correspond to the relaxation rates of water in the two populations; $f_a$ and $f_b$ correspond to the fraction of nuclei in each phase; $\tau_a$ and $\tau_b$ correspond to residence time in each phase; and $a=(1/\tau_a)+(1/\tau_b)$ corresponds to the chemical exchange rate. The exchange regimes can be designated as: (1) slow exchange: if the two populations are static or exchanging slowly relative to the relaxation rates $r_a$ and $r_b$, the signal contains two separate components, decaying with time constants $T_{2a}$, and $T_{2b}$; (2) fast exchange: if the rate for water molecules exchanging between the two environments is rapid compared to $r_a$ and $r_b$, the total population follows a single exponential decay with an average relaxation rate ($r_{av}$) given by the weighted sum of the relaxation rates of the separate populations; and (3) intermediate exchange: in the general case where there are two relaxation rates $r_1$ and $r_2$ with $r_1$ equal to $r_a$ in the slow exchange limit $r_a<r_b$, $Amp_1+Amp_2=1$, and where $r_{1,2}$ goes to the average relaxation rate in the fast exchange limit, equations 7, 8, 9, and 10 may be applied:

$$r_1 = (1/2)(r_a + r_b + a) - (1/2)\sqrt{(r_b - r_a + a)^2 - 4af_b(r_b - r_a)} \quad (7)$$

$$r_2 = (1/2)(r_a + r_b + a) + (1/2)\sqrt{(r_b - r_a + a)^2 - 4af_b(r_b - r_a)} \quad (8)$$

$$Amp_1 = \frac{r_2 - r_{av}}{r_2 - r_1} \quad (9)$$

$$Amp_2 = \frac{r_{av} - r_1}{r_2 - r_1} \quad (10)$$

The invention also features the use of a pulsed field gradient or a fixed field gradient in the collection of relaxation rate data. The invention further features the use of the techniques of diffusion-weighted imaging (DWI) as described in Vidmar et al. (Vidmar et al., *NMR Biomed.* 23: 34-40 (2010)), which is herein incorporated by reference, or any methods used in porous media NMR (see, e.g., Bergman et al., *Phys. Rev. E* 51: 3393-3400 (1995), which is herein incorporated by reference).

Alternatively, when the methods of the invention are carried out using the measurement of the T2*, or free induction decay, rather than T2, the relaxation properties of a specific class of, for example, water protons in the sample can be made using an off resonance radiation (i.e., radiation that is not precisely at the Larmour precession frequency). The output can be in the form of the height of a single echo obtained with a T2 measuring pulse sequence rather than a complete echo train. In contrast, normal T2 measurements utilize the declining height of a number of echoes to determine T2. The T2* approach can include the steps of shifting the frequency or strength of the applied magnetic field, and measuring the broadness of the water proton absorption peak, where broader peaks or energy absorption are correlated with higher values of T2.

Paramagnetic Agents

The methods of the invention can be carried out in the presence of a paramagnetic agent (e.g., manganese, manganese complexes, gadolinium, gadolinium complexes, or superparamagnetic particles) added, e.g., to the blood prior to initiating clotting. The paramagnetic agent can be free manganese, a manganese complex (e.g., the EDTA complex of manganese), free gadolinium, a gadolinium complex (e.g., the DTPA or DOTA complex of gadolinium), or a superparamagnetic particle. The paramagnetic agent can be used to distinguish clotted from unclotted samples at an earlier time point following the initiation of clotting (see FIG. 46).

The superparamagnetic particles that can be used in the methods of the invention include those described, e.g., in U.S. Pat. No. 7,564,245 and U.S. Patent Application Publication No. 2003-0092029, each of which is incorporated herein by reference. The superparamagnetic particles are generally in the form of conjugates, that is, a superparamagnetic particle coated with moieties that minimize specific and non-specific binding of the particles with constituents of the whole blood sample being measured. The particles have high relaxivity owing to the superparamagnetism of their iron, metal oxide, or other ferro or ferrimagnetic nanomaterials. Iron, cobalt, and nickel compounds and their alloys, rare earth elements such as gadolinium, and certain intermetallics such as gold and vanadium are ferromagnets can be used to produce superparamagnetic particles. The superparamagnetic particles can be monodisperse (a single crystal of a magnetic material, e.g., metal oxide, such as superparamagnetic iron oxide, per superparamagnetic particle) or polydisperse (e.g., a plurality of crystals per magnetic particle). The magnetic metal oxide can also comprise cobalt, magnesium, zinc, or mixtures of these metals with iron. The superparamagnetic particles typically include metal oxide crystals of about 1-25 nm, e.g., about 3-10 nm, or about 5 nm in diameter per crystal. The superparamagnetic particles can also include a polymer component in the form of a core and/or coating, e.g., about 5 to 20 nm thick or more. The overall size of the superparamagnetic particles can be, e.g., from 20 to 50 nm, from 50 to 200 nm, from 100 to 300 nm, from 250 to 500 nm, from 400 to 600 nm, from 500 to 750 nm, from 700 to 1,200 nm, from 1,000 to 1,500 nm, or from 1,500 to 2,000 nm. Superparamagnetic particle size can be controlled by adjusting reaction conditions, for example, by using low temperature during the neutralization of iron salts with a base as described in U.S. Pat. No. 5,262,176. Uniform particle size materials can also be made by fractionating the particles using centrifugation, ultrafiltration, or gel filtration, as described, for example in U.S. Pat. No. 5,492,814. Superparamagnetic particles can also be synthesized according to the method of Molday (Molday, R. S. and D. MacKenzie, "Immunospecific ferromagnetic iron-dextran reagents for the labeling and magnetic separation of cells," J. Immunol. Methods, 52:353 (1982)), and treated with periodate to form aldehyde groups. The aldehyde-containing superparamagnetic particles can then be reacted with a diamine (e.g., ethylene diamine or hexanediamine), which will form a Schiff base, followed by reduction with sodium borohydride or sodium cyanoborohydride. The superparamagnetic particles can be formed from a ferrofluid (i.e., a stable colloidal suspension of superparamagnetic particles). For example, the superparamagnetic particle can be a composite of multiple metal oxide crystals of the order of a few tens of nanometers in size and dispersed in a fluid containing a surfactant, which adsorbs onto the particles and stabilizes them, or by precipitation, in a basic medium, of a solution of metal ions. Suitable ferrofluids are sold by the company Liquids Research Ltd. under the references: WHKS1S9 (A, B or C), which is a water-based ferrofluid comprising magnetite ($Fe_3O_4$), having particles 10 nm in diameter; WHJS1 (A, B or C), which is an isoparaffin-based ferrofluid comprising particles of magnetite ($Fe_3O_4$) 10 nm in diameter; and BKS25 dextran, which is a water-based ferrofluid stabilized with dextran, comprising particles of magnetite ($Fe_3O_4$) 9 nm in diameter. Other suitable ferrofluids for use in the systems and methods of the invention are oleic acid-stabilized ferrofluids available from Ademtech, which include ca. 70% weight $\alpha$-$Fe_2O_3$ particles (ca. 10 nm in diameter), 15% weight octane, and 15% weight oleic acid. The superparamagnetic particles are typically a composite including multiple metal oxide crystals and an organic matrix, and having a surface decorated with functional groups (i.e., amine groups or carboxy groups) for linking binding moieties to the surface of the superparamagnetic particle. For example, the superparamagnetic particles useful in the methods of the invention include those commercially available from Dynal, Seradyn, Kisker, Miltenyi Biotec, Chemicell, Anvil, Biopal, Estapor, Genovis, Thermo Fisher Scientific, JSR micro, Invitrogen, and Ademtech, as well as those described in U.S. Pat. Nos. 4,101,435; 4,452,773; 5,204,457; 5,262,176; 5,424,419; 6,165,378; 6,866,838; 7,001,589; and 7,217,457, each of which is incorporated herein by reference.

For certain assays requiring high sensitivity, analyte detection using T2 relaxation assays can require selecting a proper particle to enable sufficiently sensitive magnetic field-induced agglomeration. Higher sensitivities can be achieved using particles that contain multiple superparamagnetic iron oxide cores (5-15 nm diameter) within a single larger polymer matrix or ferrofluid assembly (100 nm-1200 nm total diameter, such as particles having an average diameter of 100 nm, 200 nm, 250 nm, 300 nm, 500 nm, 800 nm, or 1000 nm), or by using a higher magnetic moment materials or particles with higher density, and/or particles with higher iron content. Without being limited by theory, it is postulated these types of particles provided a sensitivity gain of over 100× due to a much higher number of iron atoms per particle, which is believed to lead to an increase in sensitivity due to the decreased number of particles present in the assay solution and possibly a higher amount of superparamagnetic iron affected by each field-induced agglomeration.

For certain assays it may be desirable to minimize field assisted agglomeration of the superparamagnetic particles by using particles that are less than 40 nm is diameter in the assay.

Database of Signature Curves

In one embodiment, the invention features data processing tools to transform the raw relaxation NMR data into a format that provides signature curves characteristic of hemostatic conditions. Preferred transforms include the Laplace or inverse Laplace transform (ILT). The data for each T2 measurement may be transformed from the time dimension where signal intensity is plotted verses time to a "T2 relaxation" dimension. The ILT provides not only information about the different relaxation rates present in the sample and their relative magnitudes but also reports on the breadth of distribution of those signals.

Each acquired T2 relaxation curve has a corresponding two dimensional signature that maps all of the different populations of water, or different T2 relaxation environments, that water is experiencing in the sample. These curves can be compiled to form a 3D data set by stacking the plots over the duration of the clotting time dimension. This can be used to generate a 3D surface that shows how the different populations of water change as a function of time.

The T2 signatures may become clinically relevant in cases whereby underlying pathology is not discriminated by current techniques. For example, patients that have abnormal PT or aPTT values are often worked up with additional studies that includes PT, aPTT, or PT and aPTT analysis using a 1:1 mixture of a patient blood with normal plasma (to rule out a factor deficiency), and the results may point to a specific factor or von Willebrand factor deficiency. However, frequently patients having a clotting factor deficiency have more than one deficiency or have an unbalance or unchecked clotting cascade. In these patients, a single test for one factor deficiency will not reveal the full dysfunction and the clinician must rely on clinical symptomology (excessive bleeding or clotting) and, unfortunately, time may lead to a deleterious outcome. The ability to detect T2 signatures (for patients having normal or abnormal hemostatic conditions) will allow for rapid understanding of complex pathophysiological coagulation cascade conditions and improve clinical outcomes.

The data gathered using the methods of the invention can be represented using 3D plots generated from different NMR parameters. Additional dimensions can be added by looking at specific patient types or clotting curve types. Data reduction methods can be used to simplify the complex information that is available. Such techniques as principal component analyses (PCA), automated feature extraction methods, or other data handling methods can be used. Ideally, a library of signatures, 2D, and 3D plots can be generated for a wide variety of clinical conditions. For example, two dimensional (intensity versus T2 value or T2 value versus time) or three dimensional representations (intensity versus T2 value versus time). The T2 values in the two- or three dimensional representation may be replaced with or compared to other NMR signals such as T1, T1/T2 hybrid, $T_{1rho}$, $T_{2rho}$ and $T_2^*$.

In related embodiments, a clotting or dissolution process within a sample is assessed by an NMR parameter extracted from one or more free induction decay (FID) signals obtained from the sample. For example, an NMR parameter can be extracted from the signal to noise ratio of an FID, from a comparison of an FID to a predetermined threshold, from the integration of an FID, or from a ratio calculation using different points of the FID. The NMR parameters obtained by the method can be used to characterize a variety of clotting or dissolution processes. In a specific example, values extracted from one or more FIDs of a blood sample may be used to calculate blood clotting behaviors such as clotting time (R), fibrinolytic behavior, clot strength (MA), kinetic behavior of the clot, platelet-associated clot strength ($MA_{PLATELET}$), functional fibrinogen-associated clot strength ($MA_{FF}$), or percent lysis 30 minutes after MA (LY30). Likewise, data extracted from FID data can be used to assemble a library of signature curves.

3D Data Plots 3D representations of the T2 data in a sample undergoing a clotting process or a dissolution process may be generated using the methods of the invention (e.g., the method described in Example 18). In certain embodiments, the dimensions of the generated 3D plots correspond to a relaxation time (e.g., T2 or 1/T2) dimension, an intensity or amplitude dimension, and a time dimension. The time dimension represents the time over which the clotting process has proceeded or is proceeding. The 3D plots obtained from a clotting blood sample exhibit a variety of 3D surface features that correspond with separate water populations in different physical and/or chemical environments within the sample. The 3D plots and the data used to generate the 3D plots may be mined for indices or clotting behaviors associated with the blood sample (e.g., the hematocrit, clot strength (MA), clotting time (R), platelet activity, fibrinogen activity, fibrinolysis, etc.). The 3D plots or the data used to generate the 3D data plots may also be used to discover new indices.

The information contained within the different 3D surface features and water populations evident in the 3D plot may be associated with particular indices and clotting behaviors. The 3D plots can be used to generate qualitative, semiqualitative, and/or qualitative results for a specific parameter or index. For example, the hematocrit of a blood sample may be calculated from properties of the initial water population, the clotting time and fibrinolysis behaviors may be calculated from properties of the diverging water population having a T2 time of 80-400 milliseconds, and the platelet activity and clot strength may be calculated from properties of the second diverging water population, which has a T2 time of 400-2200 milliseconds. A variety of methods can be used to extract the indices or clotting behaviors from the 3D data set. For example, the slope or curvature of a 3D surface feature of a 3D plot may be correlated with a clotting behavior. A cross-section of a 3D plot may also be used to calculate a clotting behavior. In particular, a cross-section showing T2 intensity as a function of time for a particular T2 time may be useful in calculating the clotting time (R) and/or fibrinolysis. A cross-section of a 3D plot showing T2 time as a function of intensity at a given time (a T2 relaxation spectrum) depicts the various water populations present in a sample at a given time. The features of a T2 relaxation spectrum can be mined for a range of clotting behaviors. For example, the difference between two signals in a T2 relaxation spectrum may be used to evaluate clot strength. The integration of a particular 3D surface feature, such as the volume of a particular feature, or curve from a cross-section of a 3D plot may also be useful in establishing a clotting behavior (e.g. clot strength). Clotting behaviors may also be extracted through the integration of a range of T2 relaxation spectra collected at sequential or disparate time points.

Alternatively, the 3D plots can be used to identify a feature characteristic of clot behavior. The feature can be one that is measured without 3D analysis, such as via pulse sequence for selectively monitoring a water population having an average T2 relaxation rate of about 400 milliseconds or 1,000 milliseconds at a particular time post clot initiation. Optionally, the water population is measured exclusive of other water populations in the sample.

The features of a T2 relaxation curve, including the range of T2 values associated with a particular signal, may vary based on the instrument (e.g., a T2reader or a Bruker minispec) used to collect data. Likewise, the range of T2 values for a given sample may depend on the material used to construct the tubes (e.g., plastic or glass) containing the sample during T2 measurements. The invention encompasses the use of any magnetic resonance instrument and any sample container in the collection of a 3D data set used in the analysis of a blood sample.

Management of Patients

The methods and the devices of the invention can be used to provide a point-of-care evaluation of the hemostatic condition of a patient (e.g., for coagulation management of patients undergoing surgery, to identify patients at risk of thrombotic complications, to identify a patient resistant to antiplatelet therapy, to monitor anticoagulation therapy in a patient, to monitor antiplatelet therapy in a patient, and/or to monitor procoagulant therapy in a patient).

There are medical circumstances for which a coagulation test is requested including: 1) finding a cause for abnormal bleeding or bruising, 2) in patients with an autoimmune disease, 3) in patients with an underlying cardiovascular disorder, 4) before procedures or surgeries where too much bleeding may be a concern, 5) monitoring anti-coagulant therapy, 6) monitoring peri-operative and trauma patients, and 7) identifying patients with sepsis or septic shock.

Coagulation management of patients undergoing cardiac surgery is complex because of a balance between anticoagulation for cardiopulmonary bypass (CPB) and hemostasis after CPB. Furthermore, an increasing number of patients have impaired platelet function at baseline due to administration of antiplatelet drugs. During CPB, optimal anticoagulation dictates that coagulation is antagonized and platelets are prevented from activation so that clots do not form. After surgery, coagulation abnormalities, platelet dysfunction, and fibrinolysis can occur, creating a situation whereby hemostatic integrity must be restored. The complex process of anticoagulation with heparin, antagonism with protamine, and postoperative hemostasis therapy can be guided by the method and devices of the invention (a point of care test) that assess hemostatic function in a timely and accurate manner.

Problems associated with poor liver function (e.g., decreased synthesis and clearance of clotting factors and platelet defects) can lead to impaired hemostasis and hyperfibrinolysis. Systemic complications, such as sepsis and disseminated intravascular coagulation, further complicate a preexisting coagulopathy. Marked changes in hemostasis in orthotopic liver transplantation occur during the anhepatic phase and immediately after organ reperfusion, mainly a hyperfibrinolysis resulting from accumulation of tissue plasminogen activator due to inadequate hepatic clearance and a release of exogenous heparin and endogenous heparin-like substances. Thus, patients undergoing hepatic surgery, and particularly orthotopic liver transplantation, may have large derangement in their coagulation, making the method and devices of the invention useful for monitoring this patient population.

The method and devices of the invention can be used to guide heparin therapy, among other anticoagulation therapies. For example, the methods of the invention can be carried out with heparinase to assess the coagulation status in the absence of the anticoagulatory effects of heparin. Further, the methods of the invention can be utilized to assess protamine therapy, i.e. to monitor coagulation after protamine therapy and to treat a heparin or protamine induced hemostatic condition. Similarly, analysis could be done pre- and post surgery to determine the anticoagulant or hemostatic status of a surgical patient.

The method and devices of the invention can also be used to guide antiplatelet therapies and identify resistance to antiplatelet therapies. Antiplatelet therapy is increasingly being prescribed for primary and secondary prevention of cardiovascular disease to decrease the incidence of acute cerebro- and cardiovascular events. Antiplatelet drugs typically target to inhibit cyclooxygenase 1/thromboxaneA2 receptors (e.g., aspirin), adenosine diphosphate receptors (e.g., clopidogrel), or GPIIb/IIIa receptors (e.g., abciximab, tirofiban). Although antiplatelet drugs are thought to work primarily by decreasing platelet aggregation, they also have been shown to function as anticoagulants. Because platelets play a key role in overall coagulation, the assessment of the platelet function (more than their number) is critical in the perioperative setting.

The method and devices of the invention can also be used to monitor and/or guide anticoagulant therapies. Anticoagulant therapies (e.g., rivaroxaban, dabigatran, among others) can be monitored for efficacy and compliance, and to ensure avoidance of adverse side effects and/or adverse events (e.g., bleeding events). Dosing adjustments for such therapies have been reported to control bleeding in large, randomized studies. Specifically, dosing of anticoagulants, including direct Factor Xa inhibitors can be used to assist maintenance of a therapeutic window and lead to a reduction of risk of stroke in atrial fibrillation and deep vein thrombosis in patients.

The method and devices of the invention can be used to identify patients resistant to anticoagulant therapy. Anticoagulant therapies include aspirin, plavix, and prasugrel, among other anticoagulants. The method includes (i) administering the anticoagulation therapy to the subject; (ii) evaluating the hemostatic condition of the subject using a method of the invention; and (iii) if the subject is found to be prothrombotic, identifying the subject as a non-responder to the anticoagulation therapy. The identification of non-responders can permit a physician to identify a safe and efficacious anticoagulant to which the patient is responsive, thereby reducing the risk of adverse events (i.e., thrombi formation and stroke).

The method and devices of the invention can be used to monitor procoagulant therapy. The modern practice of coagulation management is based on the concept of specific component therapy and requires rapid diagnosis and monitoring of the pro-coagulant therapy. It has been shown, for example, that platelet transfusion in the perioperative period of coronary artery bypass graft surgery is associated with increased risk for serious adverse events. Clinical judgment alone may not predict who will benefit from a platelet transfusion in the acute perioperative setting. Accordingly, the transfusion of coagulation products should be preferably guided by a point of care test, such as the test provided by the method and devices of the invention.

The method and the devices of the invention can be used to provide a companion diagnostic analysis or test to monitor the effects of a therapeutic compound in a clinical trial or in medical use. The diagnostic analysis may include determining whether or not the subject of the trial or the patient responds to therapy or does not respond to therapy.

The method and the devices of the invention can be used to determine the perfusion through clots, hypercoagulation, hyperclotting, or clotting that is deleterious in a human, as in stroke or cardiac arrest.

The method and the devices of the invention can be used as part of a panel of analyses. The panel can include (i) an immunoassay to proteins that are involved in the coagulation cascade; (ii) an immunoassay to detect fibrin degradation products; (iii) an immune assay to detect antiphospholipid antibodies; (iv) an assay to detect heparin or warfarin or other anticoagulant to assess therapeutic concentration; (v) a PT or aPTT or PTT assay that monitors the plasma prothrombin time; (vi) a genetic test to assess the polymorphic differences in genes encoding proteins that are relevant to (a) the formation or dissolution of thrombin, (b) the coagulation cascade, (c) heparin binding, or (d) therapeutic activity.

The methods and the devices of the invention can be used to manage medical devices with implications towards coagulopathies. An example is a ventricle assist device often used as a bridge for patients awaiting a heart transplant. Patients with such an implant may have clot formation within and outside of the device as a result of the function of the device, and these clots may cause a stroke or another thrombus related event. It may also lead towards infections and bleeding events. A way to avoid these issues is to monitor multiple diagnostic markers that impact the success of the device. For instance, routine testing of PT-INR would allow tighter monitoring of the patients coagulation state, thus, providing tight control of bleeding and clotting events.

The INR is the ratio of a patient's prothrombin time to a normal (control) sample, raised to the power of the International Sensitivity Index value for the analytical system used. A high INR level (e.g., INR=5) indicates that there is a high chance of bleeding, whereas if the INR=0.5 then there is a high chance of having a clot. Normal INR range for a healthy person is 0.9-1.3. For people on warfarin therapy the INR range is typically 2.0-3.0. The target INR may be higher in particular situations, such as for those with a mechanical heart valve, or bridging warfarin with a low-molecular weight heparin (such as enoxaparin (Lovenox)) perioperatively.

Monitoring platelet function, fibrinolysis, clot strength and other factors are equally important in improving outcomes. Understanding the physiologic concentration or activities of these factors are important not just for their interplay with the device, but because they are modulated by the many different therapies often prescribed to patients on these devices (aspirin, rivaroxaban, plavix, warfarin, among others). Another measure that is used with these types of devices is hematocrit, which is often used to adjust the functioning of the device (speed, intensity, etc.) to maintain the function of the heart. The methods and the devices of the invention can provide all of these results (hematocrit, platelet, PT, PT-INR, etc.), potentially simultaneously, and it may provide additional information with respect to clot formation and dissolution. The standard measures above may be combined into an index or signature that identifies the status of the patient and efficacy of the device.

The methods and the devices of the invention can be utilized and configured in multiple ways. They can be used as a laboratory device, point-of-care system, or even an implantable monitoring system. For example, as an implantable monitoring system, the sample can consist of continually monitored blood; a vacutainer with whole blood, serum, or plasma; or a finger stick, among other sample fluids.

For example, the methods and the devices of the invention can be utilized for monitoring peri-operative and trauma patients (e.g., providing measures or surrogate measures for PT/INR, aPTT, ACT, Hct, platelet activity, and fibrinolysis). There is a need with these patient populations to quickly and efficiently determine if a transfusion is needed as the patients can exhibit an approximately 6-fold increase in mortality, ischemic events, infection, early onset of complications, and increased ICU/hospital stays. Specifically, determination of the root cause of bleeding events (coagulation cascade vs. platelet activation) can lead to prompt and focused therapy.

Regardless of the context in which the methods and the devices of the invention are utilized, that the methods of the invention can be used to rapidly measure small volumes is particularly important for platelet function, which previously were difficult to measure using other systems due to the initiation of clotting at the site of the blood draw.

The Clotting Mechanism

For clotting to occur there must be activation of coagulation cascade culminating in fibrin deposition through the action of thrombin on fibrinogen. The coagulation system is composed of a proteolytic cascade that amplifies an initial stimulus with an elegant feedback regulation mechanism to keep the overall process in check and balance. There are two interconnected routes of clotting activation: (i) contact activation (intrinsic pathway); and (ii) tissue factor activation (extrinsic pathway). Both pathways rely on a variety of coagulation factors. Prothrombin is coagulation factor II, thrombin is coagulation factor IIa, fibrinogen is coagulation factor I, and fibrin is coagulation factor Ia. In addition to the coagulation factors, platelets are critical both for the induction and formation of an adequate blood clot. Platelets act as a phospholipid surface upon which prothrombinase complexes are formed and act as a physical scaffold for the developing clot.

The intrinsic coagulation cascade pathway is normally activated by contact with collagen from damaged blood vessels, but many negatively charged surfaces can stimulate this pathway. The intrinsic pathway normally requires platelet activation in order to assemble a tenase complex involving factors VIIIa, IXa, and X. The activation process is linked to the inositol triphosphate (IP3) pathway and involves degranulation and myosin 1c kinase activation in order to change the platelet shape to ultimately allow adherence.

Clotting may alternatively be activated via the extrinsic coagulation cascade pathway which requires a tissue factor from the surface of extravascular cells. The extrinsic pathway involves complex formation of coagulation factors V, VII, and X. The chief inducer of coagulation in vivo is Tissue Factor (TF), a 47 kDa glycoprotein. The only cells capable of expressing TF in the bloodstream are endothelial cells and monocytes. By contrast, many cells outside the bloodstream, including adventitial fibroblasts, constitutively express TF and thus form an "extravascular envelope" capable of initiating coagulation in the event of a disruption in vascular integrity.

The final stages of the cascade are common to both pathways which involves a tenase complex, the activating complex. Tenase is a contraction of "ten" and the suffix "-ase", signifying that the complex activates its substrate (inactive factor X) by cleaving it. Intrinsic tenase complex contains the active factor IX (IXa), its cofactor factor VIII (VIIIa), the substrate (factor X), and they are activated by negatively charged surfaces (such as glass, active platelet membrane, sometimes cell membrane of monocytes). Extrinsic tenase complex is made up of tissue factor, factor VII, the substrate (factor X) and $Ca^{2+}$ as an activating ion.

Activation of factor X, to factor Xa, through either the extrinsic or the intrinsic pathway, leads to the proteolytic conversion of prothrombin to thrombin which, in turn, activates the initiation of the formation of a clot. Factor VIII then catalyzes a transglutaminase reaction to crosslink the fibrin monomers to form a crosslinked network.

The crosslinked fibrin multimers in a clot are broken down to soluble polypeptides by plasmin, a serine protease. Plasmin can be generated from its inactive precursor plasminogen and recruited to the site of a fibrin clot in two ways, by interaction with tissue plasminogen activator at the surface of a fibrin clot, and by interaction with urokinase plasminogen activator at a cell surface. The first mechanism appears to be the major one responsible for the dissolution of clots within blood vessels. The second, although capable of mediating clot dissolution, may normally play a major role in tissue remodeling, cell migration, and inflammation.

Clot dissolution is regulated in two ways. First, efficient plasmin activation and fibrinolysis occur only in complexes formed at the clot surface or on a cell membrane; proteins free in the blood are inefficient catalysts and are rapidly inactivated. Second, both plasminogen activators and plasmin itself are inactivated by specific serpins, proteins that bind to serine proteases to form stable, enzymatically inactive complexes. Pharmacologically, the clot buster tissue plasminogen activator (TPA) and streptokinase or urokinase are used to activate this internal fibrinolytic mechanism.

Medical Conditions

The methods and the device of the invention as herein described may be used for the detection of rheological changes of various liquids, in particular blood samples, for the diagnosis of coagulation, thrombotic disorders, and thrombotic disorders as a result of disease, e.g., sepsis and disseminated intravascular coagulation (DIC), Hemophilia A, Hemophilia B, Hemophilia C, Congenital deficiency of other clotting factors Factor XIII deficiency, Von Willebrand's disease, hemorrhagic disorder due to intrinsic anticoagulants, defibrination syndrome, acquired coagulation factor deficiency, coagulation defects, other, purpura and other hemorrhagic conditions, allergic purpura, Henoch-Schönlein purpura, thrombocytopenia, immune thrombocytopenic purpura, idiopathic thrombocytopenic purpura, secondary thrombocytopenia, and non-specific hemorrhagic conditions.

The cardiovascular system requires tightly regulated hemostasis. Excessive clotting may cause venous or arterial obstructions, while failure to clot may cause excessive bleeding; both conditions lead to deleterious clinical situations. In most human subjects, the clotting balance is more or less static. However, there are many different clinical parameters (such as hereditary disorders, disease states, therapeutic drugs, or pharmacological stressors) that can alter hemostasis and lead to cardiovascular malfunction.

There are many different known coagulation disorders that are a result of non-functional clotting factors, such as hemophilia (factors VIII (hemophilia A), IX (hemophilia B), XI (hemophilia C)), Alexander disease (factor VII deficiency), prothrombin deficiency (factor II deficiency), Owren's disease (factor V deficiency), Stuart-Prower deficiency (factor X deficiency), Hageman factor deficiency (factor XII deficiency), fibrinogen deficiency (factor I deficiency), and von Willebrand's diseases.

The activation of the coagulation cascades appears to be an essential component in the development of multi-organ failure that occurs in end-stage sepsis. Current therapies for sepsis specifically target these cascades for modulation of the progression of the end stages and to prevent organ failure.

The methods and devices of the invention may be used to determine the hematocrit of a blood sample. The hematocrit is a measure of the percent volume occupied by red blood cells in a subject's blood, with normal values for healthy women and men being approximately 36-44% and 41-50%, respectively. The hematocrit depends on both the number of red blood cells in a sample and the size of the red blood cells. The measurement of hematocrit may be useful in establishing a variety of physiological conditions in a subject. Thus, the methods of the invention may be used in the diagnosis of any condition associated with a lower than normal hematocrit or a higher than normal hematocrit. A lower than normal hematocrit may be indicative of anemia, sickle cell anemia, internal bleeding, loss of red blood cells, malnutrition, nutritional deficiencies (e.g., iron, vitamin B12, or folate deficiencies), or over hydration. A higher than normal hematocrit may be indicative of congenital heart disease, dehydration, erythrocytosis, pulmonary fibrosis, polycythemia rubra vera, or abuse of the drug erythropoietin.

The methods of the invention can be used to monitor factors and related coagulopathies associated with disease, disorder or dysfunction such as cancer, autoimmune disorders, lupus erythematosus, Crohn's disease, multiple sclerosis, amyotrophic lateral sclerosis, deep vein or arterial thrombosis, obesity, rheumatoid arthritis, Alzheimer's disease, diabetes, cardiovascular disease, congestive heart failure, myocardial infarction, coronary artery disease, endocarditis, stroke, emboli, pneumonia, ulcerative colitis, inflammatory bowel disease, chronic obstructive pulmonary disease, asthma, infections, transplant recipients, liver disease, hepatitis, pancreas disease and disorders, renal disease and disorders, endocrine disease and disorders, obesity, diseases or disorders associated with thrombocytopenia, and medical (stents, implants, major surgery, joint replacements, pregnancy) or therapeutic (cancer chemotherapy) induced coagulopathy/ies, and risk factors such as heavy smoking, heavy alcohol consumption, sedentary lifestyle. The methods of the invention may also be used to evaluate genomic and proteomic changes that affect coagulation and blood properties.

The methods of the invention can also be used to monitor patients being undergoing anti-coagulant and/or anti-platelet therapy. Examples of anti-thrombotics (e.g., thrombolytics, anticoagulants, and antiplatelet drugs) that can be monitored using the methods of the invention include, without limitation, vitamin K antagonists such as acenocoumarol, clorindione, dicumarol, diphenadione, ethyl biscoumacetate, phenprocoumon, phenindione, tioclomarol, and warfarin; heparin group (platelet aggregation inhibitors) such as antithrombin III, bemiparin, dalteparin, danaparoid, enoxaparin, heparin, nadroparin, parnaparin, reviparin, sulodexide, and tinzaparin; other platelet aggregation inhibitors such as abciximab, acetylsalicylic acid (aspirin), aloxiprin, beraprost, ditazole, carbasalate calcium, cloricromen, clopidogrel, dipyridamole, epoprostenol, eptifibatide, indobufen, iloprost, picotamide, prasugrel, ticlopidine, tirofiban, treprostinil, and triflusal; enzymes such as alteplase, ancrod, anistreplase, brinase, drotrecogin alfa, fibrinolysin, procein C, reteplase, saruplase, streptokinase, tenecteplase, and urokinase; direct thrombin inhibitors such as argatroban, bivalirudin, desirudin, lepirudin, melagatran, and ximelagatran; other antithrombotics such as dabigatran, defibrotide, dermatan sulfate, fondaparinux, and rivaroxaban; and others such as citrate, EDTA, and oxalate.

Sepsis and Disseminated Intravascular Coagulation

The methods and devices of the invention can be used to assess the hemostatic condition of subjects suffering from sepsis or disseminated intravascular coagulation.

In sepsis, an overwhelming inflammatory response causes extensive collateral damage to the host's microcirculation. Damage to the endothelium exposes tissue factor and in sepsis, which may occur on a large scale. Tissue factor, in turn, binds to activated factor VII. The resulting complex activates factors IX and X. Factor X converts prothrombin into thrombin, which cleaves fibrinogen into fibrin, inducing the formation of a blood clot. At the same time, the fibrinolytic system is inhibited. Cytokines and thrombin stimulate the release of plasminogen-activator inhibitor-1 (PAI-1) from platelets and the endothelium. When a clot forms in the human body, it is ultimately broken down by plasmin, which is activated by tissue plasminogen activator (TPA). PAI-1 inhibits TPA. Consequently, subjects suffering from severe sepsis are treated with an anticoagulant such as protein C (blood coagulant factor XIV).

Disseminated intravascular coagulation (DIC) is a complex systemic thrombohemorrhagic disorder involving the generation of intravascular fibrin and the consumption of procoagulants and platelets. The resultant clinical condition is characterized by intravascular coagulation and hemorrhage. DIC is not an illness on its own but rather a complication or an effect of progression of other illnesses and is estimated to be present in up to 1% of hospitalized patients. DIC is always secondary to an underlying disorder and is associated with a number of clinical conditions, generally involving activation of systemic inflammation. DIC has several consistent components including activation of intravascular coagulation, depletion of clotting factors, and end-organ damage. DIC is most commonly observed in severe sepsis and septic shock. Indeed, the development and severity of DIC correlates with mortality in severe sepsis. Although bacteremia, including both gram-positive and gram-negative organisms, is most commonly associated with DIC, other infections including viral, fungal, and parasitic infections may cause DIC. Trauma, especially neurotrauma, is also frequently associated with DIC. DIC is more frequently observed in those patients with trauma who develop the systemic inflammatory response syndrome. Evidence indicates that inflammatory cytokines play a central role in DIC in both trauma patients and septic patients. In fact, systemic cytokine profiles in both septic patients and trauma patients are nearly identical.

DIC exists in both acute and chronic forms. DIC develops acutely when sudden exposure of blood to procoagulants occurs, including tissue factor (tissue thromboplastin), generating intravascular coagulation. Compensatory hemostatic mechanisms are quickly overwhelmed, and, as a consequence, a severe consumptive coagulopathy leading to hemorrhage develops. Abnormalities of blood coagulation parameters are readily identified, and organ failure frequently occurs in acute DIC. In contrast, chronic DIC reflects a compensated state that develops when blood is continuously or intermittently exposed to small amounts of tissue factor. In chronic DIC, compensatory mechanisms in the liver and bone marrow are not overwhelmed, and there may be little obvious clinical or laboratory indication of the presence of DIC. Chronic DIC is more frequently observed in solid tumors and in large aortic aneurysms.

Exposure to tissue factor in the circulation occurs via endothelial disruption, tissue damage, or inflammatory or tumor cell expression of procoagulant molecules, including tissue factor. Tissue factor activates coagulation by the extrinsic pathway involving factor VIIa. Factor VIIa has been implicated as the central mediator of intravascular coagulation in sepsis. Blocking the factor VIIa pathway in sepsis has been shown to prevent the development of DIC, whereas interrupting alternative pathways did not demonstrate any effect on clotting. The tissue factor-VIIa complex then serves to activate thrombin, which, in turn, cleaves fibrinogen to fibrin while simultaneously causing platelet aggregation. Evidence suggests that the intrinsic (or contact) pathway is also activated in DIC, while contributing more to hemodynamic instability and hypotension than to activation of clotting.

Decreased levels of antithrombin correlate with elevated mortality in patients with sepsis. Thrombin generation is usually tightly regulated by multiple hemostatic mechanisms. Antithrombin function is one such mechanism responsible for regulating thrombin levels. However, due to multiple factors, antithrombin activity is reduced in patients with sepsis. First, antithrombin is continuously consumed by ongoing activation of coagulation. Moreover, elastase produced by activated neutrophils degrades antithrombin as well as other proteins. Further antithrombin is lost to capillary leakage. Lastly, production of antithrombin is impaired secondary to liver damage resulting from underperfusion and microvascular coagulation.

Tissue factor pathway inhibitor (TFPI) depletion is evidence in subjects with DIC. TFPI inhibits the tissue factor-VIIa complex. Although levels of TFPI are normal in patients with sepsis, a relative insufficiency in DIC is evident. TFPI depletion in animal models predisposes them to DIC, and TFPI blocks the procoagulant effect of endotoxin in humans. The intravascular fibrin produced by thrombin is normally eliminated via a process termed fibrinolysis. The initial response to inflammation appears to be augmentation of fibrinolytic action; however, this response soon reverses as inhibitors of fibrinolysis are released. High levels of PAI-1 precede DIC and predict poor clinical outcomes. Fibrinolysis cannot keep pace with increased fibrin formation, eventually resulting in under-opposed fibrin deposition in the vasculature.

Protein C, along with protein S, serves in important anticoagulant compensatory mechanisms. Under normal conditions, protein C is activated by thrombin and is complexed on the endothelial cell surface with thrombomodulin. Activated protein C combats coagulation via proteolytic cleavage of factors Va and VIIIa. However, cytokines (e.g., tumor necrosis factor $\alpha$ (TNF-$\alpha$) and interleukin 1 (IL-1)) produced in sepsis and other generalized inflammatory states largely incapacitate the protein C pathway. Inflammatory cytokines down-regulate the expression of thrombomodulin on the endothelial cell surface. Protein C levels are further reduced via consumption, extravascular leakage, reduced hepatic production, and by a reduction in freely circulating protein S.

Inflammatory and coagulation pathways interact in substantial ways. Many of the activated coagulation factors produced in DIC contribute to the propagation of inflammation by stimulating endothelial cell release of proinflammatory cytokines. Factor Xa, thrombin, and the tissue factor-VIIa complex have each been demonstrated to elicit proinflammatory action. Furthermore, given the anti-inflammatory action of activated protein C, its impairment in DIC contributes to further dysregulation of inflammation.

Components of DIC include: exposure of blood to procoagulant substances; fibrin deposition in the microvasculature; impaired fibrinolysis; depletion of coagulation factors and platelets (consumptive coagulopathy); organ damage and failure. DIC may occur in 30-50% of patients with sepsis.

The methods and devices of the invention may find use in monitoring subjects with a variety of DIC-associated conditions such as: sepsis/severe infection; trauma (neurotrauma); organ destruction; malignancy (solid and myeloproliferative malignancies); severe transfusion reactions; rheumatologic illness; obstetric complications (amniotic fluid embolism, abruptio placentae, hemolysis, retained dead fetus syndrome); vacular abnormalities (Kasabach-Merritt syndrome, aneurysms); hepatic failure; toxic reactions, transfusion reactions, and transplant rejections. Similarly, the invention may be used with respect to subjects having hemostatic conditions characterized by acute DIC associated with bacterial infections (e.g., gram-negative sepsis, gram-positive infections, or rickettsial), viral infections (e.g., associated with HIV, cytomegalovirus, varicella, or hepatitis), fungal infections, parasitic infection (e.g., malaria), malignancy (e.g., acute myelocytic leukemias), obstetric conditions (e.g., eclampsia placental abruption or amniotic fluid embolism), trauma, burns, transfusion, hemolytic reactions, or transplant rejection.

The NMR-based methods of the invention may be use to monitor any and all of the blood-related conditions described above. Time-domain relaxometry, particularly T2 relaxation measurements, can be used to measure a change in the clotting state of a sample. This measurement relies on measuring NMR parameters of the hydrogen nuclei that are sensitive to changes in the macroscopic clotting state of the sample. Most of the hydrogen nuclei are in the bulk water solvent, but an appreciable fraction of them are in the biological macromolecules and cells and platelets in the sample. As such, the measurement of the average NMR signal from all hydrogen nuclei can be conducted such that the signal changes in an appreciable manner when the clotting state of the sample changes for any of the clinical reasons described above. The NMR measurement can be a T2 relaxation measurement, or an "effective" T2 relaxation measurement (e.g., a T2 relaxation measurement where the parameters of the signal acquisition are such that they are set for optimal readout of the clotting event and not for the most accurate measurement of a T2 relaxation value). Other "time domain" relaxation measurement methods can be applied to measure changes in clotting behaviors. These may include time-domain free-induction decay analyses amongst other measurements. Any of the NMR time domain measurements described herein can be acquired in a repeated fashion to get a dynamic read-out of the NMR signal over the course of time as the clotting or dissolution properties of the sample change.

Subjects Having Normal and Abnormal Hemostatic Profiles

The methods of the invention can be used to discriminate between subjects having normal and abnormal hemostatic profiles. For example, the NMR relaxation parameter value and/or T2 signature characteristic of normal and abnormal hemostatic profiles can be determined and used in the differential diagnosis of a subject. Abnormal hemostatic profiles can include profiles for subjects sharing a common deficiency in one or more clotting factors, clotting cofactors, and/or regulatory proteins (e.g., factor XII, factor XI, factor IX, factor VII, factor X, factor II, factor VIII, factor V, factor III (tissue factor), fibrinogen, factor I, factor XIII, von Willebrand factor, protein C, protein S, thrombomodulin, and antithrombin III, among others).

A deficiency in antithrombin is seen in approximately 2% of patients with venous thromboembolic disease. Inheritance occurs as an autosomal dominant trait. The prevalence of symptomatic antithrombin deficiency ranges from 1 per 2000 to 1 per 5000 in the general population. Deficiencies results from mutations that affect synthesis or stability of antithrombin or from mutations that affect the protease and/or heparin binding sites of antithrombin. The methods of the invention can be used to discriminate between normal subjects and subjects having a deficiency in antithrombin.

A deficiency in factor XI confers an injury-related bleeding tendency. This deficiency was identified in 1953 and originally termed hemophilia C. Factor XI deficiency is very common in Ashkenazic Jews and is inherited as an autosomal disorder with either homozygosity or compound heterozygosity. The methods of the invention can be used to discriminate between normal subjects and subjects having a deficiency in factor XI.

von Willebrand disease (vWD) is due to inherited deficiency in von Willebrand factor (vWF). vWD is the most common inherited bleeding disorder of humans. Deficiency of vWF results in defective platelet adhesion and causes a secondary deficiency in factor VIII. The result is that vWF deficiency can cause bleeding that appears similar to that caused by platelet dysfunction or hemophilia. vWD is an extremely heterogeneous disorder that has been classified into several major subtypes. Type I vWD is the most common and is inherited as an autosomal dominant trait. This variant is due to simple quantitative deficiency of all vWF multimers. Type 2 vWD is also subdivided further dependent upon whether the dysfunctional protein has decreased or paradoxically increased function in certain laboratory tests of binding to platelets. Type 3 vWD is clinically severe and is characterized by recessive inheritance and virtual absence of vWF. The methods of the invention can be used to discriminate between normal subjects and subjects having a deficiency in von Willebrand factor.

Several cardiovascular risk factors are associated with abnormalities in fibrinogen. Elevated plasma fibrinogen levels have been observed in patients with coronary artery disease, diabetes, hypertension, peripheral artery disease, hyperlipoproteinemia and hypertriglyceridemia. In addition, pregnancy, menopause, hypercholesterolemia, use of oral contraceptives and smoking lead to increased plasma fibrinogen levels. There are inherited disorders in fibrinogen, including afibrinogenemia (a complete lack of fibrinogen), hypofibrinogenemia (reduced levels of fibrinogen) and dysfibrinogenemia (presence of dysfunctional fibrinogen). Afibrinogenemia is characterized by neonatal umbilical cord hemorrhage, ecchymoses, mucosal hemorrhage, internal hemorrhage, and recurrent abortion. The disorder is inherited in an autosomal recessive manner. Hypofibrinogenemia is characterized by fibrinogen levels below 100 mg/dL (normal is 250-350 mg/dL) and can be either acquired or inherited. The methods of the invention can be used to discriminate between normal subjects and subjects having abnormalities in fibrinogen.

Platelet Monitoring

The methods and device of the invention can be used to determine platelet function and be compared to platelet aggregometry (see, e.g., Harris et al., Thrombosis Research 120:323 (2007)). Currently there are two detection methods used in instruments with FDA clearance for performing platelet aggregometry: optical and impedance measurements. For example, the methods of the invention can be used to identify any platelet activity or diagnose any platelet dysfunction in a subject that may be measured by platelet aggregometry. Platelet aggregometry is a functional test performed on a whole blood or platelet-rich plasma sample. Generally, platelet aggregometry methods involve adding a platelet activator to the sample and measuring the induced platelet aggregation. Platelet aggregometry can be performed by immersing an electrode in the blood sample being tested. Platelets adhering to the probe form a stable monolayer. When an activator is added, platelet aggregates form on the electrode and increase the resistance to a current being applied across the electrode. The instrument monitors the change in electrical impedance, which reflects the platelet aggregation response. Aggregometry methods also include techniques based on monitoring the release of ATP from aggregating platelets by luminescence. Optical detection of platelet aggregation is based on the observation that, as platelets aggregate into large clumps, there is an increase in light transmittance. Different aggregation-inducing agents stimulate different pathways of activation and different patterns of aggregation are observed. The main drawback of the optical method is that it is typically performed on PRP, necessitating the separation of platelets from red blood cells and adjustment of the platelet count to a standardized value.

As in platelet aggregometry, the methods of the invention may be used assess the platelet count from a blood sample of a subject or to diagnose a condition of thrombocytopenia (platelet count <150,000/µL) or thrombocytosis (platelet count >400,000/µL) in a subject. Such a diagnosis may be used as the basis of a decision to provide the subject with a platelet transfusion or an anticoagulant. Similarly, the methods of the invention may be used to evaluate the response of a subject to a platelet transfusion or an anticoagulant.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Other Uses

The NMR-based methods of the invention described herein may be used in a variety of applications where a substance or mixture of substances is undergoing or has undergone a clotting process or a dissolution process. The methods of the invention may be used to obtain information on changes within a material undergoing a process or on the state of a material which has already undergone a process.

In the field of petroleum products, the methods of the invention may be used to monitor asphalt/bitumen, bitumen-polymer manufacture, boiler, crude oil, coal ash, coal slurry, cracking, distillation residues, engineering, fluxed bitumen, high viscosity oil, furnace oils, lubricant, mixing fuel oils, oil additives, oil clarificator, blending oils, oils counters (pipeline terminal), oils wear control, plastisols, mineral oils, petroleum additives manufacture, petroleum products, pipe line counters, pitch coating, pitch dilution, pumping of Erika disaster, quench oil, residues transformation in fuel oils, separation of water, sediment and oils, special oils, synthetic rubber, tar control before use, very heavy oil, and water-coal slurries.

In the field of coatings and paint, the methods of the invention may be used to monitor car paint, metallic paint, water paint, special ink for scraping game, special ink for aluminum or plastic surfaces, water ink, PTFE coating, white paper coating, special paper coating, wall paper, glue, varnish, car varnish, special paint for engines, manufacture of ink, photogravure, dye, print board varnish, magnetic ink, magnetic varnish, gloss paint, silvering for mirrors, special varnish for spectacles, and enamel powder.

In the field of food and beverages, the methods of the invention may be used to monitor bechamel sauce manufacture, bread manufacture, chocolate manufacture, dough control, fermentation control, fish solubles (evaporation control), fresh cheese manufacture, gelatin food concentration, ice creams manufacture, jam manufacture, margarine manufacture, mayonnaise manufacture, melted cheese manufacture, milk and cheese research, paraffin coating control, proteins concentration control, proteins for animal food, seaweed gelatin, slop control, stewed fruit, sugar boilers (crystallization control), sugar mixer, surimi paste, synthetic flavors, tomato sauce, vegetable margarine and oil, yeasts, yogurt, beer/yeast Control, dough in a bakery, food additives, gelatins (proteins concentration), milk atomization, yogurt, processed cheese, sweetened juice, salad sauce, food thickener, food additives, enzymes concentration control, freezing fluid control artificial food flavor, tobacco liquor, residual sugar liquor, industrial soups, pudding, milk powder, pet food, livestock food, baby food, evaporated milk, starch gel, fruit paste, and fruit juice.

In the field of industrial chemistry, the methods of the invention may be used to monitor basic resins for paints manufacture, polymer, polymer-bitumen manufacture, polymerization control, polycarbonate, PVC Production, two components resins, fibers and polymers, cable resin, epoxy resin, polyamide resins, chloral methyl resins, PVC, carboxyl methyl cellulose, hydrochloric acid, urethane glue, toluene diisocyanate, MEK toluene, plastic recycling, silicone oils, paste, glue, PBU, ethanol toluol, polycarbonate, polyester resins manufacture, polyether polyol control, polyisobutylene, polymer resins manufacture, polymerised vinyl+toluene, polymerization industry, resins polymerization silicones oils, unsaturated polyester resin, urea-formol resin, glue, polyamide resin, nylon, polypropylene resin, polyethylene, epoxy resin, polyephine wax, dimethyl acetate, phenolic resin, plaster, melamine, and methyl methacrylate.

The methods of the invention may also be used to monitor biochemical products, cellulose acetates, fabric softener, enzymes, gel coatings, pharmaceutical capsules, aerosols, chemicals manufacturing (washing bases), cosmetics manufacture and control, creams, engineering in cosmetics machines, fermentation control, glasses for spectacles, pharmaceuticals, photographic emulsions, shampoo manufacture, tooth paste, UV sensitive varnishes, viscosity control in emulsion, vitamin A, photographic emulsions, videotapes, gels, emulsions, delicate chemistry, fluorescent paste for lighting, hydraulic oils, latex atomization, UV glue, hot melt glue, drilling mud, plastisols, acid concentration, mercury, accumulator acid, detergent, ceramic, slurries, glue, adhesive polymer, calcium carbonate, acrylic glue, lime milk, ammonia+MCB+oil, high viscosity combustible fuels, crude oil counting, mixing of two oils, lubricant oils, animal fat boiler, fuel oil, wastewater concentration, mud concentration, yeast sludge, oil contamination, solvent contamination, distressing control of oil, quench oil, cutting oil, and processes involving a setting tower.

The methods and the devices of the invention can be used as a lead compound and compound validation discovery tool. The methods and devices of the invention can identify variations in the coagulation cascade as a function of intervention in the cascade by one or more candidate compounds, or identify variations outside the coagulation cascade (e.g., platelet morphology) in response to candidate compounds. The methods and devices of the invention can be used to screen compound libraries to identify active agents, as well as pinpoint new mechanisms for disease and treatment. These are likely to be in the coagulation cascade, but many will be targets not usually defined or identified in the cascade. This approach can also be used to identify disease states that are differentiated from known coagulation disorders.

The coagulation system is a highly complex system and available tools for study of this system are limited in the breadth of information that they can provide to scientists engaged in drug discovery. Many current drug discoveries rely on target based screening, while others rely on phenotypic screening. Targeted methods include the use of molecular methods of action, similar to gene expression or RNAi to isolate the target of interest with an assay and then use that assay to search for compounds. Phenotypic screening identifies changes to biology that occur due to a compound or agent, thus characterizing promising leads because they have the desired effect in the body. For cases of inhibition of the target, wild-type constructs of the target can be used. For instances of activation of a target, genetically modified version of the target can be used. This approach addresses one limitation of certain existing screening methods that cannot look the target or the activity of the target in matrices such as whole blood. For targets in hemostasis and coagulation, this can be problematic due to the complex nature of the biological interactions that any given target can undergo in blood. Potential screening targets include proteins, peptides, enzymes, fibrinogen, thrombin, platelets, platelet receptors, diseased state of platelets, clotting factors, diseased state of any of these targets.

The methods and the devices of the invention can generate an information rich data set generated from the clotting of a patient sample blood or plasma due to the addition of a specific initiator. Various initiators can be used to trigger blood clotting at different starting points. These different initiators can be used to isolate or highlight different portions of the clotting cascade by activation at selected points or branches of the cascade and/or inhibition of selected points and/or branches of the cascade. For a given clotting reaction, the methods of the invention enable the generation of a 3D surface data set that captures multiple parameters such as hematocrit levels, clotting time, platelet activity, fibrinolysis, and many other physiological and biological parameters. Thus, specific initiators can be used to explore and isolate specific coagulation pathways.

Another means to select and hone in on a specific part of the coagulation pathway or hemostasis system is to use genetically modified systems, such as knock-out mice or rats. These systems/models allow one to produce a target that represents the diseased state (e.g., a diseased platelet), and applying the methods of the invention to the blood in this system/model in the absence and presence of the candidate compound to evaluate the effectiveness of the compound to ameliorate the disease state. The small sample volume requirement of T2MR may be advantageous to animal studies. Conventional platelet methods require 0.5-25 mL of blood, while the methods of the invention can be carried out using much smaller volumes.

Another advantage of the screening methods of the invention is that numerous features are available to identify anchor points, and sensitivity features for measuring the effects of compounds on the hemostasis process.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLE 1

Monitoring the Blood Clotting Process Using Whole Blood Samples

The clotting process was monitored using fresh citrated or heparinized whole blood samples. Several different activation pathways were examined.

For the kaolin activation pathway (CK pathway), 1 mL of citrated blood was added to a kaolin vial (PlateletMapping assay kit, Haemonetics). The vial was inverted five times to mix the sample. 34 µL of the blood/kaolin mix was transferred into a 200 µL PCR tube pre-heated at 37° C. 2 µL of the 0.2M $CaCl_2$ was added to the PCR tube and the T2 measurement was started immediately.

For the activator pathway (A pathway), 1 µL of freshly prepared activator solution (A-P1, PlateletMapping assay kit, Haemonetics, also referred to herein as "RF") was added to a 200 µL PCR tube pre-heated at 37° C. 36 µL of blood collected in a heparinase vial was added to the PCR tube and the sample was mixed with a pipette tip 3-4 times. The T2 measurement was started immediately.

For the Activator (RF)+ADP pathway, 1 µL of freshly prepared activator solution (A-P1, PlateletMapping assay kit, Haemonetics) and 1 µL of freshly prepared platelet agonist solution (ADP-P2, PlateletMapping assay kit, Haemonetics) were added to a 200 µL PCR tube pre-heated at 37° C. 36 µL of blood collected in heparinase vial was added to the PCR tube and the sample was mixed with a pipette tip 3-4 times. The T2 measurement was started immediately.

Figure 4:
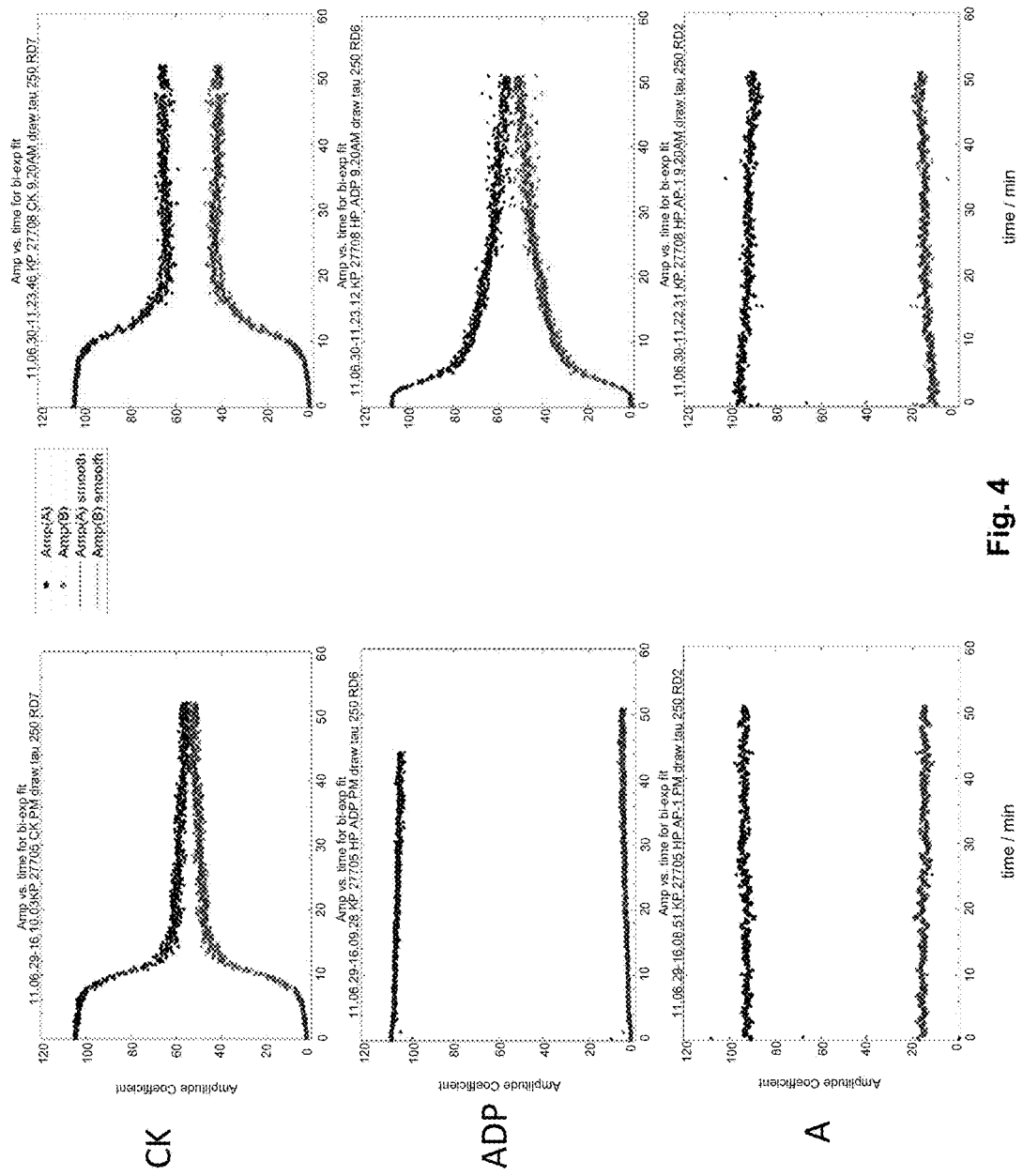
FIG. 4 is a series of plots of AmpA and AmpB for CK (kaolin) versus ADP (adenosine diphosphate)+RF (reptilase and factor XIII) versus A activated samples from two different patients (see Example 1 and Table 1 for a description of the different activation pathways). In both samples, the kaolin activated samples displayed a significant increase in AmpB during clot formation. In both subject samples, the A activated samples did not display a significant increase in the AmpB during clot formation. The activator RF activates fibrin formation. When an ADP+RF activator was used, the sample from one subject exhibited no significant change in AmpB during clot formation, while the sample from the other subject exhibited a significant change in AmpB during clot formation. The variability in the value of an NMR parameter for a water population in a blood sample undergoing a clotting or dissolution process under different conditions (i.e., in the presence of different clotting initiators or clotting inhibitors) can be characteristic of the hypercoagulability or hypocoagulability of the blood sample and/or characteristic of a hemostatic condition in the subject from whom the sample was taken.

FIG. 4 depicts the differences in clotting behavior associated with the three different activation pathways.

EXAMPLE 2

Data Extraction Using an Algorithm for Interpreting Blood Clotting in a Sample

The data output from the T2reader of Example 1 was processed using a three-step method of performing a bi-exponential fit, plotting and checking, and feature extraction:

Bi-Exponential Fit

Figure 1C:
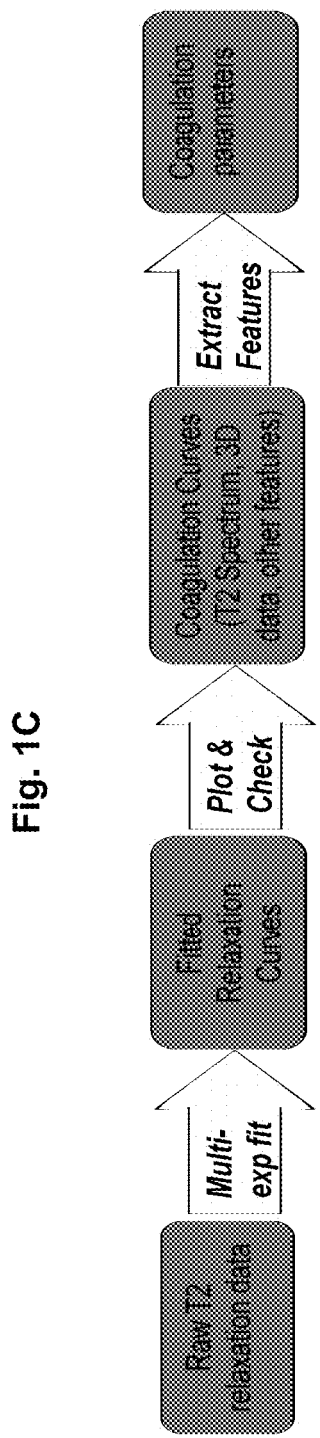
Figure 2:
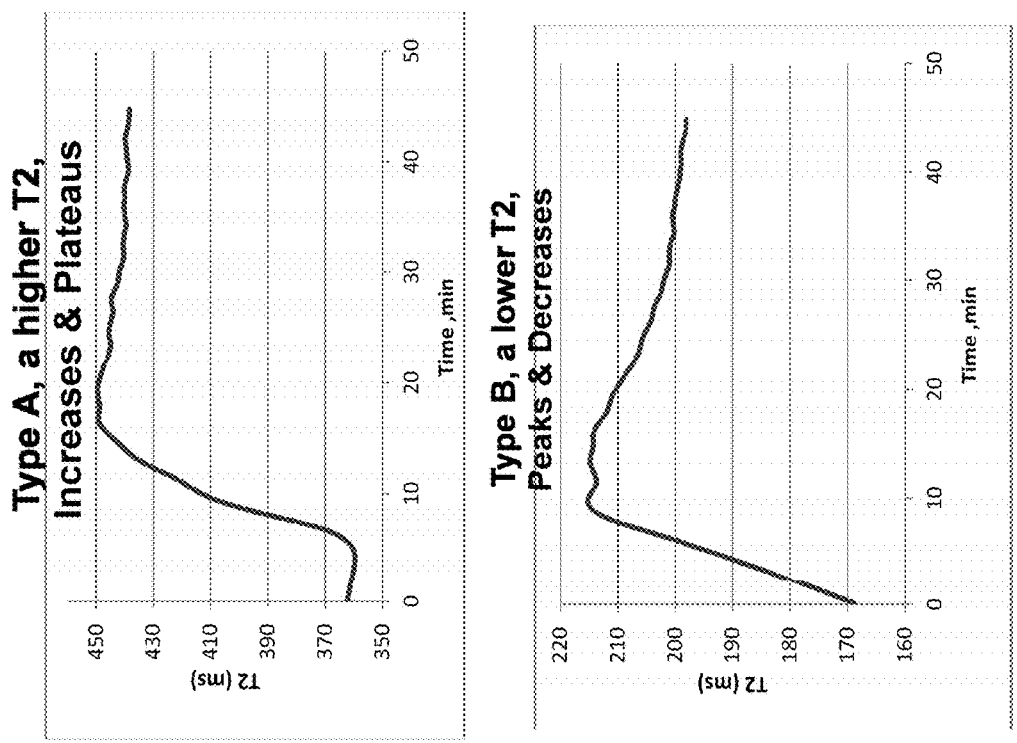
FIG. 2 depicts two plots showing the change in the observed T2 relaxation values (T2A and T2B) for the different populations of water in a single CK blood sample undergoing clotting. The figure illustrates that the relaxation rates of the separate water populations may be monitored as a function of time. The T2 value of water population A decreases initially, then increases, and then plateaus during the clotting process; the T2 values of water population B increases initially in the clotting process, peaks, and then decreases. The change in T2 values for a water population in a blood sample undergoing a clotting or dissolution process can be characteristic of the hypercoagulability or hypocoagulability of the blood sample.
Figure 3:
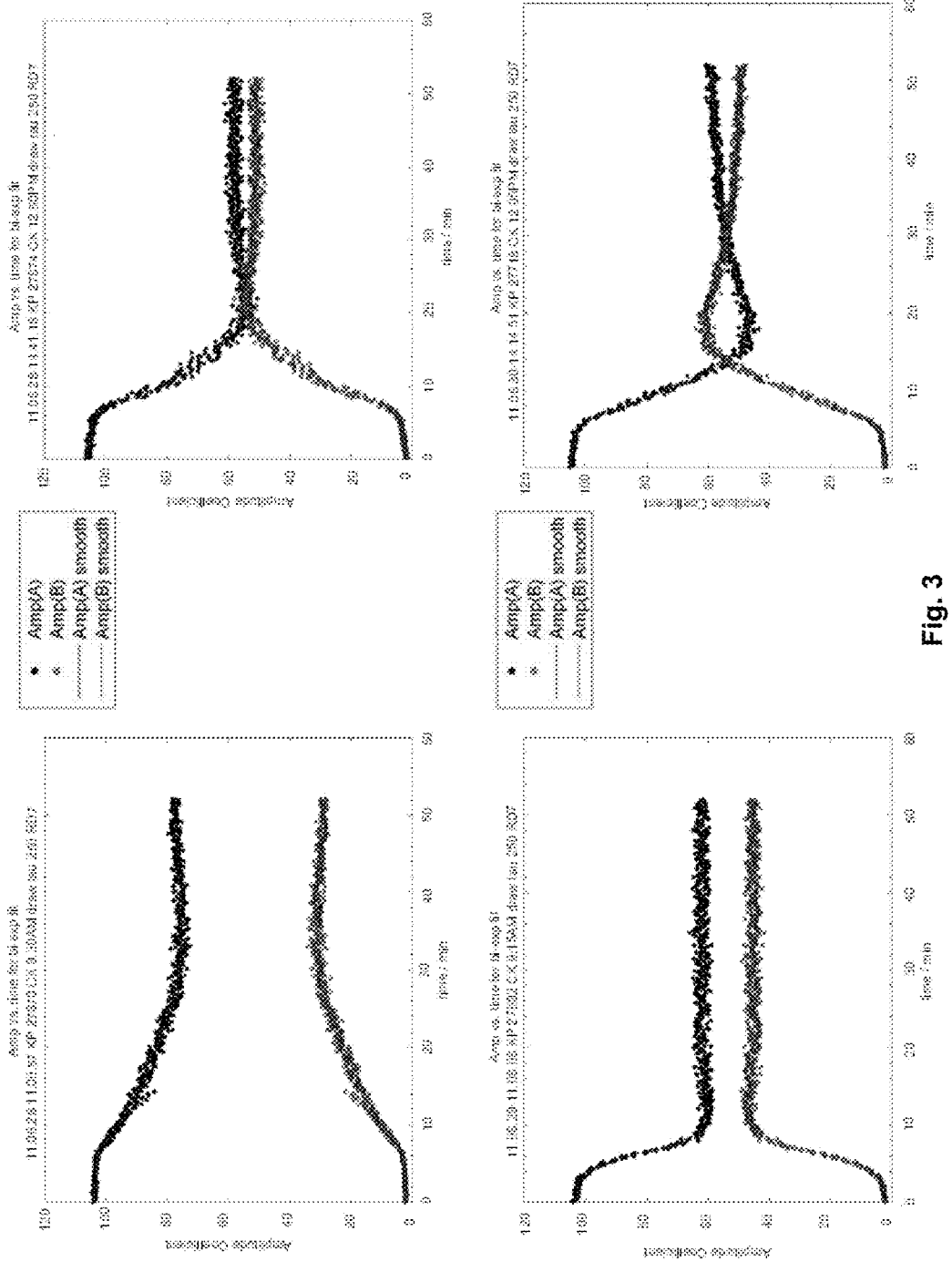
FIG. 3 is a series of plots depicting the change in the amplitude values (AmpA and AmpB) for the different populations of water in CK blood samples undergoing clotting. The blood samples were taken from four different healthy subjects meeting the criteria for making blood donations and not taking anticoagulant medication. The change in amplitude values for a water population in a blood sample undergoing a clotting or dissolution process can be characteristic of the hypercoagulability or hypocoagulability of the blood sample.

The read time was registered by NDXClient. The complex y data was converted to magnitude and normalized. The initial 25 milliseconds of x and y was removed. Each relaxation curve was fit using the default non-linear least square method. The curves were fitted to a bi-exponential equation using start points (e.g., seeds) for AmpA, AmpB, T2A, and T2B with fixed seeds used for the first five time points. The seed for the sixth time point was obtained from the average of the first five time points. Generally, time points were seeded with output from the previous time point. Negative values for parameters were not allowed. Alternatively, the data can be fit initially in the middle of the time series, working similarly to the ends. The goodness-of-fit term was computed by taking the sum of squares of the fit residuals, excluding non-negative values, called SSE (see FIGS. 1A and 1C). The parameters AmpA, AmpB, T2A, and T2B were binned into their respective categories to create a text file.

Plotting and Checking

The fits that did not meet the SSE criteria were flagged and removed. A simple smoothing function based on local regression using weighted LLS and 1 degree polynomials was performed and outlier data was discarded. Each fit parameter was plotted versus time (smoothed and unsmoothed). Data shift and reflections were conducted to mimic TEG tracing and produce a T2Coagulation curve. T2Coagulation curves may be produced by applying a linear transformation to the extracted magnetic resonance parameters. In particular, a T2Coagulation curve could be obtained from T2A data by subtracting the minimum T2A value from each of the data points and taking the negative of each resulting data point, effectively reflecting the curve about the x axis. Likewise, a T2Coagulation curve could be obtained from T2B data by subtracting the maximum T2B value from each of the data points and taking the negative of each resulting data point, effectively reflecting the curve about the x axis. The amplitude data AmpA and AmpB could be transformed into a T2Coagulation curve by similar methods.

Extract Features

The plotted curves were measured to extract the values associated with clotting behaviors "R", "MA", and "angle." Data extraction can be carried out using any of a variety of methods known in the art. For example, metrics can be derived from the curve shape of the resulting data and/or calculated from the value of one or more NMR parameters.

EXAMPLE 3

Use of a Capillary Method for Measuring Clotting Behaviors

A capillary tube was used to collect a 2- to 5-p L blood sample from a patient. The blood sample was collected from a fingerstick using a lance, and the sample was collected into a heparinized capillary tube and capped with clay. Alternatively the blood was collected in a pyrex tube and capped with clay. Alternatively the blood sample was collected in a glass Dagan capillary tube and capped with clay and did not contain an activator. Data for T2 NMR relaxation rate was recorded from the capillary sample using a T2reader. It was determined that the collected data was monoexponential and that this may reflect a different clot structure than is present in standard CK curves. Presumably, the surface of the capillary induces blood clotting.

EXAMPLE 4

Treatment of Blood with Nanoparticles

Doping of blood with superparamagnetic nanoparticles leads to a change in the susceptibility of the bulk water in blood. A similar phenomenon has been previously used by adding manganese to blood to alter the T2 values of bulk water and enable a chemical-shift enabled exchange measurement of water inside and outside of the red blood cells. Blood samples from a single patient were used for experiments based on the protocol set forth in Example 1. Additionally, blood samples were treated with unfunctionalized 800 nm diameter nanoparticles. Two different concentrations of nanoparticles were tested. The two different concentrations were achieved by adding either 10 µL of nanoparticles or 20 µL of nanoparticles. T2 data was recorded using a T2reader. The recorded T2 data was processed using the algorithm described in Example 2. From a series of plots of AmpA and AmpB for samples containing nanoparticles, it was observed that the nanoparticles reduced the noise observed in the curves, permitting AmpA and AmpB to be distinguished more easily. From a series of plots of T2A and T2B for samples containing nanoparticles, it was observed that the nanoparticles produced a larger change in T2A. Superparamagnetic nanoparticles can be useful in the methods of the invention for (i) increasing signal change (or the change in the value of an NMR parameter) in response to rheological changes in a sample, and/or (ii) permitting a earlier detection of changes in rheology in a sample undergoing a clotting or dissolution process.

Figure 26B:
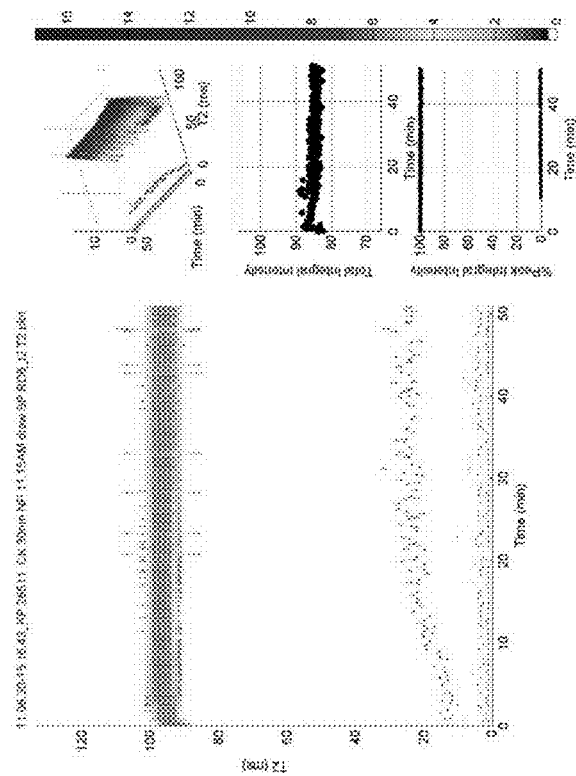
FIGS. 26A-26C depict the changes in the T2 relaxation curve of a blood sample with and without a paramagnetic agent of varying size. Samples were run without magnetic particles (see FIG. 26A), with CLIO nanoparticles (30 nm size; ca. 0.05 ng) (see FIG. 26B), and with Seramag superparamagnetic particles (730 nm size; ca. 0.05 ng) (see FIG. 26C). Addition of 30 nm nanoparticles erases the clot signal (at T2=200 msec) in a typical citrated kaolin experiment, only 1 peak at T2~100 msec is present. Addition of 730 nm superparamagnetic particles does not interfere with the ability to observe both peaks. See Example 4.
Figure 26A:
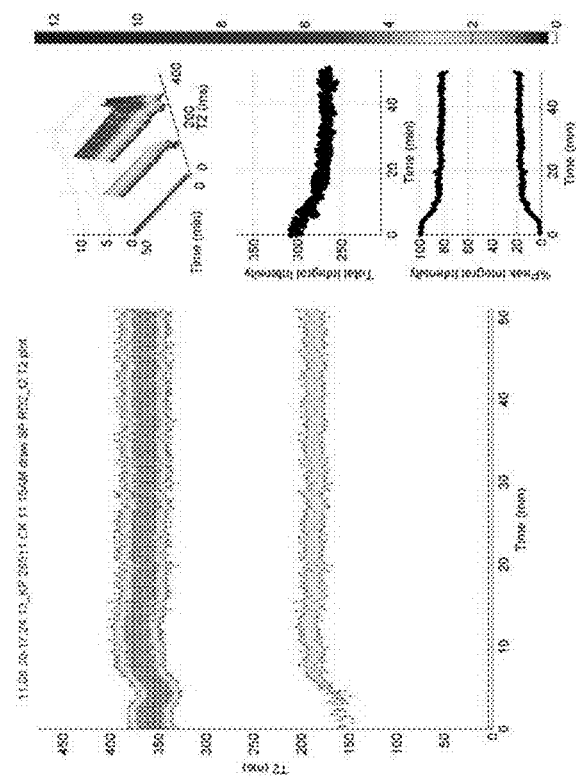
Figure 26C:
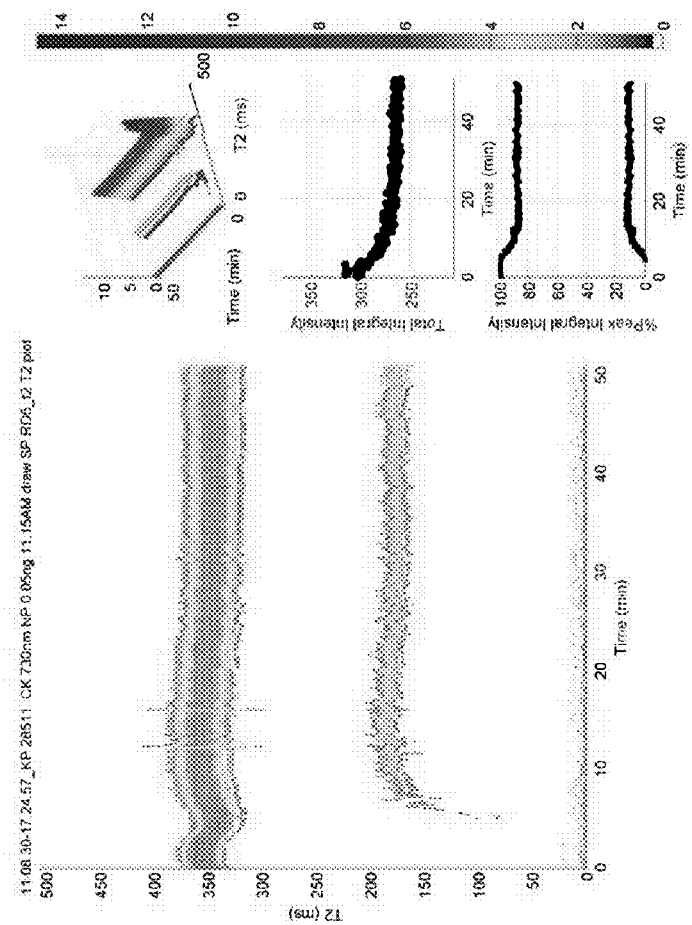

In a separate experiment, the effect of the size of the superparamagnetic particle on T2MR in clotting blood was observed. Blood samples were prepared by combining 1 mL of citrated whole blood with 1 tube of Kaolin reagent from (TEG) with gentle mixing by inversion 5 times. 34 µL of blood/kaolin mixture was placed in a PCR tube (200 µL) and preheated at 37° C. for 1 minute. Clotting was initiated by addition of 2 µL of 0.2M $CaCl_2$, and the tube was placed into a T2 reader. Samples were run without magnetic particles (see FIG. 26A), with CLIO nanoparticles (30 nm size; ca. 0.05 ng) (see FIG. 26B), and with Seramag superparamagnetic particles (730 nm size; ca. 0.05 ng) (see FIG. 26C).

Addition of 30 nm nanoparticles erases the clot signal (at T2=200 msec) in a typical citrated kaolin experiment, only 1 peak at T2~100 msec is present. Addition of 730 nm superparamagnetic particles does not interfere with the ability to observe both peaks.

EXAMPLE 5

Determination of Magnetic Resonance Parameters Value from Donor Blood Samples The magnetic resonance parameters used for data extraction were obtained using blood samples obtained from donors. The blood samples were evaluated using both the TEG method and the T2Coagulation method. Several different types of assays were run. The T2Coagulation data was collected using one of a number of T2readers.

Whole Blood Clotting Assays

Donor blood samples were evaluated using the method of the invention and the TEG method. As described in Example 1, a number of different whole blood clotting assays were used. These assays are further summarized in Table 1.

TABLE 1

Whole blood clotting assays and activators tested

| TEG Assay Type | Blood Anticoagulent | Activator(s) | Comments |
|---|---|---|---|
| Kaolin Activation (K or CK) | citrate | kaolin (clay) which generates thrombin, the most potent platelet activator and clotting activator | part of the TEG platelet mapping assay |
| Activator (RF) | heparin | reptilase and factor XIII | part of the TEG platelet mapping assay; excludes platelet contribution to clotting |
| ADP Agonist (ADP) | heparin | adenosine diphosphate | part of the TEG platelet mapping assay |
| AA Agonist (AA) | heparin | arachidonic acid | part of the TEG platelet mapping assay |
| Functional Fibrinogen Test (FF) | citrate | tissue factor and platelet inhibiting agent | excludes the platelet contribution to clotting |

The K test generates a clot by both platelet activation and the enzymatic cascade that leads to fibrin formation. This clot bypasses any types of platelet inhibitor drugs and provides an assessment of overall whole blood coagulation. It is thought that the TEG R value provides a reflection of the enzymatic pathway and the TEG MA value provides a reflection of the clot strength, which is driven by both platelets and the product of the enzymatic pathway, the fibrin network RF, ADP, and AA tests use heparin to inhibit the thrombin pathway to isolate the pathway activated by each specific agonist. ADP and AA activate platelets, and there is an additional contribution to clot strength by formation of the fibrin network. The RF run doesn't activate platelets but does activate the fibrin network. Therefore, when the MA from an RF run is subtracted from a K, ADP, or AA run, the contribution of platelets to MA of those respective runs can be determined. It is noteworthy that this is an indirect measure of platelet function.

Running K and ADP blood clotting assays on a patient can be used to determine the amount of platelet inhibition a patient is under due to an anti-platelet therapy such as Plavix, Ticlid, and Effient, which are ADP platelet inhibitors. The TEG MA values for K and ADP runs are compared to determine this inhibition.

Running K and AA blood clotting assays can be used to determine the percentage of platelets that are inhibited by an anti-platelet therapy, such as aspirin, ReoPro®, Aggrastat, Integrilin, and non-steroidal anti-inflammatory drugs. These drugs all inhibit the GPIIb/IIIa platelet receptor, which is the receptor activated by the agonists in AA. This is done by comparing the MA values for K and AA. The GPIIb/IIIa receptors are expressed on the platelet surface when platelets are activated (Corporation, H., *TEG® 5000 System Guide to PlateletMapping® Assay* 2010; Enriquez, L. J. and L. Shore-Lesserson, *Point-of-care coagulation testing and transfusion algorithms*. Br J Anaesth, 2009. 103 Suppl 1: p. i14-22; Kroll, M. H., *Thromboelastography: Theory and Practice in Measuring Hemostatis*. Clinical Laboratory News, 2010: p. 8-10).

The FF test excludes the platelet contribution to clotting. Subtraction of the FF MA from the K MA yields clot strength presumably due to platelet contribution. This is an indirect measure of platelet function. Comparing the MA from FF and K tests to reference ranges can indicate if a bleeding problem comes from a low platelet or a low functional fibrinogen activity, thereby guiding the clinician to appropriate treatments. Similarly, prothrombotic patients can be diagnosed with either high platelet activity or high functional fibrinogen activity, or both. Fibrinogen is an important component of both primary and secondary hemostatis, participating in both reversible and irreversible platelet aggregation. In secondary hemostasis, fibrinogen is cleaved and converted to fibrin to form the fibrin matrix (Corporation, H., *Guide to Functional Fibrinogen.* 2009).

EXAMPLE 6

Process for Feature Extraction

An extensive effort was completed to determine the feature correlation between T2Coagulation and TEG curves. The two primary features in the TEG curves for which correlations were sought were R and maximum amplitude (MA). All feature extraction was performed using T2A, T2B, AmpA, and AmpB curves that were smoothed across 1/15 of the total curve, or over every 40 data points.

Figure 5:
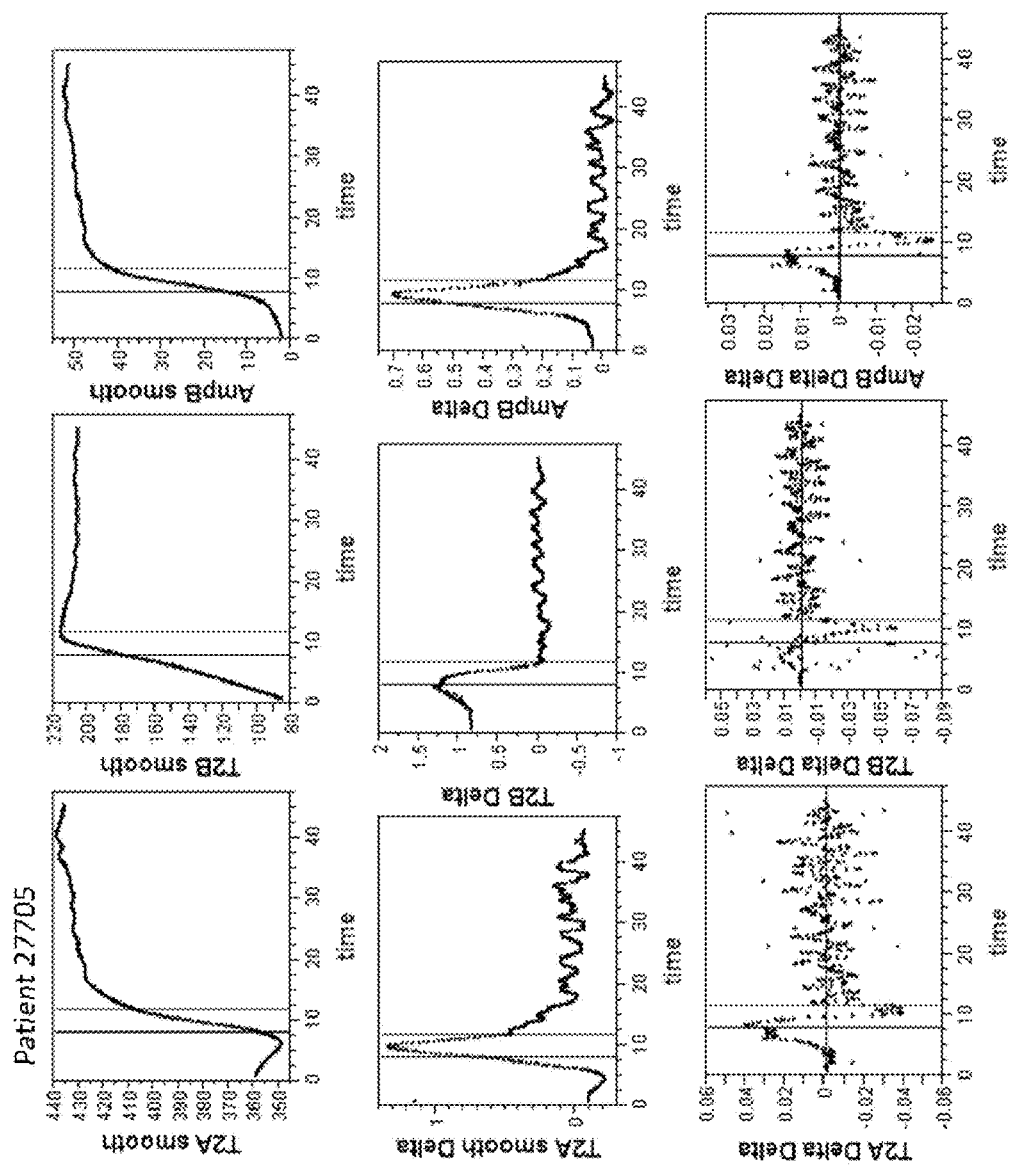
FIG. 5 is a set of exemplary processed T2Coagulation curves for a single patient. The original T2A, T2B, and AmpB curves are shown on the top row. The middle row depicts the first derivative of the curves, and the bottom row depicts the second derivative of the curves.

Feature searching was based on several time points in the T2Coagulation curves. All features of a curve were built from the top candidate for R, which was determined by the time at which the second derivative of the T2A curve reaches a maximum value, by means of a simple numerical calculation. This point in time is referred to as "PossibleR." Also used in feature extraction were the time at which T2B is at a minimum or maximum value, and the time at which T2A is at a minimum or maximum value. FIG. 5 illustrates T2Coagulation curves for a single subject with the first and second derivatives of the T2Coagulation curves.

There can be spurious data points, particularly in the first and second derivatives. So the minimum and maximum values were defined as the extreme points nearest the first time T2A achieves a maximal second derivative. After identifying these time-points in the T2Coagulation curves and in the first and second derivatives of the T2Coagulation curves, several different features were calculated from the time-points, combinations of time-points, numerical derivatives, and differences in T2Coagulation curves. These features were compared to the TEG R, MA, and $MA_{PLATELET}$ values.

Standard regression analyses were used to determine the strength of feature correlation. Two terms were used to aid in the search for features, the Pearson product moment correlation (r) coefficient and the coefficient of determination ($R^2$) term. The r term was used as a general guide in mining for promising correlations and the $R^2$ term was used as a measure of how good the correlation actually was.

Over 90 features were tested. Example features include the value of the first numerical derivative at PossibleR; the slope of T2A at the maximum acceleration of T2A; the difference between the maximum and minimum values on the T2B curves; and the slope between the minimum T2A and maximum T2A values.

T2A+Partial T2B Curves

Figure 6:
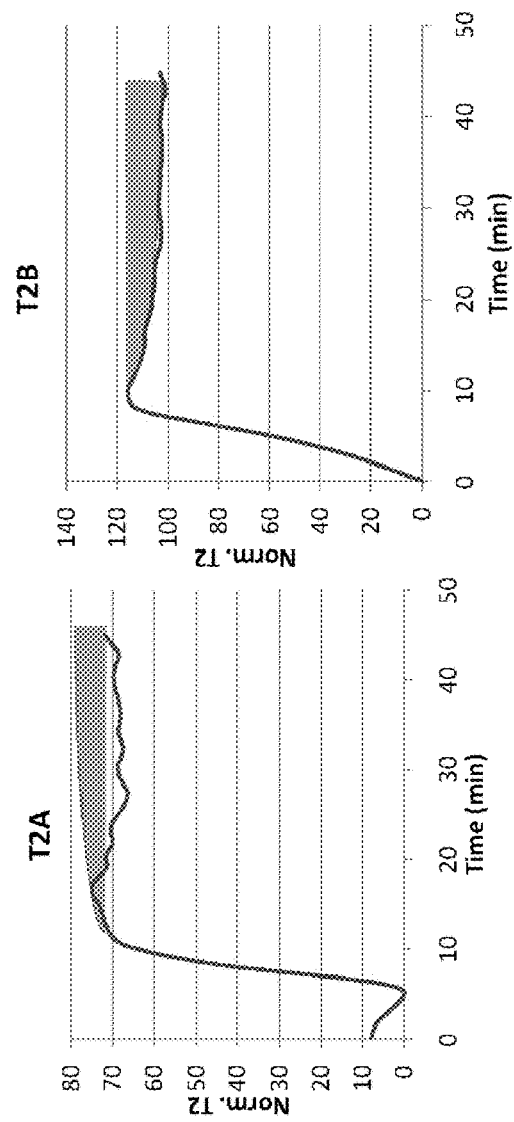
FIGS. 6A-6C depicts the manner in which a T2A+pT2B curve is calculated: A T2A plot that shows how the addition of pT2B will affect the shape of the T2A curve (FIG. 6A); a T2B plot that shows how pT2B is calculated by taking the difference between the maximum T2B value and the actual T2B value for all time points after the maximum T2B value is reached (FIG. 6B); and a T2A+pT2B plot is generated by adding the shaded portion in the T2B curve to the T2A curve, in the same time register (FIG. 6C).

In one example of feature extraction, the T2A and T2B curves can be combined to give a T2A+partial T2B curve that was useful in searching for a correlation between the T2Coagulation curves and the TEG MA value. This combined curve was designated as "T2A+pT2B" and calculated by identifying the point in time where T2B is at a maximum and creating a vector that consists of the absolute value of the difference between that T2B value and all subsequent T2B values. This vector is then added to T2A on the same time register. FIG. 6 shows an example of how the T2A+ pT2B curve is calculated. The T2A+pT2B curve mimics the top half of a TEG curve.

Figure 7:
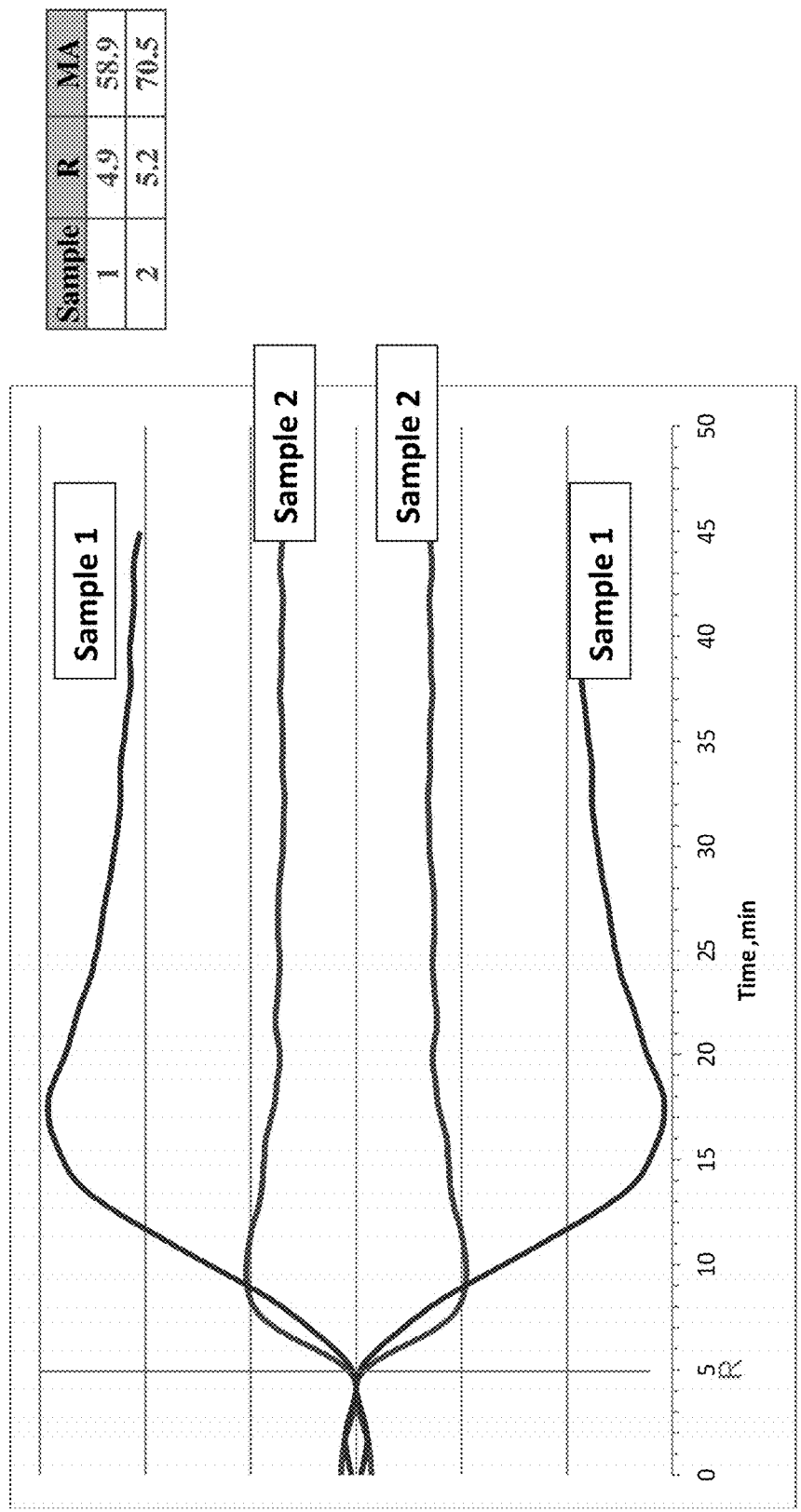
FIG. 7 is a T2Coagulation curve where data shift and reflections were conducted on the extracted data to mimic TEG tracing. The figure illustrates that water probing reveals early changes in microscopic order that may allow for the collection of additional information from before the clotting time R is observed.

The T2A+pT2B curves, generated as described above, generated a potential correlation with TEG MA. A feature was identified that consisted of the change in T2 signal between the T2 at T2 R and the average T2 over the final 50 points on the T2A+pT2B curve. This feature followed an inverse correlation with MA, which was consistent with our initial impression for an MA correlation (see FIG. 7). That is, the maximum T2 change for a T2A+pT2B curve was inversely correlated with the TEG kaolin MA value. Across a large set of samples this feature gave a correlation with $R^2$ values between 0.39 and 0.55. These $R^2$ values may arise from the T2Coagulation T2A curve being sensitive to different aspects of clotting, such as platelets, than what the TEG is sensitive to.

Pre-Clot T2A Value

Figure 8B:
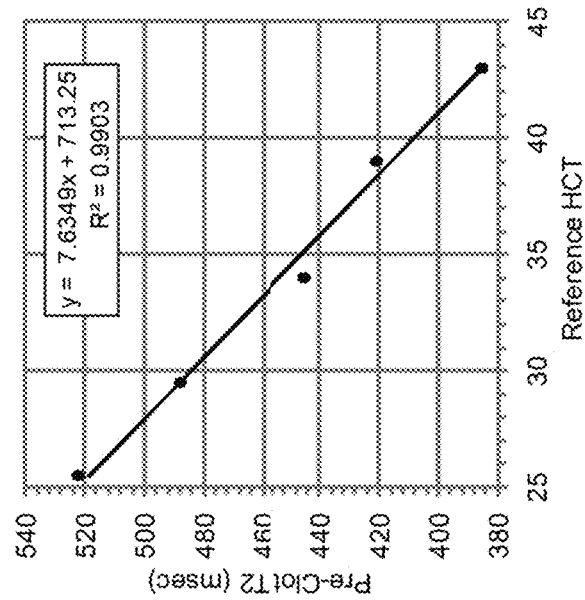
FIGS. 8A and 8B depict graphs showing that the T2 signal for unclotted blood varies inversely with hematocrit levels. The T2 signal for unclotted blood varies inversely with hematocrit (HCT) levels.
Figure 8A:
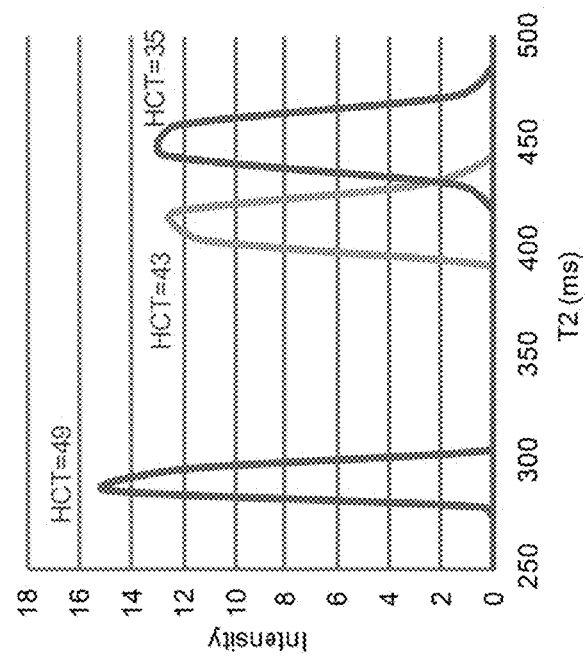

The hematocrit of a blood sample could be calculated from the single, initial water population in the sample prior to clotting. Prior to clot formation, this single water population corresponds to the T2A values established using the bi-exponential fit method described in Example 2. The initial T2A value of a sample was found to have an approximately inverse linear correlation with the hematocrit measured using standard methods known in the art. A calibration curve was established by creating a set of four standards at different dilutions using blood drawn from a single patient. The hematocrit and the initial relaxation rate observed for water population A prior to clot initiation were plotted against one another to generate the calibration curve. Blood samples were drawn from ten patients and queried against the calibration curve. The T2 signal for unclotted blood was found to vary inversely with hematocrit (HCT) levels. As shown in FIG. 8a, distinct patient samples spanning a wide range of HCT reference values demonstrates this generally. Applying calibration methods to a single patient sample diluted across a range of HCT, a depicted in FIG. 8b shows the linear dependence on HCT. FIGS. 8a and 8b show that it is possible to use the methods of the invention to calculate the hematocrit of a blood sample.

EXAMPLE 7

Correlation Between Extracted Magnetic Resonance Parameters and Clotting Behaviors Determined by TEG The magnetic resonance parameters extracted from the measured average NMR relaxation rate data may be correlated with clotting behaviors determined by TEG. Table 2 illustrates the correlation between the extracted T2A values and the clotting time parameter "R" measured using a TEG Hemostatis Analyzer.

The TEG Hemostasis Analyzer provides quantitative and qualitative measurements of the physical properties of a clot (Samara et al., *Thromb. Res.* 115:89-94, 2005). In the present example, the maximum amplitude (MA) and the coagulation time (R) were measured for the thrombin generated clot sample. MA is an indicator of the viscoelasticity of clot formation or clot strength and is dependent on platelet aggregation and fibrin formation and polymerization. R is the period of time of latency until initial fibrin formation and has been correlated with the velocity of thrombin generation.

From plots of AmpA and AmpB measurements, T2A measurements, and T2B measurements it was observed that early portions of the extracted data curves may provide indications of a clotting behavior (e.g., fibrinolysis or LY30) that is not available from the corresponding TEG curves.

TABLE 2

Correlation between extracted magnetic resonance parameters and clotting behaviors determined by TEG (data shown in minutes)

| Sample | R values | |
|---|---|---|
| | TEG | T2Coagulation |
| 1 | 6.9 | 6.5 |
| 2 | 7.3 | 7.5 |
| 3 | 5.5 | 6.0 |
| 4 | 6.6 | 7.0 |
| 5 | 5.2 | 6.0 |
| 6 | 7.8 | 8.0 |
| 7 | 4.9 | 5.0 |

T2Coagulation Correlation for Clotting Time (R)

Figure 9:
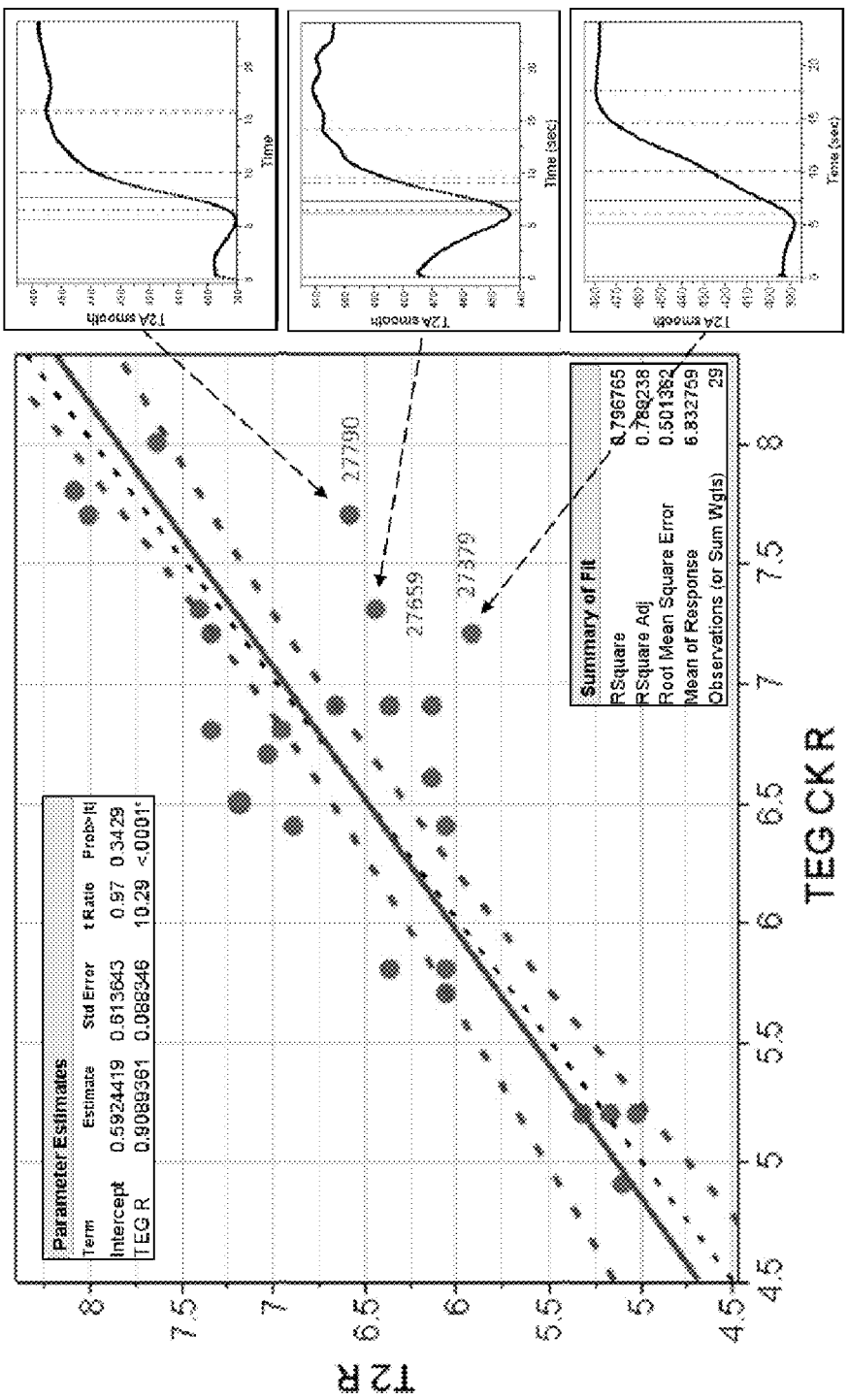
FIG. 9 depicts a correlation plot between T2 R and TEG R for CK runs; the solid line represents the regression line calculated from the correlation plot.

A method of correlating the clotting time (R) with a T2Coagulation feature was developed based on obtaining the second numerical derivative of T2A in an automated way, as discussed above. Across 25 runs, a $R^2$ of 0.80 (FIG. 9) was observed between T2 and TEG for the R (whole blood clotting time) values. The T2Coagulation curves used for this correlation were kaolin runs where SSE≥2. Three outlier runs are highlighted in FIG. 9 with their T2A curves shown to the right. In all three cases, the T2A curve achieves maximum acceleration (T2A"=0) prior to the R TEG time.

T2Coagulation Correlation for Platelet-Associated Clot Strength ($MA_{PLATELET}$)

Figure 10:
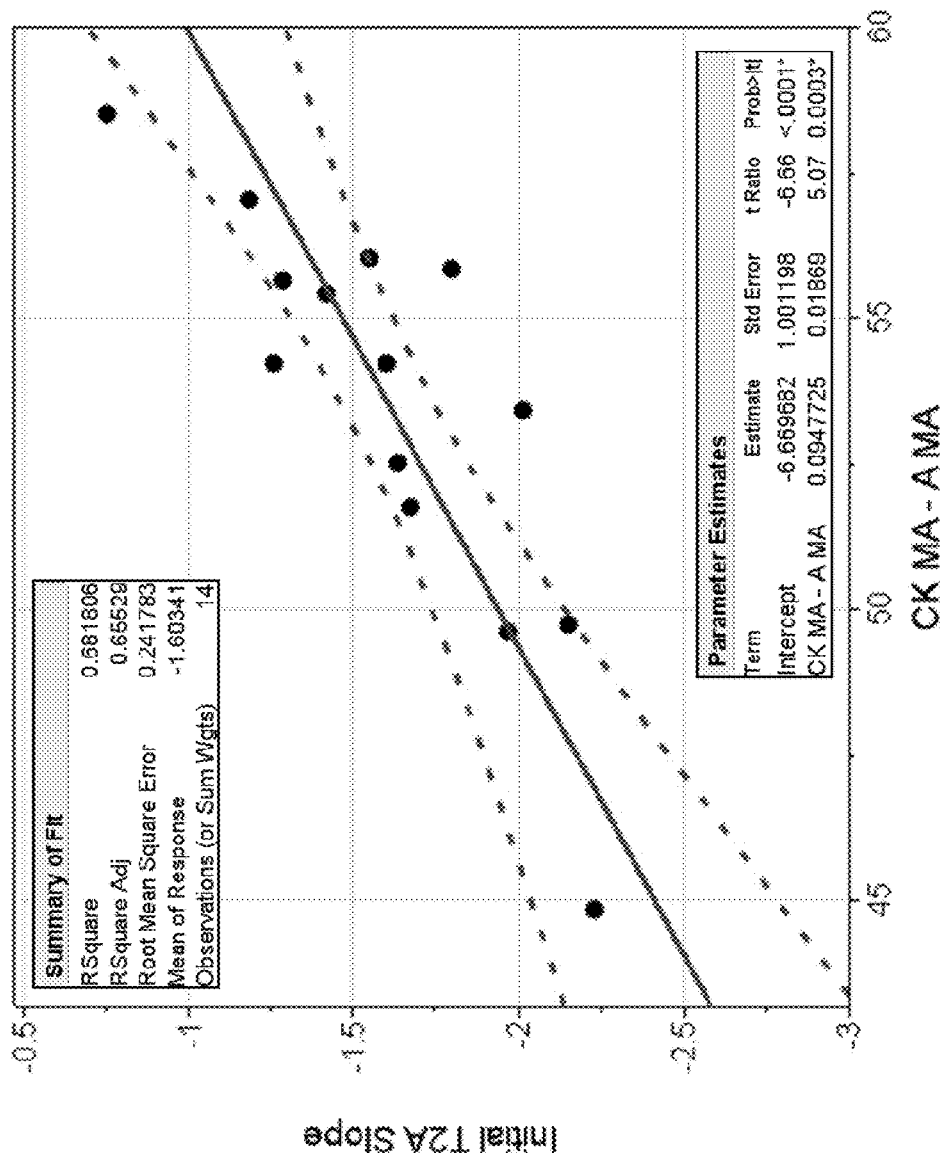
FIG. 10 shows the correlation between the T2Coagulation feature "T2A initial slope" and the TEG term ($MA_{THROMBIN}$–$MA_A$), which corresponds to platelet-associated clot strength ($MA_{PLATELET}$).

Several features were explored for correlating TEG MA times and T2Coagulation features using kaolin runs. The most prominent correlation found for kaolin runs was the T2Coagulation feature between time zero and the minimum T2 value, which is right before the T2 R feature. This is the typical initial decrease in the T2A curves. The slope of the T2A signal between time zero and the minimum T2 value correlates with the TEG $MA_{PLATELET}$ value. Because TEG cannot measure the platelet activity directly, the thrombin-induced platelet contribution to clot strength is derived by subtracting the MA term from an activator, or A, run ($MA_A$) from the MA term from a kaolin run (also referred to as $MA_{THROMBIN}$). FIG. 10 shows the correlation between the TEG term $MA_{THROMBIN}-MA_A$, or MA from a CK run minus MA from an A run for 14 T2Coagulation runs and 28 TEG runs. As with the R correlations, SSE≥2 was used. To get the $MA_{PLATELET}$ term with TEG, two different TEG curves must be acquired and the user must conduct manual arithmetic to determine the platelet contribution to clot strength. However, with T2Coagulation, this information is available within the first 6 minutes of a single T2Coagulation run that is much easier to set up.

T2Coagulation Correlation for Functional Fibrinogen-Associated Clot Strength ($MA_{FF}$)

Figure 11B:
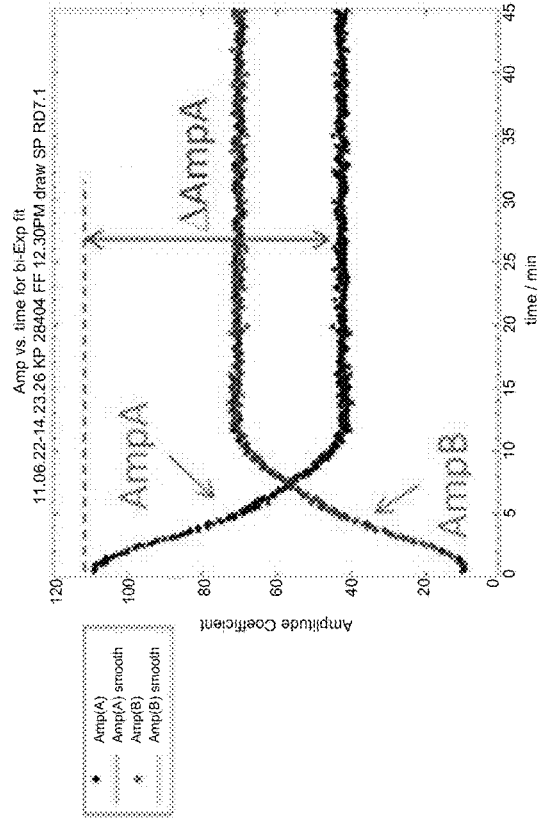
FIGS. 11A-11C shows T2Coagulation results from a functional fibrinogen titration in 50% citrated whole blood. Two T2Coagulation Amplitude plots show AmpA and AmpB on the same intensity scale.
Figure 11A:
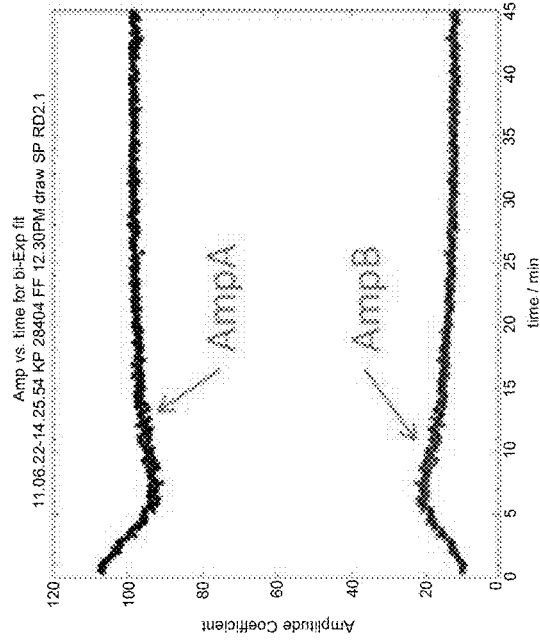
Figure 11C:
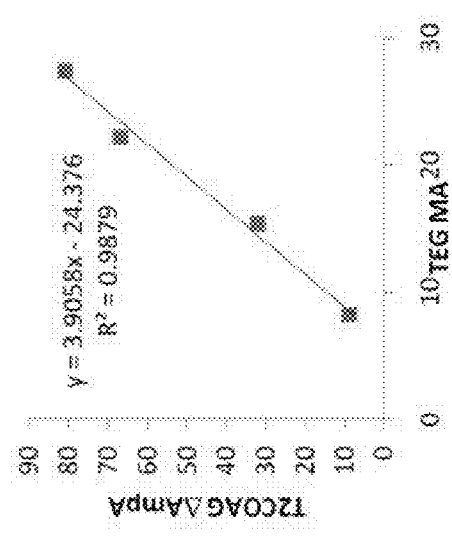
Figure 12A:
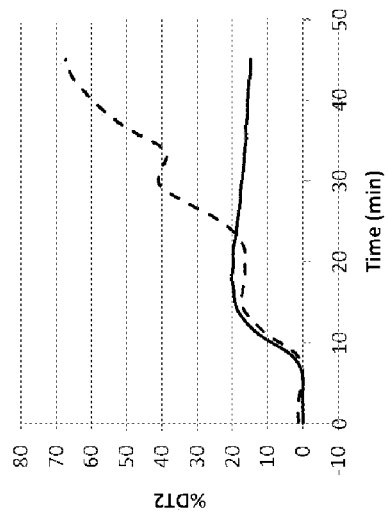
FIGS. 12A-12D depict the T2Coagulation sensitivity to fibrinolysis. T2A curves for two different patients are shown in FIGS. 12A and 12B; and T2B curves are shown for the same two different patients in FIGS. 12C and 12D. The solid lines show a kaolin curve in the absence of fibrinolysis and the dashed lines show a kaolin curve in the presence of fibrinolysis.
Figure 12B:
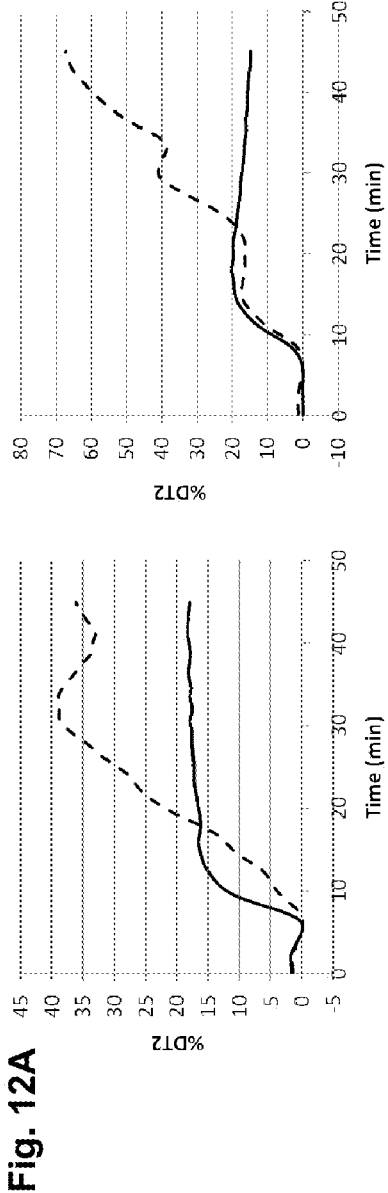
Figure 12C:
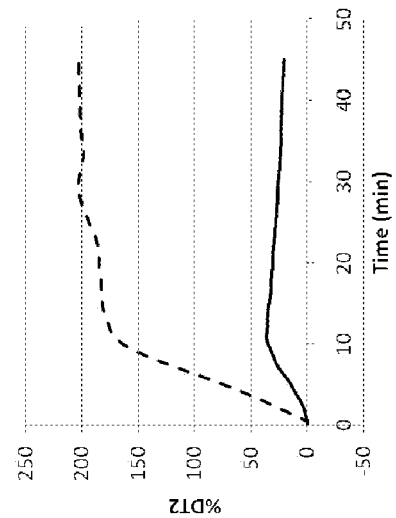
Figure 12D:
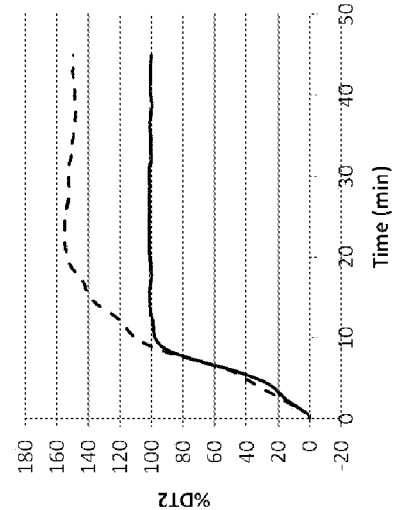

Clotting behaviors may be determined by including additives in a blood sample prior to collection of NRM relaxation data. Fibrinogen can be added to a sample to effectively titrate the range of MA values. FIG. 11 shows the T2Coagulation curves for the functional fibrinogen titration and clear evidence for correlation between the MA of an FF run and a feature from the T2Coagulation curve. This T2Coagulation feature was calculated as the difference between the initial and final T2Coagulation AmpA values (ΔAmpA). Fibrinogen was added to samples at three different concentrations (0.63, 1.25, and 2.5 mg/mL). As can be seen in FIG. 11(c), there was a strong correlation between ΔAmpA and TEG MA for these functional fibrinogen (FF) ($MA_{FF}$) runs compared with a sample containing no added fibrinogen. Fibrinogen titrations were conducted for two other patient samples and correlations above 0.9 and as high as 0.98 were obtained. In this protocol, the citrated whole blood was diluted to 50% of its original concentration.

T2Coagulation Correlation for Percent Lysis 30 Minutes after MA (LY30)

A correlation was observed for the LY30 term that is used to detect fibrinolysis. Five different healthy patient samples were used to test whether T2Coagulation was sensitive to fibrinolysis. Addition of tissue plasminogen activator (TPA) was used to simulate fibrinolysis by adding it at two levels to healthy patient blood. TPA cleaves fibrin as it forms. It was observed that fibrinolysis can be detected within 10 minutes on T2Coagulation, which is less than half the time required for detection on TEG. For all five patients there was a clear difference between healthy and fibrinolytic samples. FIG. 12 shows T2Coagulation data for T2A and T2B curves for the non-fibrinolytic (solid line) sample and fibrinolytic sample (dashed line).

Figure 13:
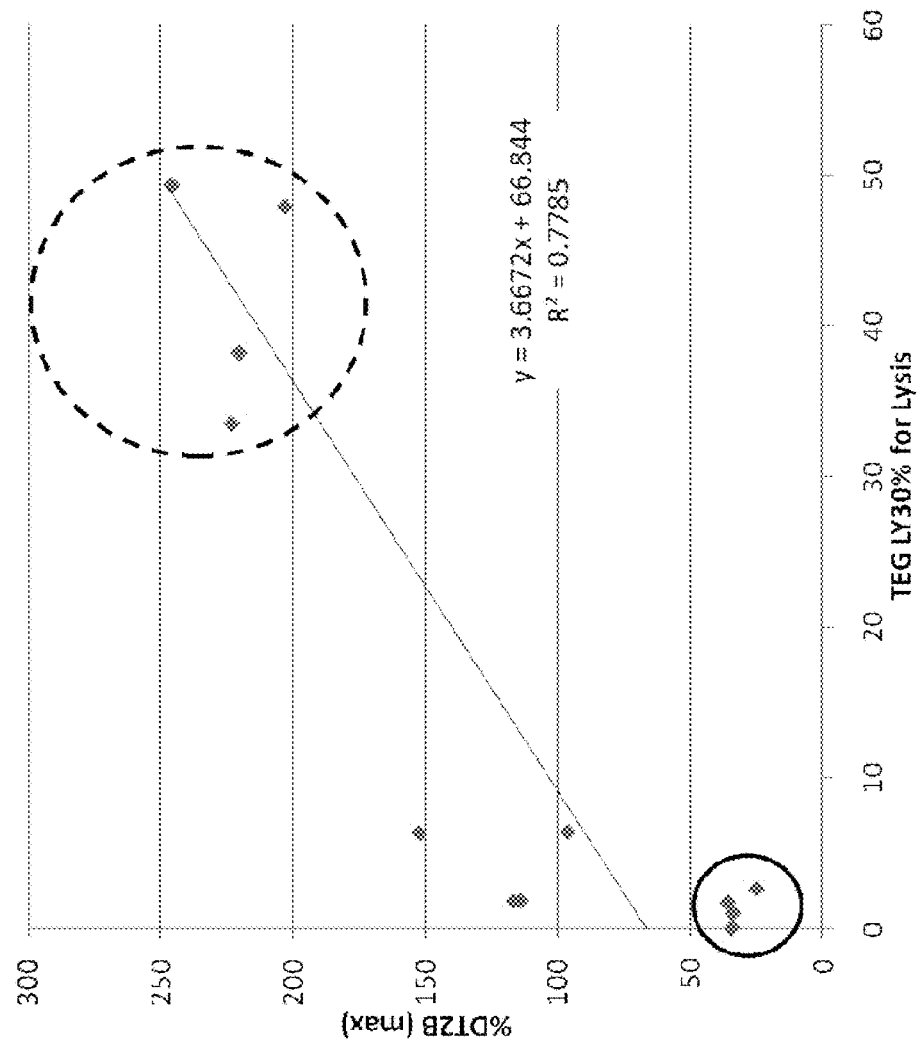
FIG. 13 depicts a correlation plot between T2Coagulation and TEG for healthy and fibrinolytic samples. Data points within the solid circle are healthy K runs. Data points within the dashed circle are for fibrinolytic K runs. Data points outside both circles are for partially fibrinolytic runs.

There is a strong correlation for the change in the T2B signal and the LY30 term from TEG, as shown in FIG. 13. There are several potential features that can be used for this correlation. Three that were investigated were the difference between (i) the minimum and maximum T2B values (FIG. 13), (ii) the average of the T2B values over the final 25 minutes of the T2B curves, and (iii) the T2B values at 10 minutes. All had correlations with $R^2$ values between 0.72 and 0.79. The correlation plots show a higher sensitivity of T2Coagulation for fibrinolysis than TEG. This can be seen by the groupings for the different levels of fibrinolysis in FIG. 13. The healthy patient samples are circled with the solid line. The fully fibrinolytic samples (containing 118 ng/mL of Cathflo®, recombinant alteplase manufactured by Genentech) are circled with the dashed line and the partially fibrinolytic samples (containing 60 ng/mL of Cathflo®, recombinant alteplase manufactured by Genentech) are not circled. The T2Coagulation T2B term can be detected in as little as 10 minutes, which is much faster than the TEG LY30 term can be detected, indicating the utility of the T2Coagulation signal for more rapid measurement of fibrinolysis.

Clotting Time, PT/INR, and aPTT

The sensitivity of T2MR to clot formation in blood and plasma can be used to measure clotting times, such as PT/INR, aPTT, and TEG R.

Clotting times were measured by T2MR by first establishing a time zero T2 value (i.e., by taking the first point or some sort of average or linear fit to the first 5-10 data points) of the T2 time curve, and second identifying the time point (i.e., the clotting time or PT time) in the T2 time curve when the T2 value had changed by a predetermined amount (e.g. 5% or 10%) indicative of clotting in the sample. From the observed PT clotting time the INR was calculated using the methods described in Jan et al., Clin. Chem. 35:840 (1989).

Figure 14A:
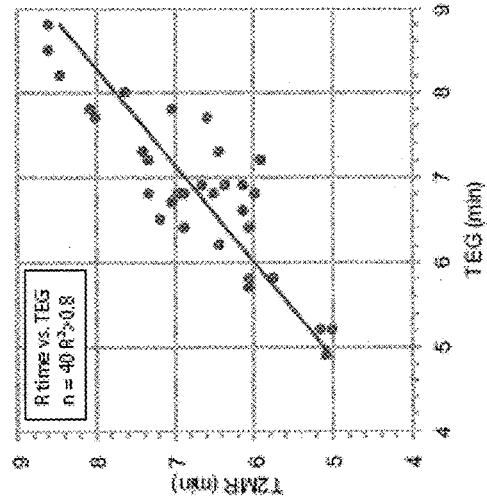
FIGS. 14A-14D depict correlation plots comparing the methods of the invention to existing modes of analysis. A preliminary correlation for PT/INR with Stago was demonstrated using thromboplastin reagent (Thrombotest, Axis Shield) and 1:5 dilution of whole blood for T2MR and the standard reagents and plasma protocol for Stago Start system (see FIG. 14A). Correlation with TEG clotting time was obtained across >40 normal patient samples with non-optimized R2 correlation of >0.8. (see FIG. 14B). PT time correlations with Stago for plasma (see FIG. 14D) and with Hemochron for whole blood (see FIG. 14C) were also found. See Example 7.
Figure 14B:
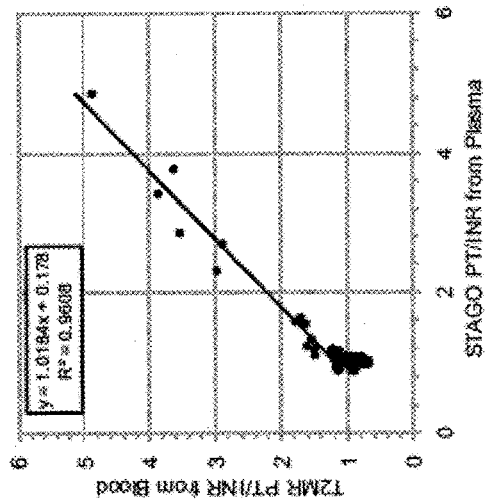
Figure 14C:
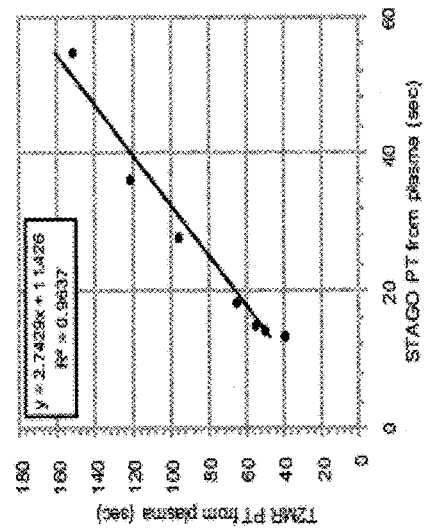
Figure 14D:
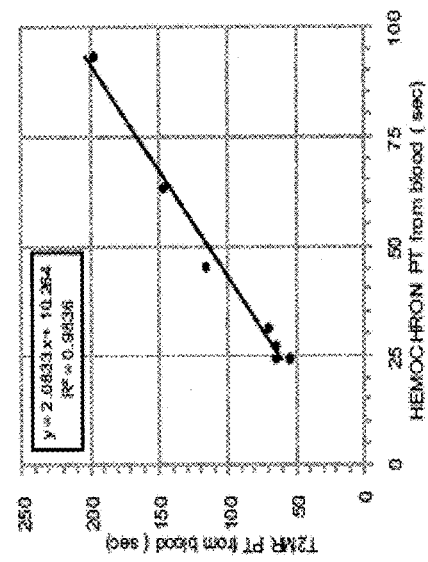

A correlation for PT/INR with Stago was demonstrated using thromboplastin reagent (Thrombotest, Axis Shield) and 1:5 dilution of whole blood for T2MR and the standard reagents and plasma protocol for Stago Start system (see FIG. 14A). 18 normal samples and 24 abnormal samples were tested against a reference range established by 20 normal samples. Abnormal samples with prolonged PT times were obtained by spiking increasing levels of the anti-Xa inhibitor Rivaroxiban (10 ng/mL-1000 ng/mL). Correlation with TEG clotting time was obtained across >40 normal patient samples with non-optimized R2 correlation of >0.8. (see FIG. 14B). PT time correlations with Stago for plasma (see FIG. 14D) and with Hemochron for whole blood (see FIG. 14C) were also found.

EXAMPLE 8

T1 Relaxation Measurements

In addition to being able to measure T2 measurements, T2readers can be configured to measure T1 measurements. T1 measures different physical properties of the hydrogen atom spin system in the sample. Therefore, T1 data provides alternative and complementary information about blood clotting compared to T2 data. While conventional T1 measurements are time consuming (2-3 minutes) due to the step-wise nature of acquiring the T1 signal, a z-refocused echo (ZRE) method was used to acquire T1 within less than 5 seconds. Measurements of T1 relaxation curves for native and clotted whole blood we made and a sensitivity of T1 to blood clotting was observed (unclotted whole blood T1=787 ms; clotted whole blood T1=860 ms).

EXAMPLE 9

T1/T2 Hybrid Detection Methods

T1/T2 hybrid detection methods are known in the art (Edzes, *J. Magn. Reson.* 17: 301-313, 1975; Sezginer et al., *J. Magn. Reson.* 92: 504-527, 1991, which are hereby incorporated by reference). These methods and related methods may be used in the present invention to assess magnetic resonance parameters values and/or establish T2Coagulation curves.

T1 is typically sampled by means of an inversion-recovery sequence. Inversion recovery sequences can take several minutes to acquire depending on the precision of the measured relaxation time that the user wants to achieve, which is dictated by the number of data measurements used in the pulse sequence. The details of the inversion recovery sequence will not be described here, as they can be looked up in any standard NMR textbook.

A T1ZRE pulse sequence allows for the measurement of T1 over the time required for the magnetization to completely relax. (~3-5×T1). This is achieved by inverting the magnetization with a 180° pulse and then sampling the magnetization while the magnetization returns to equilibrium by measuring its magnitude and returning it to its original −z position with a series of pulses.

The time that it takes to sample the magnetization is called $\tau_c$, and the time between samplings is $\tau_r$. The time after the start of $\tau_c$ until the actual measurement is $\tau_m$. The measured relaxation constant is a combination of $R_2$ and $R_1$ and is referred to as $R_{12}$. The three terms are related by $$R_{12} = (1-p)R_1 + pR_2 \tag{11}$$

where $p = \tau_c/\tau_r$. From this relation, one can see that R12 goes to R1 when p goes to 0.

$\tau_r$ will depend on the total number of points and the total duration of the measurement. For T2Coagulation measurements, it was 30 points over ~3 seconds for a $T_r$ of 100 milliseconds. The $\tau_c$ term can be calculated from the pulse sequence and is essentially equivalent to 3×tau or 750 Accordingly, the p term is equal to 0.0075 and the measured relaxation, or hybrid, T1/T2 (hT12) term should primarily be T1. Sezginer et al. provide a simple equation to derive the T1 measurement from the hT12 signal, which is $$\frac{1}{T_1^{meas}} = \frac{T_b}{T_1(4t_{cp} + T_b)} + \frac{4t_{cp}}{T_2(4t_{cp} + T_b)} \tag{12}$$

where $T_1^{meas}$ is hT12, $T_1$ is T1, $T_b$ is the duration between the two measurements, $t_{cp}$ is half of the inter-echo delay or tau, and $T_2$ is the measured T2 time.

The above description is simply illustrative of how this hybrid relaxation time can be measured. There are other pulse sequences that can be used to measure hybrid relaxation constants and derive T1 in a rapid fashion.

Regardless of the pulse sequence used, the inventive concept is directed to rapid acquisition of magnetic resonance relaxation measurements for monitoring coagulation (i.e., blood clotting). Other types of magnetic resonance pulse sequences can be used to monitor the bulk hydrogen signal in the sample during coagulation. Examples include T2, T1, T1/T2 hybrid times, their inverse terms of R2, R1, R12, and pulsed NMR measurements commonly used for materials analyses on relaxometers such as free induction decay (FID) based analyses, fast Fourier transform based analyses (FFT). FID analysis commonly discriminates between rapidly decaying signals and slowly decaying signals. The intensities of these two signals can be compared, as can their decay constants. These pulse sequences have been commonly used for fat analysis, fat content and solid to liquid ratio, solid fat to liquid ratio, hydrogen content determination, oil content, solids content, and total fat content determinations, oil water emulsions, and fat and moisture determinations. Similar real-time or kinetic measurements can be performed with those NMR parameters on samples that are undergoing a coagulation reaction.

Alternative relaxation measurements are attractive to provide: (1) more information of the clotting process; (2) specific information not captured by the T2 measurement; and (3) normalization for factors that both T2 and the new parameter are sensitive to. To describe point 3 more, if, for example, T1 measurements are sensitive to variations in patient to patient but T1 does not contain the coagulation information then there should be an algorithm to use the T1 curve to "subtract out" the part of the T2 signal that arises from undesired sensitivities in clinical samples. Such undesired sensitivities may be variations in hematocrit, platelet count, etc.

To demonstrate the concept, we measured a CK clotting curve on a Bruker minispec. The experiment was conducted in a sample volume of 300 μL and inside of a glass NMR tube. This relaxometer had a pulse sequence that could measure both T2 and hybrid T12 (hT12) relaxation times in a rapid successive fashion. T1 was derived by equation 12.

The resulting T2Coagulation curves showed very similar shape and features to the T2Coagulation curves acquired on the T2readers used in the invention. This is confirmation of the other T2Coagulation curves because the Bruker minispec used has a very different detection coil, magnet, and curve fitting algorithm than the T2readers. Under the described pulse sequence conditions the T1/T2 hybrid is primarily T1. In this experiment the T1/T2 hybrid signal was acquired in an interleaved fashion. A T2 signal was acquired using a CPMG sequence and then the T1/T2 signal was acquired using the T1ZRE sequence. The signals can be combined with each other to generate new curves calculated by dividing the T1/T2 hybrid (primarily T2) by T2A and useful in the methods of the invention for assessing hypercoagulability and/or hypocoagulability of a blood sample.

EXAMPLE 10

Acrylamide Synthetic Clotting Control

An acrylamide gel polymerization was used as a synthetic control for T2Coagulation measurements. A set of acrylamide gels were prepared using deionized water, 40% acrylamide, 0.5 M Tris pH 6.8 buffer, and 10% ammonium persulfate in the amounts listed in Table 3 to form a set of mixtures. The mixtures were incubated at room temperature for 30 minutes. 36 µL of each mixture was saved in a set of separate PCR tubes for use as controls. 2 µL of tetramethylethylenediamine (TEMED) was added to each mixture. After 30 minutes, a T2 measurement of each control and polymerization reaction was taken.

TABLE 3

Composition of acrylamide gels

| | Sample | | | | | |
|---|---|---|---|---|---|---|
| | 3% | 6% | 10% | 15% | 20% | 40% |
| Deionized water (µL) | 1310 | 1160 | 960 | 710 | 460 | |
| 40% Acrylamide (µL) | 150 | 300 | 500 | 750 | 1000 | 2000 |
| 0.5M Tris pH 6.8 buffer (µL) | 500 | 500 | 500 | 500 | 500 | |
| 10% Ammonium persulfate (µL) | 20 | 20 | 20 | 20 | 20 | 20 |

The percent change in T2 was calculated by comparing the T2 values of the TEMED treated sample and the corresponding control sample. The measured data is shown in Table 4.

TABLE 4

Percent change in T2 times of acrylamide gels

| Sample | Control, T2 msec | Polymerized, T2 msec | % T2 change |
|---|---|---|---|
| 3% | 1386.3 | 1351.16 | 3 |
| 6% | 1339.31 | 1107.84 | 17 |
| 10% | 1326.36 | 828.29 | 38 |
| 15% | 1355.67 | 604.56 | 55 |
| 20% | 1235.29 | 450.85 | 64 |
| 40% | 1200.66 | 145.87 | 88 |

The 15%, 20%, and 40% acrylamide gels demonstrated the largest % T2 changes. These reactions were chosen for time course T2 measurements. The 15%, 20%, and 40% acrylamide gels were prepared according to Table 3. Upon addition of TEMED, each sample was immediately placed into a T2 T2reader and measurement was started. The time course data revealed that the overall change in T2 and speed of reaction depends on the percent acrylamide. This is a reflection of the different polymer densities for these different reactions. The sensitivity of T2 to the polymer gel composition is likely due to the sensitivity of T2 to a change in the average length of water diffusion during the time course of a single T2 measurement.

Superparamagnetic nanoparticles can be used with synthetic clotting reactions (e.g., the acrylamide gel formation). When, the 40% acrylamide gel was polymerized in the presence of ~800 nm carboxy Sera-mag nanoparticles (1 µg/mL nanoparticles), the initial part of the T2 time curve was flattened. The CPMG parameters used in the T2 measurements described above are as follows: pulse width=6.8 µs; radiofrequency blanking width=1 µs; 90-180 spacing=249.6 µs; num 180s=7000; total excitation=3494.902 ms; repetition (Tr)=1000 ms; receiver phase=0; 90 phase=0; and 180 phase=90.

This example is illustrative of how an NMR parameter (e.g., T1 or T2) changes in a sample undergoing a phase change. Increasing the polymer density resulted in a more rapid decrease in T2 and an overall greater decrease in T2, demonstrating the dependence of the T2 signal on polymer matrix density, pore size, and other parameters of the gel Similar results can be obtained with other gels such as Kappa carrageenan gel (gels with the addition of potassium ions), Iota carrageen gel (gels with the addition of calcium ions), sodium calcium alginate, gelatin, among other food products.

EXAMPLE 11

Detection of Bacterial Endotoxin

The methods and device of the invention are used to detect bacterial endotoxin, i.e., cell wall material from gram-negative bacteria. Endotoxin is capable of causing high fevers in humans, and, consequently, injectable drugs and medical devices that contact the blood are frequently tested for the presence of endotoxin. A clotting-based assay for detecting endotoxin relies upon the reaction between bacterial endotoxin and a specific lysate used in the assay. A lysate derived from the circulating amebocytes of the horseshoe crab *Limulus polyphemus* is a particular lysate that can be used. In the assay, the lysate is introduced to a sample to be tested for the presence of endotoxin. If a gel is formed, via a clotting process, endotoxin is deemed to be present. The formation and properties of such a gel are monitored by any of the NMR-based methods described herein.

EXAMPLE 12

T2 Signature Curves

Figure 15:
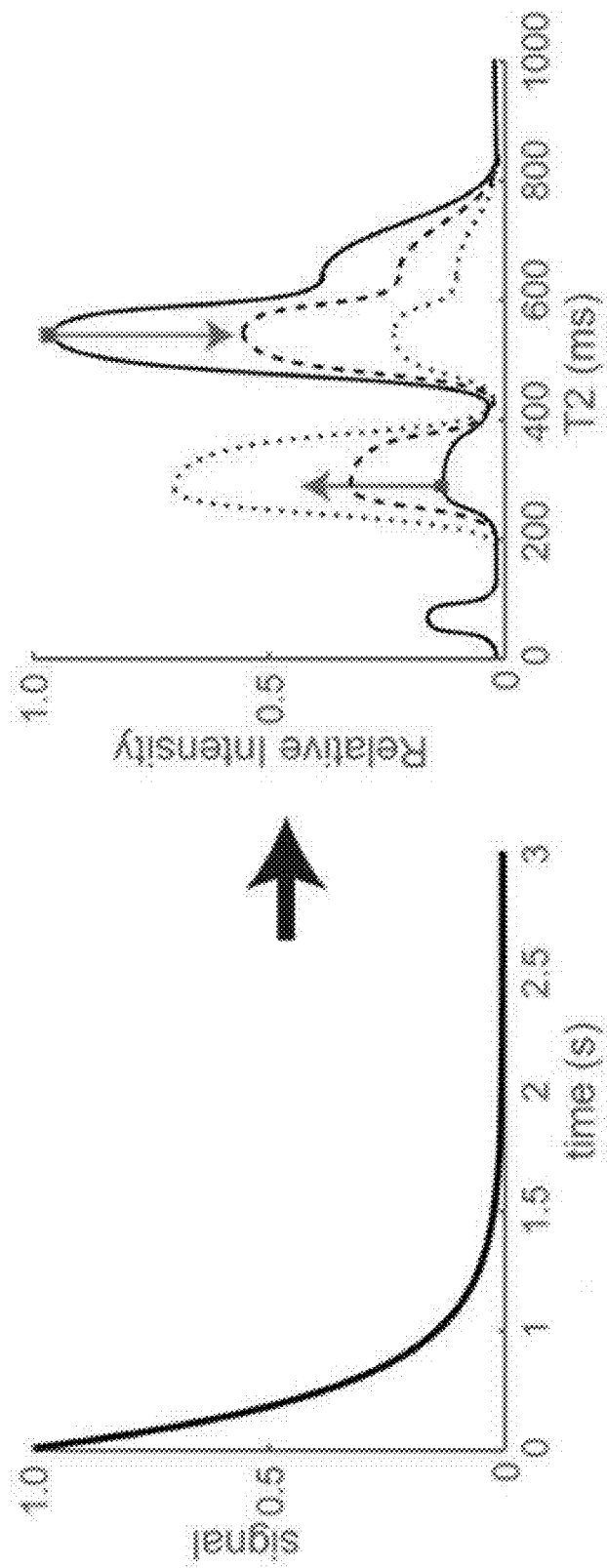
FIG. 15 depicts a T2 decay curve and a corresponding T2 signature curve, with possible changes in signature at the T2 signature curve as a function of changes in the composition of the sample.

NMR data is processed to create a T2 signature curve displaying distinct signals (i.e. maxima) that represent individual water populations within a blood sample. The T2 signature curves are created by applying a mathematical transform (e.g., a Laplace transform or inverse Laplace transform) to a decay curve associated with T2 at a time point during a clotting event. FIG. 15 depicts a T2 decay curve and a corresponding T2 signature curve. The three signals represent three water populations in the blood sample. FIG. 15 also depicts one way in which the signals can change over time.

Figure 16:
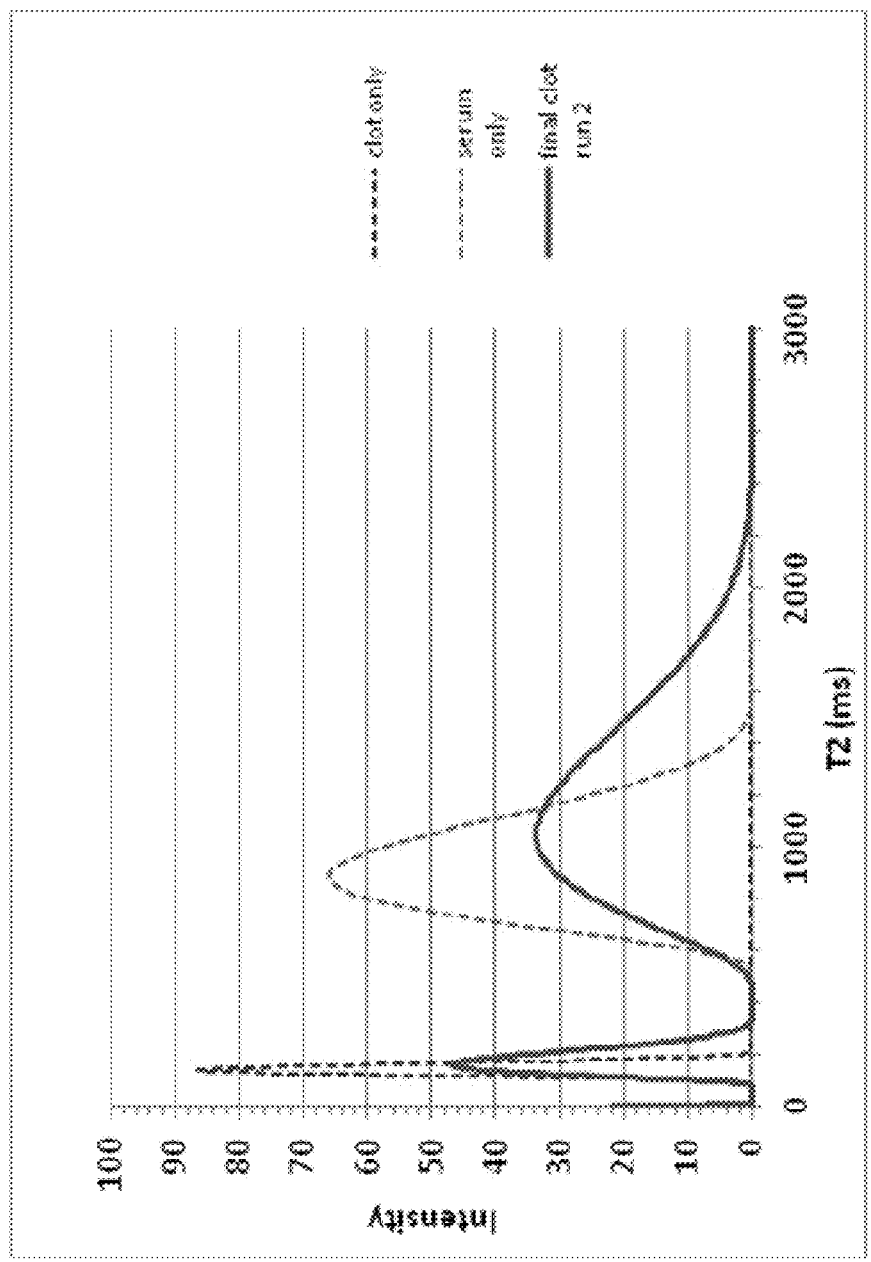
FIG. 16 depicts the inverse Laplace transform of T2 data corresponding to patient sample KP 29476 and separate inverse Laplace transforms of the T2 data obtained from the serum and retracted clot after separation. The plots show that formation of a strong clot results in two distinct water populations (i.e., the population of water in the clot and the population of water in the serum). The signal at the higher T2 times corresponds to the serum-associated T2 signal and the signal at the lower T2 times corresponds to the clot-associated T2 signal.
Figure 18:
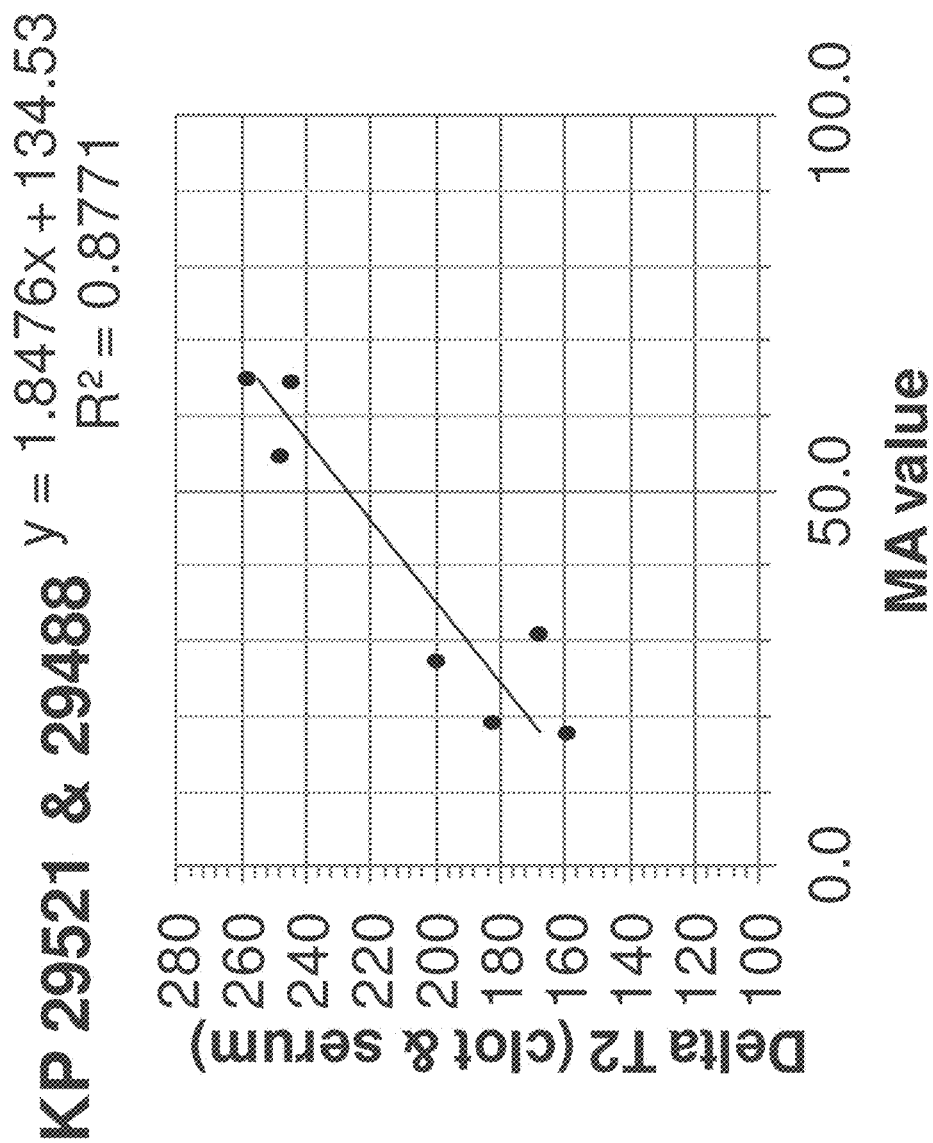
FIG. 18 depicts a graph for two patients correlating clot strength (MA value) with the difference between the clot-associated signal and the serum-associated signal (Delta T2). The data shows that increasing clot strength positively correlates with Delta T2.
Figure 19:
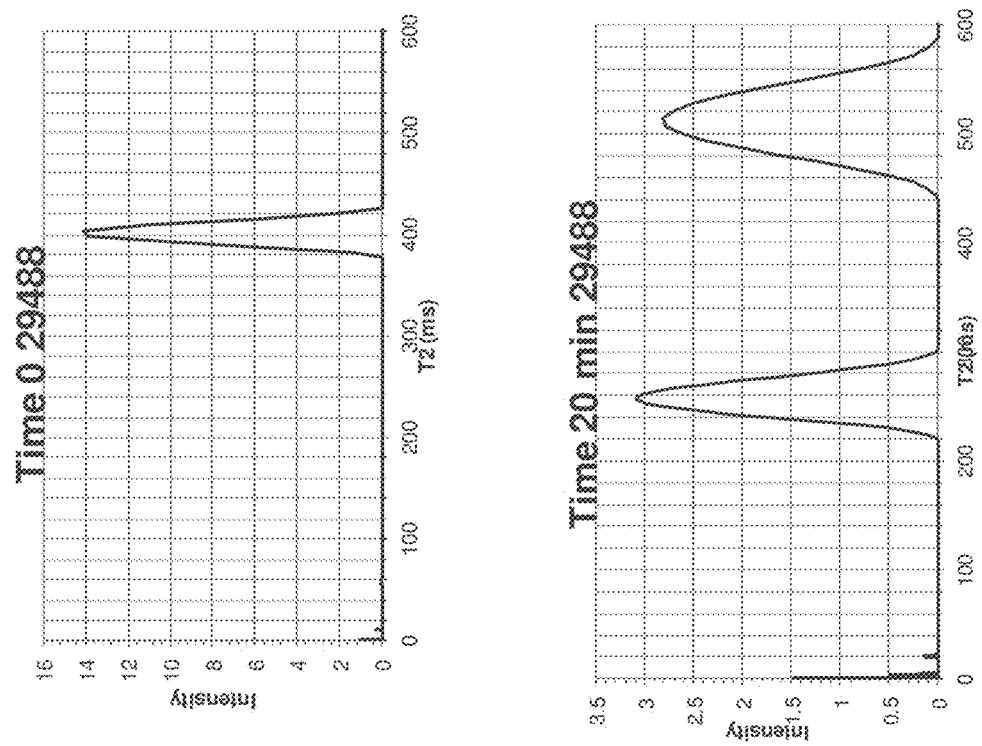
FIG. 19 depicts two T2 relaxation spectra for a patient sample collected on a T2reader at two different time points. The spectra show an initial significant peak at Time 0 that corresponds with the blood in the sample. At 20 minutes, two significant peaks are evident. The peak with a lower T2 time (~200-300 milliseconds) corresponds with the T2 blood clot water environment, and the peak with a higher T2 time (~450-580 milliseconds) corresponds with the T2 serum water environment.
Figure 21B:
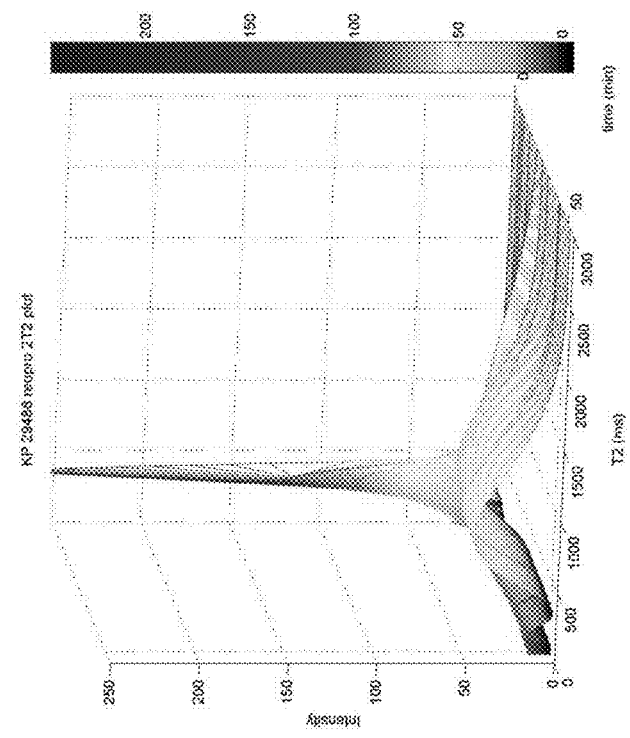
FIG. 21 depicts 3D plots for four samples containing four different concentrations of abciximab, as described in Example 14. The data was collected on a Bruker minispec.
Figure 21A:
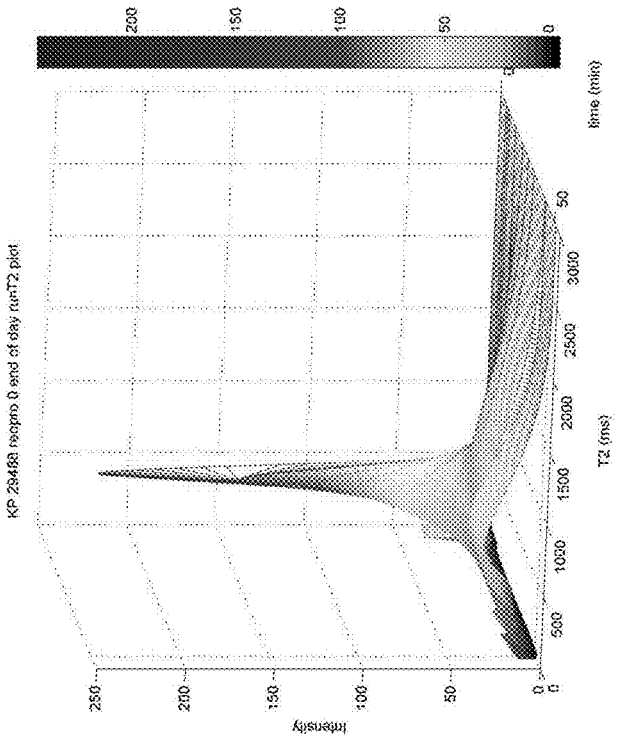
Figure 21D:
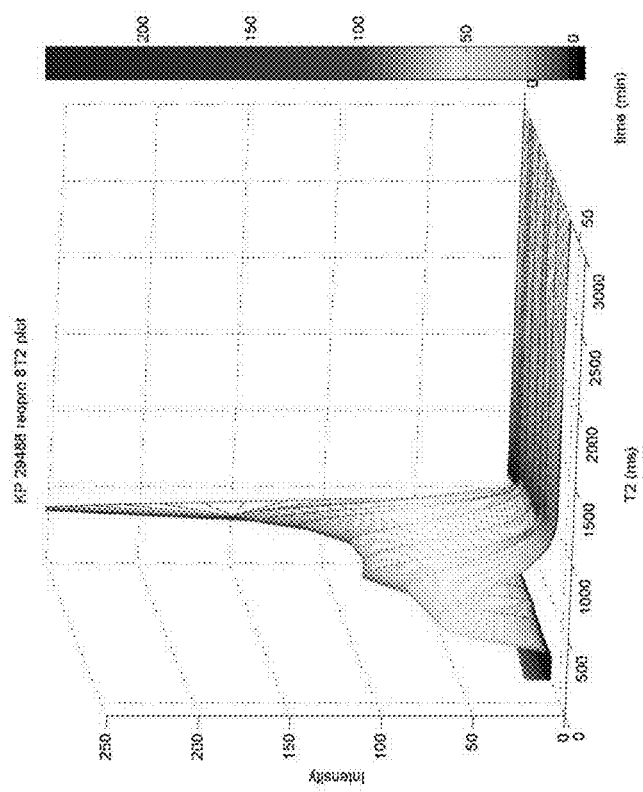
Figure 21C:
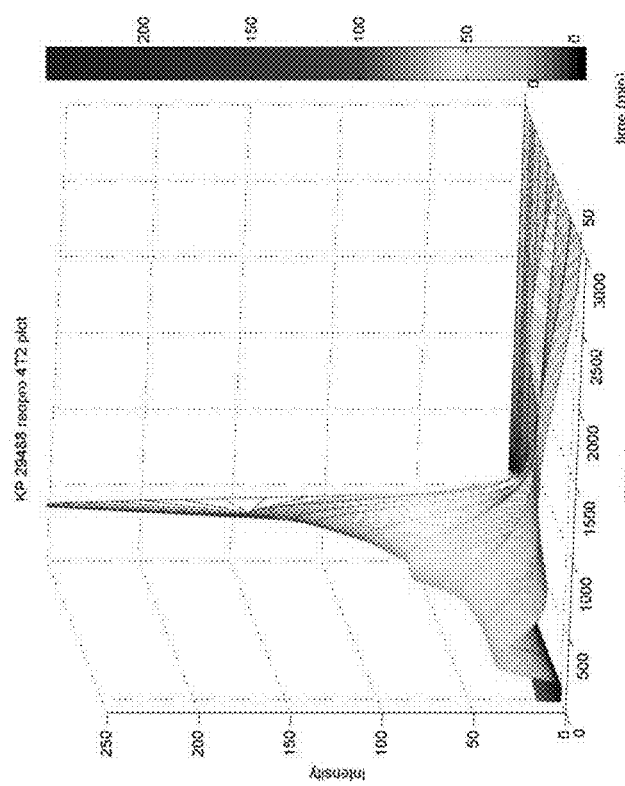

The correlation between the water populations A and B observed in the NMR relaxation data and the components of the clotted sample was confirmed by separating the retracted clot from the surrounding serum and separately measuring the T2 data for these two components (see FIG. 16, the T2 signature curve after clotting is completed). Two T2 relaxation spectra for a patient sample collected on a T2reader at two different time points (see FIG. 18). The spectra show an initial significant peak at Time 0 that corresponds with the blood in the sample. At 20 minutes, two significant peaks are evident. The peak with a lower T2 time (~200-300 milliseconds) corresponds with the T2 blood clot water environment, and the peak with a higher T2 time (~450-580 milliseconds) corresponds with the T2 serum water environment.

Figure 17:
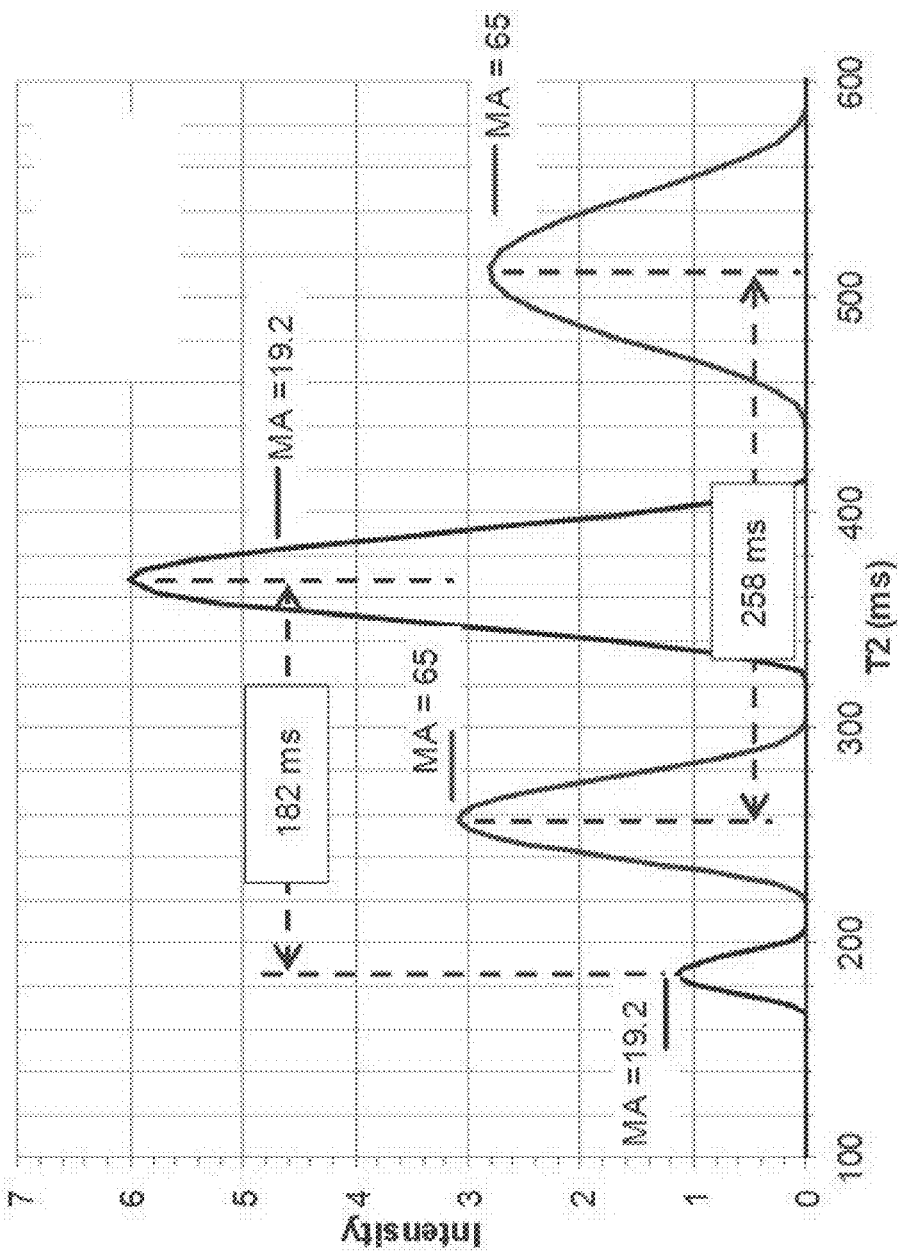
FIG. 17 depicts two overlaid T2 relaxation spectra and the TEG clot strength (MA) for two different samples drawn from the same patient. The sample containing the weaker clot (MA=19.2) exhibited a lower value for the difference between the clot-associated signal and the serum-associated signal (182 milliseconds) than the sample containing the stronger clot (MA=65; 258 milliseconds). The spectra shown in FIG. 17 were collected on a T2reader.

The difference between T2A and T2B (Delta T2) was observed to be correlated with clot strength. FIG. 17 depicts two overlaid T2 relaxation spectra and the TEG clot strength (MA) for two different samples drawn from the same patient. The sample containing the weaker clot (MA=19.2) exhibited a lower value for the difference between the clot-associated signal and the serum-associated signal (182 milliseconds) than the sample containing the stronger clot (MA=65; 258 milliseconds). The data shows that increasing clot strength positively correlates with Delta T2 ($R^2$=0.8771, see FIG. 18).

EXAMPLE 13

3D Plot of Water Populations in a Clot

T2 relaxation rate data was collected from CK blood samples drawn from healthy patients. For each sample, a series of T2 decay curves were measured over a period of 50 minutes. The decay curves were each processed using an inverse Laplace transform (ILT CONTIN) to provide an array of curves showing T2 intensity as a function of T2 time. These curves were compiled to form 3D data sets by stacking the inverse Laplace transform curves over the duration of the clotting time dimension to generate a 3D surface that shows how the different populations of water within the sample change as a function of time. FIG. 20 illustrates the 3D data sets for patient samples 29328 and 29350 collected on a Bruker minispec. The 3D data sets showed an initial water population with a T2 time of 250-500 milliseconds that corresponds to unclotted blood. At a time between 5 minutes and 30 minutes, the single water population diverged into two significant water populations. These two water populations correspond to the two components of the clot, i.e., the retracted clot and the serum surrounding the retracted clot. The first clot-associated water population had a T2 time of 80-400 milliseconds and corresponded to the retracted clot. The second clot-associated water population had a broader range of T2 times, from 400-3000 milliseconds, and corresponded to the serum surrounding the retracted clot. For some samples these two peaks were not entirely resolved. The correlation between the water populations and the components of the clotted sample was confirmed by separating the retracted clot from the surrounding serum and separately measuring the T2 data for these two components.

EXAMPLE 14

Inhibition of Platelet Activity Using Abciximab

The clotting of a whole blood sample was perturbed using the antithrombotic agent abciximab (ReoPro®). Abciximab is the Fab fragment of a human-murine monoclonal antibody that binds to the IIb/IIIa receptor of human platelets and inhibits platelet aggregation. Abciximab serves to inhibit the retraction of a clot during the clotting process.

Samples containing abciximab were prepared according to the following procedure and referenced in the application and Figures by a number corresponding to the concentration of abciximab in units of µg/mL.

1. Blood was drawn from normal donors into six citrate tubes. Normal donors must not have taken aspirin or any anti-platelet drug in the past two weeks.

2. The six tubes of blood were pooled and mixed gently by inversion eight to ten times. Samples were used within two hours of collection.

3. A abciximab solution (10 mg/5 mL) was diluted at a ratio of 1:4 using saline as a diluent to form "solution 1."

4. The blood was spiked with solution 1 and saline according to Table 5

5. The samples were allowed to sit for at least five minutes prior to running any sample in a T2reader or Bruker minispec.

TABLE 5

Preparation of blood samples containing abciximab

| µl Solution 1 | µl Saline | µl Blood | Reopro ® (µg/ml) |
|---|---|---|---|
| 0 | 96 | 1904 | 0 |
| 2 | 62 | 1936 | 0.50 |
| 4 | 60 | 1936 | 1 |
| 6 | 58 | 1936 | 1.5 |
| 8 | 56 | 1936 | 2 |
| 10 | 54 | 1936 | 2.5 |
| 12 | 52 | 1936 | 3 |
| 16 | 48 | 1936 | 4 |
| 24 | 40 | 1936 | 6 |
| 32 | 32 | 1936 | 8 |

In a first experiment, four aliquots of patient sample 29488 were prepared with different concentrations of abciximab (0, 2, 4, and 8 µg/mL) prior to initiation of the clotting process. The T2 relaxation times for the four samples were measuring over the course of clot formation and the corresponding 3D plots were determined using the technique described in Example 13. A clear trend was evident in the four 3D plots, with higher concentrations of abciximab resulting in the coalescing of the retracted clot water population and the serum water population into a single water population. At the highest concentration of abciximab, there was no longer two phases visible within the clot. This physical change is evidenced and quantified in the corresponding 3D plots (FIG. 21), showing fast exchange of water within the uniform sample at the highest concentration of abciximab.

Figure 22:
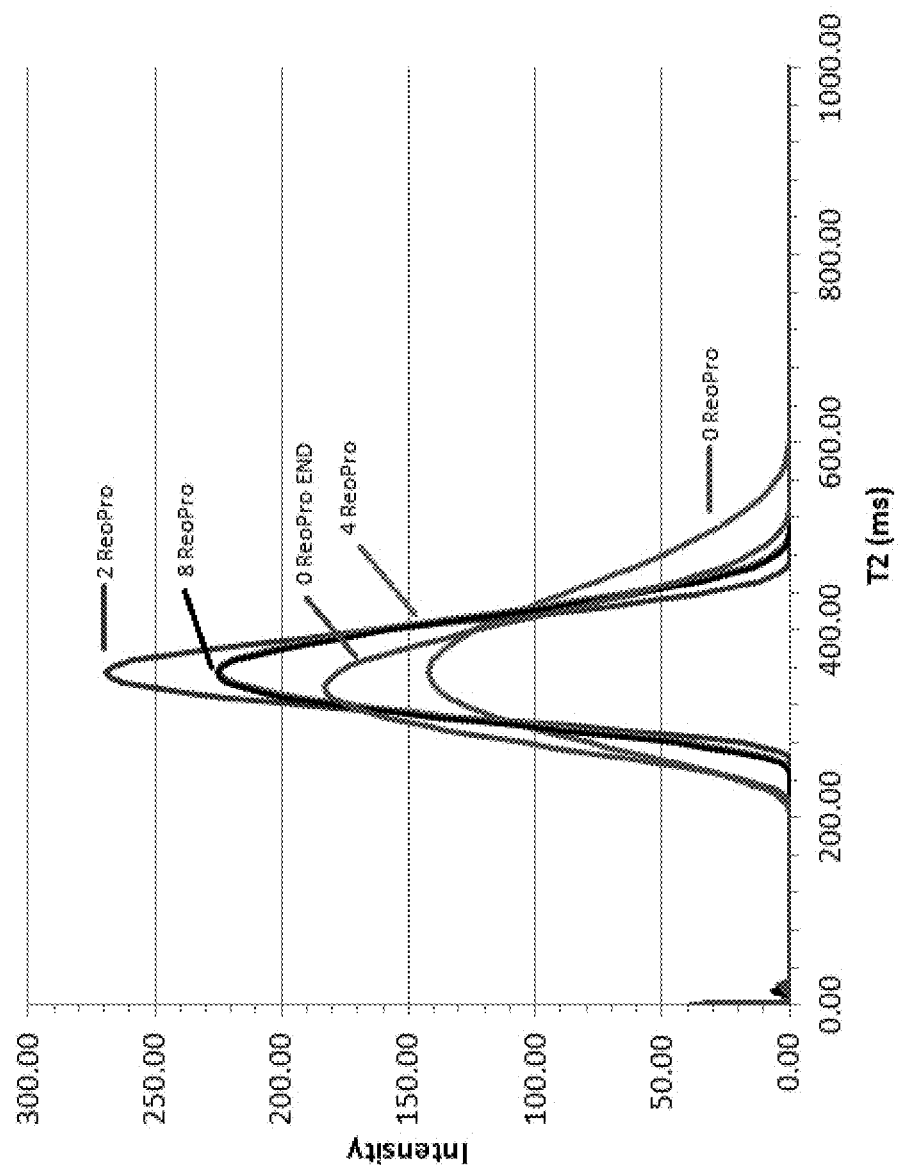
FIG. 22 depicts T2 relaxation rate spectra for five blood samples containing different concentrations of abciximab at 0.1 minutes, as described in Example 14. The data was collected on a Bruker minispec.
Figure 23:
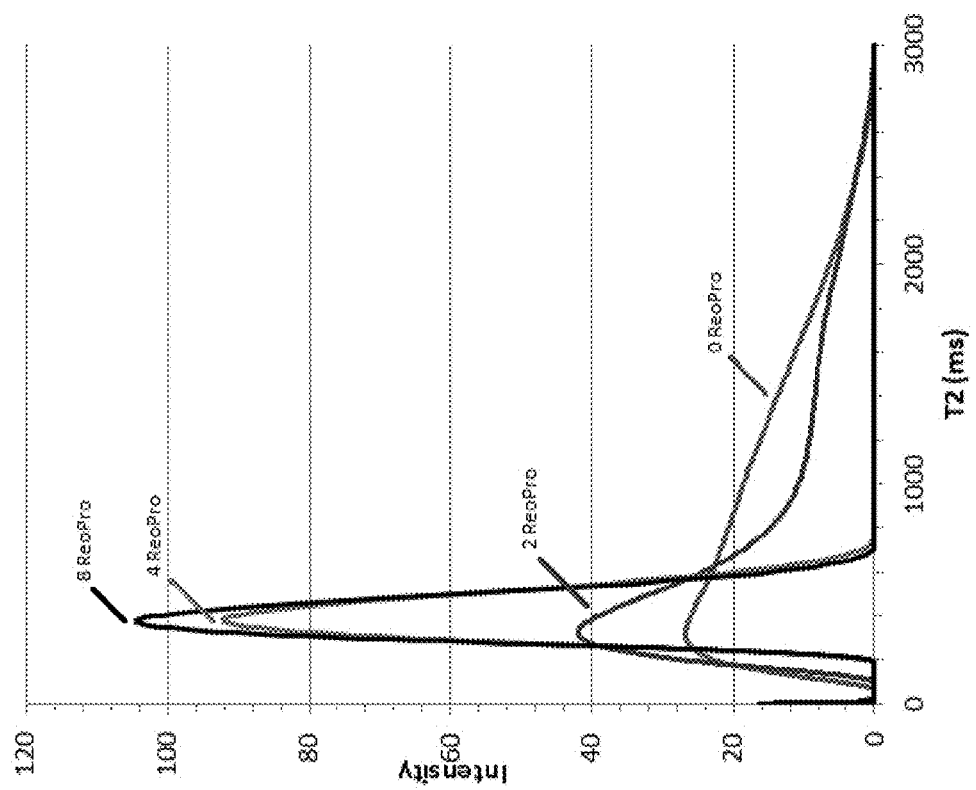
FIG. 23 depicts T2 relaxation spectra for four blood samples containing different concentrations of abciximab at 20 minutes, as described in Example 14. The differences between the four T2 relaxation spectra illustrate the effect of the anti-platelet agent on the distribution of water into discrete populations within the sample during clotting. These differences correspond to differences in the clot strength, as measured by TEG, with clot strength decreasing as the water populations merge at the higher concentrations of abciximab. The data was collected on a Bruker minispec.

In a second experiment, five aliquots of patient sample 29494 were prepared with different concentrations (0, 2, 4, 8, and 0 µg/mL) of abciximab prior to initiation of the clotting process. The T2 relaxations times for the samples were measured in series, with each set of measurements lasting approximately 50 min. The first sample tested and the final sample tested contained no added abciximab. The collected T2 decay curves were processed using inverse Laplace transforms, as described in Example 18. The data at a time of 0.1 minutes for the five samples is shown in FIG. 22. The curves illustrate that in the presence of abciximab a narrower distribution of T2 signals are observed within the initial water population present in the blood sample. The difference in the curve shape between the first sample run and the final sample run, both of which contained no added abciximab, may be evidence of an effect of sample age on the T2 time distribution. The data at a time of 20 minutes for the first four samples is shown in FIG. 23. The corresponding TEG-determined MA values for these samples was 60.7, 61.4, 30.4, and 22.0, respectively. The two samples having the highest concentrations of abciximab formed weaker clots, as measured by TEG, and displayed narrower, more resolved T2 peaks than the other two samples, which formed stronger clots and exhibited poorly resolved T2 peaks, indicative of multiple water populations and non-uniformity of the environments within these samples. This data demonstrate that the NMR-based methods of the invention can be used to measure platelet activity within a clotting sample. FIGS. 22 and 23 show that an additive that modulates the clotting behavior of a sample, such as abciximab, can be advantageously used to establish correlations between TEG-determined indices (e.g., clot strength and platelet activity) and NMR-derived data determined using the methods of the invention.

Figure 24:
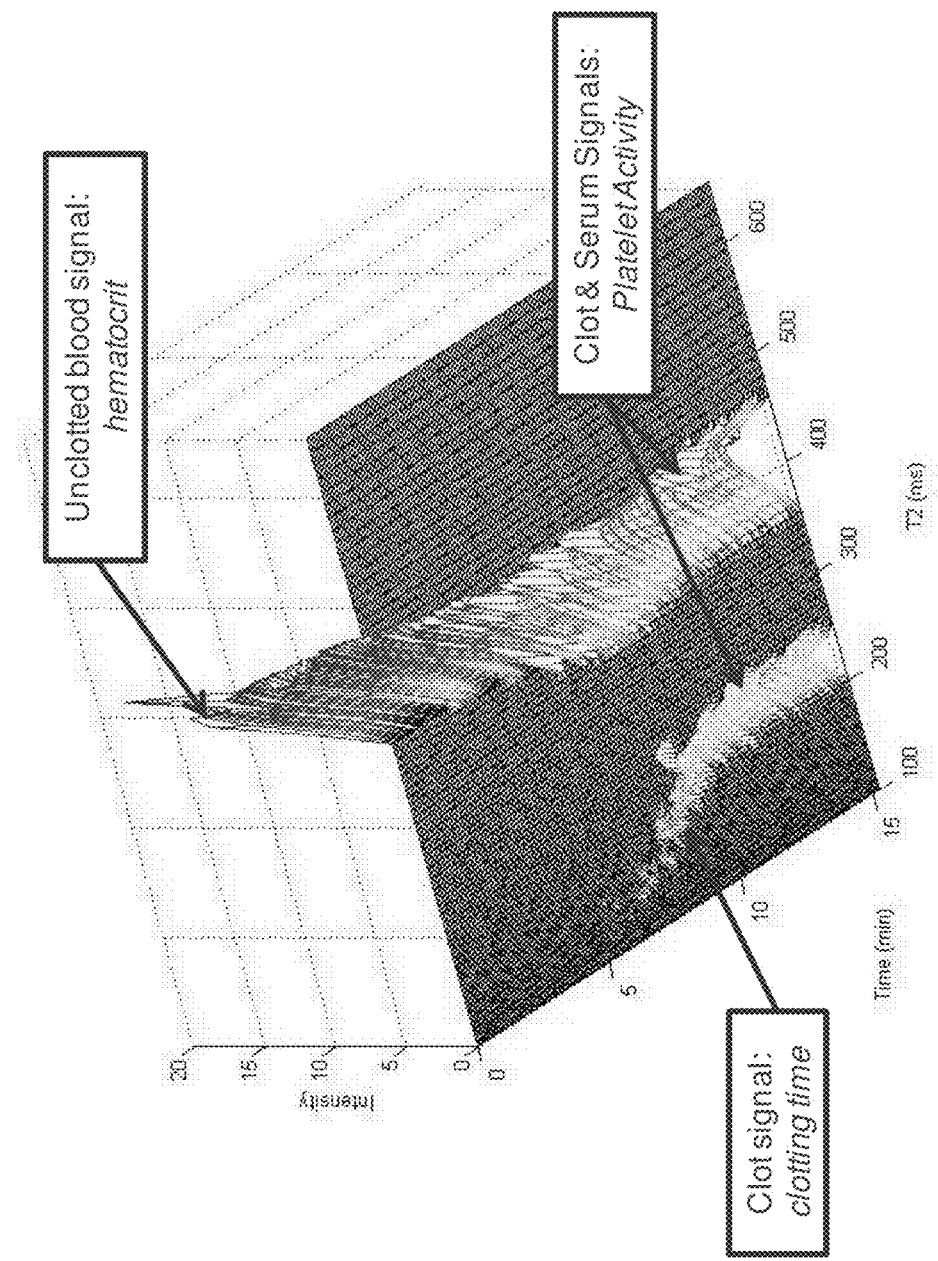
FIG. 24 depicts a 3D plot constructed from a 3D data set collected using a T2reader. The 3D plot shows an initial significant water population that rapidly decreases in intensity. At a time between 8 and 10 minutes, two distinct water populations emerge. The emergence of the water population with a lower T2 value (the population corresponding to the clot-associated T2 signal) corresponds with the clotting time.
Figure 25B:
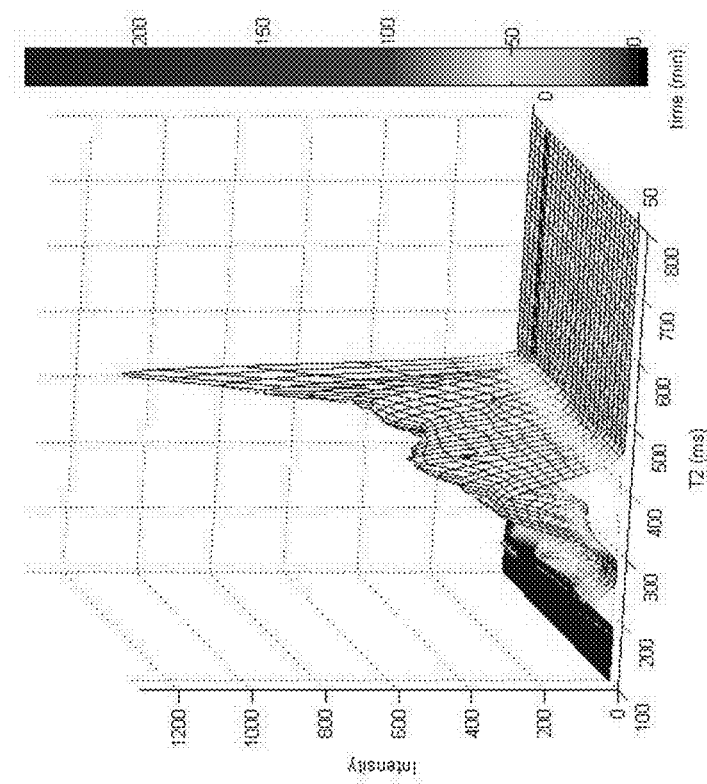
FIGS. 25A and 25B depicts two 3D plots constructed from a 3D data set collected using a T2reader for a native sample with no added Reopro® (FIG. 25A) and a sample with inhibited platelets with 8 µg/mL Reopro® (FIG. 25B). The 3D plot shows an initial significant water population that rapidly decreases in intensity. At a time between 6.3 and 8.5 minutes, two distinct water populations emerge for the native sample in FIG. 25A. Platelet inhibition reduces the signal intensity of the clot associated signal and shifts the serum associated signal to lower T2 values.
Figure 25A:
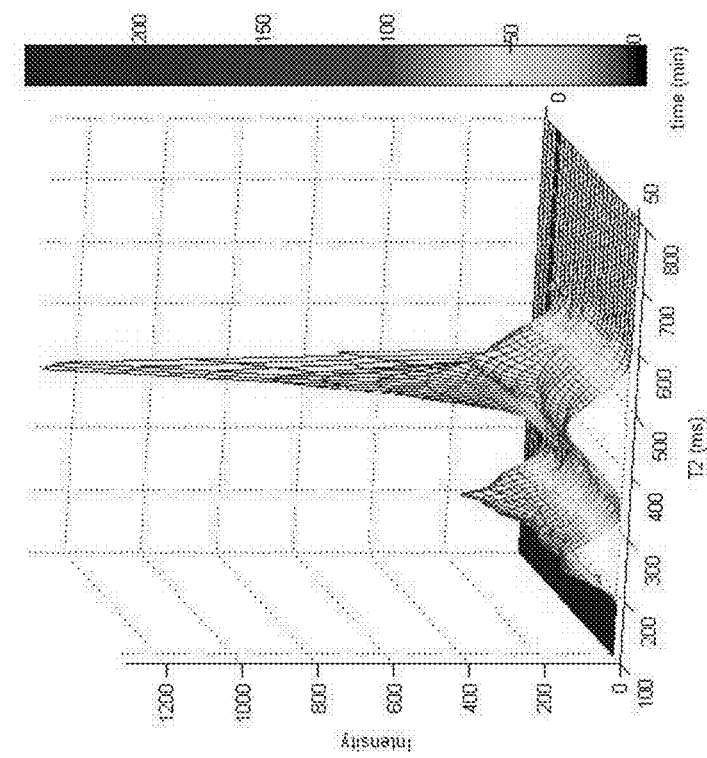

FIG. 24 shows how a 3D plot constructed from a 3D data set can be used to determine the clotting time for a blood sample. FIG. 25 shows, using a 3D plot constructed from a 3D data set, how platelet inhibition reduces the signal intensity of the clot associated signal and shifts the serum associated signal to lower T2 values.

EXAMPLE 15

Assessing Data Quality and Fit Quality

The T2 coagulation data for a single sample consists of a collection of S observed T2 CPMG relaxation curves $\{f_j(t): 0<t<T, j=0, 1, 2, 3, \ldots S\}$, where $j=0, 1, 2, \ldots, S$ are points in time throughout a sample's coagulation/clot forming process, with $j=0$ corresponding to clot initiation and $j=S$ a point after the sample has undergone an expected coagulation event. The T2 coagulation algorithm transforms this collection of decay functions into a surface of decay constant potentials over the T2×Clotting Time domain and then extracts useful information about the sample from these potentials.

A single T2 CPMG relaxation data $f_j(t)$ will be modeled as a finite sum of weighted exponential decay functions using equation (3). Typically n is large (e.g., n>300) due to sample complexity. Many algorithms have been developed to estimate this model's parameters (see Istratov et al., Rev. Sci. Instrum. 70:1233 (1999)). For example, the Tikhonov regularization method (see Tikhonov Soy. Math. Dokl. 4:1035 (1963)) can implemented in CONTIN (see Provencher, Comput. Phys. Commun 27:229 (1982)) to evaluate the relaxation data collected in the methods of the invention. As is common (see Davies, Inversion Problems in Scattering and Imaging, edited by M. Bertero and E. R. Pike (Adam Hilfer, Bristol, 1992), p. 393), the use of this inversion method for T2 coagulation relaxation data can require the application of specific modifications or settings, such as those provided below.

The inverse Laplace transform is known to be an ill-posed computation, which means that many equally accurate solutions may arise from a given complex decay dataset. This is true of the cleanest data, and worsens as the composite decay curve becomes noisier or moves markedly from a sum of mono-exponential decay functions.

CPMG Data Quality

To address this problem, prior to inversion, each T2 CPMG dataset can be tested to establish the quality of the both the data and the overall likelihood that the inversion will be successful. Signal to noise ratios (SNRs) are estimated based on the CPGM intensity at t=0 compared to the variation observed late in the relaxation data, i.e. t near T. Low SNR values resulting from decreases in initial signal are associated with instrument and operator error that disqualify the data from consideration. Low SNR can also arise from increased variation late in the CPMG data or when the observation duration of the decay process was too short. The latter case suggests that the decay constants in a given dataset are larger than expected. Since the Tikhonov regularization method requires knowledge of the maximum T2 value expected, the T2 algorithms accommodate cases of low SNR due to linear trends late in the CPMG curve by increasing the maximum expect T2 value (parameter in CONTIN).

Increased variation also arises when a small number of extreme points (relative to the composite decay assumption) can be found in the tail of a CPMG curve. After fitting subsections of a CPMG curve ($0<t1<t<t2<T$) with mono-exponential decay functions, points found in the positive or negative tails of the distribution of fit residuals are removed prior to inversion.

After the T2 CPMG data passes qualification, in instances when the decay process has been observed long enough to allow for the application of a Jackknife test of the fit, the CPMG data is randomly split into two subsets Train and Test such that Train has no more than 8,000 data points with the remainder being assigned to the Test set. The Train data is inverted and the resulting model parameters, which define a multi-exponential decay function, are used to assess fit quality on the Test data. Fit quality on the Test data gives an independent measure of fit, and is used in the feature extraction phase of the T2 coagulation algorithm.

CONTIN Parameter Values

Several CONTIN parameters dramatically influence the quality of the inverse Laplace transform. Table 6 documents those parameters and the values used by the T2 coagulation algorithm to best fit the T2 CPMG data. The regularization value ($\alpha$) plays a major role in one's ability to resolve two or more T2 peaks. The T2 coagulation algorithm requires narrow peaks to distinguish when subpopulations of water molecules begin to distinguish themselves from other populations. The specific range of $\alpha$ values specified in Table 6 forces CONTIN to search for solutions with regularization weights that allow for this subpopulation discrimination.

TABLE 6

CONTIN Parameters and Values for T2 coagulation algorithm

| Name | Value | Description |
| --- | --- | --- |
| NG | Varies by sample | Number of T2 grid points used for ILT |
| GMNMX(1) | 1 | Minimum T2 value (msec) |
| GMNMX(2) | Varies by sample | Maximum T2 value (msec) |
| NONNEG | 1 | Search for non-negative solution only |
| NQPROG(1) | 0 | Number of course grid alpha (regularization parameter) search attempts |
| NQPROG(2) | 12 | Number of fine grid alpha (regularization parameter) search attempts |
| RSVMNX(3) | 4E0 | Defines minimum alpha in Fine grid search |
| RSVMNX(4) | 1E-7 | Defined maximum alpha in Fine grid search |
| RUSER(21) | 1 | Sets R21 in fm^2 * lambda^R23 * exp(-R21 * tk * lambdam^R22) |
| RUSER(22) | -1 | Sets R22 in fm^2 * lambda^R23 * exp(-R21 * tk * lambdam^R22) |
| RUSER(23) | -1 | Sets R23 in fm^2 * lambda^R23 * exp(-R21 * tk * lambdam^R22) |

The minimum T2 value is typically set in the range of 1-50 ms. This accounts for CPMG time constants arising from plastics in the sample containers. When the minimum is increased above 1 ms, the CPMG curve data on which ILT is performed must be truncated to exclude those short time constants not admitted to the inversion. For example, if the minimum T2 were set at 40 ms, the CPMG data collected prior to 40 ms would be removed prior to performing the ILT.

The maximum T2 value varies by sample/assay type and usage mode in the following ways. Platelet rich and poor plasma samples, which contain few RBCs, require larger maximum T2 values. PPP and PRP maximum T2 values are set in the range of 2500-3500 ms. RBC containing samples will have maximum T2 values in the range of 1000-2000 ms. The maximum T2 value may also be reduced when magnetic particles are included in the sample. For situations in which there is no predicted T2 value, the maximum T2 values can be set in the range of 2500-4000 ms to admit the broadest range of potential T2 values while examining novel sample types. Because ILT fits attempt to account for the entire CPMG curve, but do so over a finite range of T2 values, spurious peaks can occur at the T2 fit boundaries. To accommodate this, an additional 0.5-1 seconds is added to the maximum T2 value used. The ranges provided above include this additional time.

The Tikhonov regularization method includes a parameter (alpha) that controls the inversion's smoothness across the T2 domain. Too small and the peaks are broad with the potential of producing compound peaks, too large and the peaks are more narrow with the potential to split single peaks into several closely placed peaks. CONTIN, as an implementation of the Tikhonov algorithm, is able to search for a regularization term that seeks a compromise between these two extremes. This is accomplished by executing CONTIN without a course alpha grid search, but with an increased fine grid search (12 iterations) within the range of alpha values of about 1.0e-10 and about 4.0e0.

Construction of the T2 Decay Constant Potential Surface

Once each ILT is performed, a collection of curves $\{l_j(\tau_k): 1 < \tau_k < \max T2, k=1, 2, 3, \ldots, N, j=0, 1, 2, 3, \ldots S\}$ replaces the original collection of CPMG curves $f_j t$. For a given CPMG curve $f_j$, the decay constant $\tau_k$ is estimated to contribute $l_j(\tau_k)$ to the multi-exponential decomposition (see equation 13):

$$f_j(t) \sim \sum_{k=1,N} l_j(\tau_k) \exp\left(\frac{-t}{\tau_k}\right) + O, \quad (13)$$

where $l_j(\tau_k)$ may be zero for many k. Changes in the non-zero decay constants and their contributions to the decomposition above over time correspond to changes in the sample and the T2 coagulation algorithm interprets these values and their changes to derive information about the rheological state of a sample or to derive information about a hemostatic condition of a subject. Prior to extracting these features, spurious peaks and multi-modal peaks are resolved (as described below).

Spurious Peak Identification and Removal

In general, for a given j, the ILT amplitude values $l_j(\tau_k)$ are clustered in the T2 domain around a small (<6) regions where the values are non-zero. Ideally, these islands of non-zero intensity are unimodal and away from the boundaries of the range of T2 values over which the inversion was performed. This is not always the case, so care has to be taken to correctly interpret the $l_j(\tau_k)$.

The first filter applied to $l_j(\tau_k)$ is to remove non-zero values where the T2 value is inconsistent with prior expected values based on the type of sample being analyzed. Examples of this include T2<50 ms, which arise from the plastic containing the sample, T2<100 ms if the sample was expected to have high concentrations of protein, and T2 at or near the maximum T2 range used for inversion, whose presence indicates a larger maximum T2 should have been used to invert the sample's CPMG data.

Additionally, while estimating each $l_j(\tau_k)$, the Tikhonov regularization method computes a standard error $\epsilon_j(\tau_k)$ of $l_j(\tau_k)$. When $l_j(\tau_k)$ is near zero, it is common that $l_j(\tau_k) < \epsilon_j(\tau_k)$, which implies the edges of most non-zero islands are ambiguous despite a strong signal near the mean $\tau_k$ of such a collection of non-zero intensities. These $l_j(\tau_k)$ are not removed. Alternatively, when $l_j(\tau_k) < \epsilon_j(\tau_k)$ at a $\tau_k$ at which $l_j(\tau_k)$ is a local maximum, the entire non-zero island is regarded as unreliable and is set to zero.

EXAMPLE 16

Use of Dried or Frozen Reagents

Dried or frozen reagents may be used in the methods of the invention. The results below demonstrate that drying the reagents and freezing the reagents had no discernible influence on the coagulation process observed by T2 relaxation.

Tube-Dried Collagen as a Platelet Activator

Collagen is a potent activator of platelets, and recognition of exposed collagen from the cellular matrix is one of the in vivo signals for platelet activation. We have demonstrated that small aliquots of collagen dried in the bottom of a microtube can effectively generate a T2MR clot peak in both whole blood and RBC-depleted plasma. To prepare the tube, 2 micrograms (2 μL of a 1 mg/ml solution) was deposited in the bottom of a microtube and the tube placed at 37° C. for 2-5 hours. A tube prepared in this way can be kept at room temperature or at 37° C. for several weeks. To measure a T2MR signature 34 μL of citrated whole blood (or RBC-depleted blood) were added to the tube at 37 degrees; after 1 minute 2 μL of 0.2M $CaCl_2$ was added and the sample placed in the magnet for relaxation measurements and analysis.

Frozen One-Pot Formulations for ADP Activation of Platelets

We have developed a standard formulation for ADP activation of platelets in citrated whole blood which uses the addition of heparin to control thrombin activation, thereby minimizing variability in platelet activation via thrombin. Clotting in such a system is initiated with a combination of calcium (to overcome citrate), and reptilase/factor XIIIa (to replace thrombin). The complete one-pot activation mixture which activates platelets via ADP, and is therefore useful in probing the state of the P2Y12 ADP receptor, contains heparin, reptilase, factor XIIIa, calcium, and ADP.

We have demonstrated that such a mixture can be made in small batches and frozen (at −20° C.) in single-use aliquots for T2MR measurement of ADP-induced platelet activity measurements. The use of this mixture consists of thawing a pre-made microtube containing an appropriate amount of reagent mix at room temperature, adding 34 μL citrated whole blood, mixing, and placing the sample in the reader for relaxation measurements analysis.

Dried Kaolin Assay

Kaolin runs permit resolution of the serum and clot signals. Across patient samples, these runs can show variation of the absolute T2 values from user errors. Use of dried reagents avoids pipetting errors and reduces reagent addition variation normally encountered during all wet reagent experiments. Additionally, use of dried reagents provides a much simpler assay protocol where blood is added directly to a tube containing dried reagents with no additional pipetting steps.

A dry mix was prepared containing $CaCl_2$ and Kaolin. 24 µL of 0.2M $CaCl_2$ and 10.8 µL of Kaolin (Haemonetics) were mixed and aliquots distributed into 10 PCR tubes (2.9 µL of prepared mix into each tube). The contents of each tube were dried in an incubator at 37° C. over 2 hours with the tube caps open. Each tub was capped and stored tubes at 2-25° C. To the preheated PCR tube with dried CK reagent mix was added 36 µL of preheated citrated whole blood. The reagents and blood were gently mixed 3 times by pipetting up and down with 100 µL pipette tip. The mixture was capped, and the sample placed into a T2 reader for relaxation measurements analysis. Wet reagents were also combined with citrated whole blood as a control.

EXAMPLE 17

Effect of Aspirin

In this experiment platelet inhibition was monitored by the addition of 600 µM aspirin ex vivo to heparin blood prior to activation by AA+RF (samples were tested with and without aspirin). It was observed that clot-associated T2 signal is dramatically diminished or absent in the presence of samples doped with aspirin. These studies confirmed that the clot signature was dependent on platelet activity. They also demonstrate the utility of T2MR signatures for measuring platelet inhibition.

EXAMPLE 18

Effect of 2-thiomethyl AMP (MeSAMP)

In this experiment inhibition of the P2Y12 pathway in platelets by using the ex vivo spiked MeSAMP (2-thiomethyl AMP, an irreversible ADP P2Y12 receptor inhibitor) as a mimic for Plavix inhibition of platelet activity was tested.

A standard ADP activation formulation including heparin, reptilase, factor XIIIa, calcium, and ADP was used to activate platelet in citrated whole blood obtained from healthy donors. Samples were tested in the presence and absence of the platelet activation inhibitor MeSAMP. Again we observed that the clot signature was dependent on platelet activity. It was observed that clot-associated T2 signal is dramatically diminished or absent in the presence of samples doped with MeSAMP.

EXAMPLE 19

Effect of Tissue Plasminogen Activator

The T2MR surface is also sensitive to whole blood fibrinolysis. To assess this, healthy donor samples were spiked with tissue plasminogen activator (TPA). High sensitivity and rapid time to result for fibrinolysis was demonstrated.

TPA was added at 100 U/mL to blood from a healthy donor. In the absence of TPA (see FIG. 27A) two stable peaks form at the expected clotting time. With 100 U/mL of TPA (see FIG. 27B) the clot forms at the expected time, but proves to be unstable after 20-30 minutes. Both the instability and the distance between the final T2 peaks indicate sensitivity to fibrinolysis induced by the presence of TPA.

The T2MR effect on fibrinolysis was expressed in AU values (arbitrary units; see FIG. 27C) obtained by calculating the difference between the maximum and minimum T2 value observed for the clot signal (or T2B) in the T2 time curve. This difference was found to be sensitive to the degree of fibrinolysis in the samples.

Fibrinolysis was monitored by T2 magnetic resonance (T2MR) in five patient blood samples with and without the addition of TPA (100 U/mL) (FIG. 27C). One sample, 27790, exhibited substantial fibrinolysis without addition of TPA. All other samples required addition of TPA to induce fibrinolysis, as confirmed by the reference method.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method of monitoring a clotting process comprising:
   (i) adding to whole blood obtained from a subject a clotting initiator to initiate a clotting process;
   (ii) during the clotting process making a plurality of T2 relaxation rate measurements on the whole blood sample at a series of time points during said process to produce a plurality of T2 relaxation rate decay curves,
   (iii) transforming the T2 relaxation rate measurements using an algorithm that distinguishes two or more separate water populations within the whole blood sample at one or more of said time points, wherein the two or more water populations comprise a water population having a serum-associated T2 signal and a water population having a clot-associated T2 signal, and the serum-associated T2 signal and the clot-associated T2 signal are separately characterized by one or more magnetic resonance parameters;
   (iv) obtaining values of the one or more magnetic resonance parameters for the water population having a serum-associated T2 signal and a water population having a clot-associated T2 signal; and
   (v) on the basis of the results of step (iv), monitoring said clotting process.

2. The method of claim 1, further comprising (a) calculating the difference between the value of the serum-associated T2 signal and the value of the clot-associated T2 signal; and (b) on the basis of the difference, determining the activity of the platelets in the whole blood.

3. The method of claim 1, further comprising (a) following step (i), measuring the period of time prior to the initial detection of the clot-associated T2 signal; and (b) on the basis of the period of time, determining the clotting time for the whole blood.

4. The method of claim 1, further comprising (a) following step (i), calculating a T2 time curve for a first water population; (b) calculating the maximum value of the second derivative of the T2 time curve; and (c) on the basis of the result of step (c), calculating a value characteristic of clotting time.

5. The method of claim 1, further comprising calculating the T2 value for the whole blood prior to initiating clot formation, and on the basis of the T2 value, determining the hematocrit of the whole blood.

6. The method of claim 1, wherein prior to step (ii), fibrinogen is added to the whole blood sample.

7. The method of claim 1, wherein the clotting initiator is an intrinsic pathway activator.

8. The method of claim 1, wherein the clotting initiator is an extrinsic pathway activator.

9. The method of claim 8, wherein the clotting initiator is tissue factor.

10. The method of claim 1, further comprising determining whether the whole blood is hypercoagulable, hypocoagulable, or normal.

11. The method of claim 10, further comprising, prior to step (i), (a) administering an anticoagulation therapy to the subject; and (b) if the subject is found to be hypercoagulable, identifying the subject as a non-responder to the anticoagulation therapy.

12. The method of claim 1, wherein the whole blood sample has a volume between 2 microliters and 400 microliters.

13. The method of claim 12, wherein the whole blood sample has a volume between 2 microliters and 250 microliters.

14. The method of claim 13, wherein the whole blood sample has a volume between 2 microliters and 50 microliters.

15. The method of claim 1, wherein the whole blood sample has a volume between 200 microliters and 500 microliters.

16. The method of claim 1, wherein step (i) comprises adding the whole blood to a tube containing one or more clotting initiators, and mixing the contents to initiate a clotting process.

17. The method of claim 1, wherein said algorithm comprises an algorithm selected from the group consisting of a multi-exponential algorithm, a bi-exponential algorithm, a tri-exponential algorithm, a decaying exponential algorithm, a Laplace transform, a goodness-of-fit algorithm, an SSE algorithm, a least squares algorithm, and a non-negative least squares algorithm.

18. The method of claim 17, wherein said algorithm is an inverse Laplace transform.

19. The method of claim 18, wherein said inverse Laplace transform includes a lower bound for the T2 time constants of from 1 to 50 ms and an upper bound for the T2 time constants of from 1000 to 4000 ms.

20. The method of claim 19, wherein said blood sample is plasma, platelet poor plasma, or platelet rich plasma, and said upper bound for the T2 time constants is from 2500 to 4000 ms.

21. The method of claim 19, wherein said blood sample is a whole blood sample and said upper bound for the T2 time constants is from 1000 to 2000 ms.

22. The method of claim 19, wherein each of the two or more water populations has a distinct relaxation rate at one or more time points during the clotting process.

23. The method of claim 19, wherein each of the two or more water populations has a distinct T2 signal intensity at one or more time points during the clotting process.

* * * * *